US009051574B2

(12) United States Patent
Galen et al.

(10) Patent No.: US 9,051,574 B2
(45) Date of Patent: Jun. 9, 2015

(54) NON-HEMOLYTIC CLYA FOR EXCRETION OF PROTEINS

(75) Inventors: James E. Galen, Sykesville, MD (US); Yuansha Chen, Gainesville, FL (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 1189 days.

(21) Appl. No.: 12/995,644

(22) PCT Filed: Jun. 2, 2009

(86) PCT No.: PCT/US2009/045972
§ 371 (c)(1),
(2), (4) Date: Dec. 1, 2010

(87) PCT Pub. No.: WO2009/149083
PCT Pub. Date: Dec. 10, 2009

(65) Prior Publication Data
US 2011/0086059 A1    Apr. 14, 2011

Related U.S. Application Data

(60) Provisional application No. 61/058,299, filed on Jun. 3, 2008.

(51) Int. Cl.
*C12N 15/70* (2006.01)
*C12N 15/74* (2006.01)
*C07K 14/255* (2006.01)

(52) U.S. Cl.
CPC .............. *C12N 15/74* (2013.01); *C07K 14/255* (2013.01); *C07K 2319/036* (2013.01)

(58) Field of Classification Search
CPC ......... C12N 15/70; C12N 15/74; A61K 39/00
USPC ...................................... 435/69.7; 424/200.1
See application file for complete search history.

(56) References Cited

U.S. PATENT DOCUMENTS 5,387,744 A    2/1995 Curtiss, III et al.
5,525,504 A *  6/1996 Goebel et al. .............. 435/252.3
(Continued)

FOREIGN PATENT DOCUMENTS

WO          94-28137      12/1994
WO          02-083890     10/2002
(Continued)

OTHER PUBLICATIONS

Galen et al, 2004, Adaptation of the Endogenous *Salmonella enterica* serovar Typhi clyA-encoded Hemolysin for antigen export enhances the immunogenicity of Anthrax Protective Antigen Domain 4 expressed by the Attenuated Live Vector Vaccine Strain CVD 908-htrA, Infection and Immunity, vol. 72(12), Dec. 1, 2004, pp. 7096-71-6.*

(Continued)

*Primary Examiner* — Albert Navarro
*Assistant Examiner* — Ginny Portner
(74) *Attorney, Agent, or Firm* — Roylance, Abrams, Berdo & Goodman, L.L.P.

(57) ABSTRACT

The disclosure below provides a protein export system utilizing non-hemolytic variants of HlyE family member proteins for efficiently producing recombinant protein from a host cell. In a preferred embodiment, the protein export system utilizes protein export machinery endogenous to the host bacterium into which the protein export system vector is introduced.

27 Claims, 16 Drawing Sheets

(56) References Cited

U.S. PATENT DOCUMENTS

| | | | |
|---|---|---|---|
| 5,731,151 A * | 3/1998 | King et al. | 435/6.13 |
| 6,004,815 A * | 12/1999 | Portnoy et al. | 435/454 |
| 6,383,496 B1 * | 5/2002 | Curtiss et al. | 424/200.1 |
| 6,413,768 B1 | 7/2002 | Galen | |
| 6,703,233 B1 | 3/2004 | Galen | |
| 6,902,736 B2 | 6/2005 | Altboum et al. | |
| 7,056,700 B2 * | 6/2006 | Galen | 435/69.7 |
| 7,090,850 B2 | 8/2006 | Nataro | |
| 7,459,161 B2 * | 12/2008 | Galen | 424/200.1 |
| 8,728,760 B2 * | 5/2014 | Galen et al. | 435/69.1 |
| 2002/0146430 A1 * | 10/2002 | Galen | 424/200.1 |
| 2005/0196754 A1 * | 9/2005 | Drmanac et al. | 435/6 |
| 2006/0147461 A1 * | 7/2006 | Galen | 424/190.1 |
| 2009/0297556 A1 * | 12/2009 | Baillie | 424/200.1 |
| 2010/0233195 A1 * | 9/2010 | Delisa et al. | 424/184.1 |
| 2012/0282293 A1 * | 11/2012 | Galen | 424/200.1 |
| 2014/0161854 A1 * | 6/2014 | Kotyla | 424/401 |

FOREIGN PATENT DOCUMENTS

| | | | |
|---|---|---|---|
| WO | 02/083890 | * 10/2002 | |
| WO | 2008/048289 | * 4/2008 | A61K 30/07 |
| WO | 2008/147816 | 12/2008 | |

OTHER PUBLICATIONS

Kim, J.-Y. et al., Engineered Bacterial Outer Membrane Vesicles with Enhanced Functionality, J. Mol. Biol., vol. 380, pp. 51-66 (2008).

von Rhein, C. et al., ClyA cytolysin from *Salmonella*: Distribution within the genus, regulation of expression by SlyA, and pore-forming characteristics, International Journal of Medical Microbiology, vol. 299, pp. 21-35 (Jan. 2009).

International Search Report and Written Opinion for PCT/US09/045972, dated Jan. 19, 2010.

Atkins, A., et al. 2000. Structure-function relationships of a novel bacterial toxin, hemolysin E. The role of αG J. Biol. Chem. 275(52):41150-41155.

Blomfield, I. C., et al. 1991. Allelic exchange in *Escherichia coli* using the *Bacillus subtilis* sacB gene and a temperature-sensitive pSC101 replicon. Mol. Microbiol. 5:1447-1457.

Boe, L., et al. 1987. Effects of genes exerting growth inhibition and plasmid stability on plasmid maintenance. J. Bacteriol. 169:4646-4650.

Borchert, T. V. and V. Nagarajan. 1991. Effect of signal sequence alterations on the export of levansucrase in *Bacillus subtilis*. J. Bacteriol. 173:276-282.

Chervaux, C., et al. 1995. Secretion of active β-lactamase to the medium mediated by the *Escherichia coli* haemolysin transport pathway. Mol. Gen. Genet. 249:237-245.

Corchero, J. L. and A. Villaverde. 1998. Plasmid maintenance in *Escherichia coli* recombinant cultures is dramatically, steadily, and specifically influenced by features of the encoded proteins. Biotechnol. Bioeng. 58:625-632.

Cserjan-Puschmann, M., et al. 1999. Metabolic approaches for the optimisation of recombinant fermentation processes. Appl. Microbiol. Biotechnol. 53:43-50.

del Castillo, F. J., et al. 1997. The *Escherichia coli* K-12 sheA gene encodes a 34-kDa secreted haemolysin. Mol. Microbiol. 25:107-115.

Fouet, A., et al 1984. Characterization of the precursor form of the exocellular levansucrase from *Bacillus subtilis*. Biochem. Biophys. Res. Commun. 119:795-800.

Galen, J. E., et al. 1997. A murine model of intranasal immunization to assess the immunogenicity of attenuated *Salmonella typhi* live vector vaccines in stimulating serum antibody responses to expressed foreign antigens. Vaccine 15:700-708.

Galen, J. E., et al. 1999. Optimization of plasmid maintenance in the attenuated live vector vaccine strain *Salmonella typhi* CVD 908-htrA. Infect. Immun. 67:6424-6433.

Galen, J. E., et al. 2009. *Salmonella enterica* serovar *Typhi* live vector vaccines finally come of age. Immunol. Cell Biol. 87(5):400-12.

Galen, J. E., et al. 2009. Mucosal immunization with attenuated *Salmonella enterica* serovar *Typhi* expressing protective antigen of anthrax toxin (PA83) primes monkeys for accelerated serum antibody responses to parenteral PA83 vaccine. J. Infect. Dis. 199:326-335.

Gay, P., et al. 1983. Cloning structural gene sacB, which codes for exoenzyme levansucrase of *Bacillus subtilis*: expression of the gene in *Escherichia coli*. J. Bacteriol. 153:1424-1431

Glick, B. R. 1995. Metabolic Load and Heterologous Gene Expression. Biotechnol. Adv. 13:247-261.

Harcum and Bentley. 1993. Response Dynamics of 24-, 36-, 39-, 54- and 80-kDa Proteases in Induced Cultures of Recombinant *Escherichia coli*. Biotechnol. Bioeng. 42:675-685.

Hone, D. M., et al. 1991. Construction of genetically defined double aro mutants of *Salmonella typhi*. Vaccine 9:810-816.

Jung, H., et al. 1998. Surface display of *Zymomonas mobilis* levansucrase by using the ice-nucleation protein of *Pseudomonas syringae*. Nat. Biotechnol. 16:576-580.

Lattemann, C. T., et al. 2000. Autodisplay: functional display of active β-lactamase on the surface of *Escherichia coli* by the AIDA-I autotransporter. J. Bacteriol. 182:3726-3733.

Le Coq, D., et al. 1984. A genetic approach to levansucrase secretion in *Bacillus subtilis*, p. 141-152. In A. T. Ganesan and J. A. Hoch (eds.), Genetics and biotechnology of bacilli. Academic Press, New York.

Ludwig, A., et al. 1999. Analysis of the SlyA-controlled expression, subcellular localization and pore-forming activity of a 34 kDa haemolysin (ClyA) from *Escherichia coli* K-12. Mol. Microbiol. 31:557-567.

Orr, N. et al. 1999. Expression and immunogenicity of a mutant diphtheria toxin molecule, CRM197, and its fragments in *Salmonella typhi* vaccine strain CVD 908-htrA. Infect. Immun. 67:4290-4294.

Oscarsson, J., et al. 1999. Molecular analysis of the cytolytic protein ClyA (SheA) from *Escherichia coli*. Mol. Microbiol. 32:1226-1238.

Oscarsson, J., et al. 1996. Induction of haemolytic activity in *Escherichia coli* by the slyA gene product. Mol. Microbiol. 20:191-199.

Oscarsson et al. 2002. Characterization of a Pore-Forming Cytotoxin Expressed by *Salmonella enterica* Serovars *Typhi* and *Paratyphi A*. Infect. Immun. 70:5759-5769.

Pecota, D. C., et al. 1997. Combining the hok/sok, parDE, and pnd postsegregational killer loci to enhance plasmid stability. Appl. Environ. Microbiol. 63:1917-1924.

Pluckthun, A. and J. R. Knowles. 1987. The consequences of stepwise deletions from the signal-processing site of β-lactamase. J. Biol. Chem. 262:3951-3957.

Ried, J. and A. Collmer. 1987. An npl-sacB-sacR cartridge for constructing directed,unmarked mutations in Gram-negative bacteria by marker exchange-eviction mutagenesis. Gene 57:239-246.

Sansonetti, P. J., et al. 1986. Multiplication of *Shigella flexneri* within HeLa cells: lysis of the phagocytic vacuole and plasmid-mediated contact hemolysis. Infect. Immun. 51: 461-9.

Smith, M. A., and M. J. Bidochka. 1998. Bacterial fitness and plasmid loss: the importance of culture conditions and plasmid size. Can. J. Microbiol. 44:351-355.

Steinmetz, M., et al. 1983. Genetic analysis of sacB, the structural gene of a secreted enzyme, levansucrase of *Bacillus subtilis* Marburg. Mol. Gen. Genet. 191:138-144.

Summers, D. K. 1998. Timing, self-control and sense of direction are the secrets of multicopy plasmid stability. Mol. Microbiol. 29:1137-1145.

Sutcliffe, J. G. 1978. Nucleotide sequence of the ampicillin resistance gene of *Escherichia coli* plasmid pBR322. Proceedings of the National Academy of Sciences USA 75:3737-3741.

Tacket, C. O., et al. 1997. Safety of live oral *Salmonella typhi* vaccine strains with deletions in htrA and aroC aroD and immune responses in humans. Infect. Immun. 65:452-456.

Wallace, A. J., et al. 2000. *E. coli* hemolysin E (HlyE, ClyA, SheA): X-ray crystal structure of the toxin and observation of membrane pores by electron microscopy. Cell 100:265-276.

Wang, J. Y., et al. 2000. Constititive expression of the Vi polysaccharide capsular antigen in attenuated *Salmonella enterica* serovar *Typhi* oral vaccine strain CVD 909. Infect. Immun. 68:4647-4652.

(56) References Cited

OTHER PUBLICATIONS

Wang, J. Y., et al. 2001. Construction, genotypic and phenotypic characterization, and immunogenicity of attenuated DguaBA *Salmonella enterica* serovar *Typhi* strain CVD 915. Infect. Immun. 69:4734-4741.

Wu, K. and T. K Wood. 1994. Evaluation of the hok/sok killer locus for enhanced plasmid stability. Biotechnol. Bioeng. 44:912-921.

Galen, J. et al., Adaptation of the endogenous *Salmonella enterica* serovar typhi clyA -encoded hemolysin for antigen export enhances the immunogenicity of anthrax protective antigen domain 4 expressed by the attenuated live-vector vaccine strain CVD 908-htrA, Infection and Immunity, 2004, vol. 72, No. 12, pp. 7096-7106.

Gentschev, I. et al., Development of antigen-delivery systems, based on the *Escherichia coli* hemolysin secretion pathway, Gene, 1996, vol. 179, No. 1, pp. 133-140.

Extended European Search Report dated Oct. 11, 2011, from corresponding European Application No. EP 09759243.0.

* cited by examiner

Figure 2
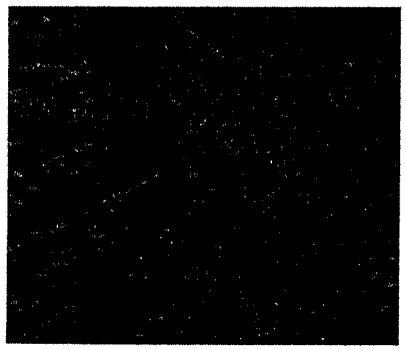

Figure 11

```
                              490        500        510        520        530        540
wt ClyA    Sequence    gaaaaaagca gctattttca gagccaggtg gatagaattc gtaaagaagc ctatgccggc
           Translate   E  K  S  S  Y  F  Q  S  Q  V  D  R  I  R  K  E  A  Y  A  G
I198N      Sequence    gaaaaaagca gctattttca gagccaggtg gatagaattc gtaaagaagc ctatgccggc
           Translate   E  K  S  S  Y  F  Q  S  Q  V  D  R  I  R  K  E  A  Y  A  G
198,199,204 Sequence   GAAAAAAGCA GCTATTTTCA GAGCCAGGTG GATAGAATTC GTAAAGAAGC CTATGCCGGC
           Translate   E  K  S  S  Y  F  Q  S  Q  V  D  R  I  R  K  E  A  Y  A  G 550        560        570        580        590        600
wt ClyA    Sequence    gctgcagccg gcattgtggc tggtccgttt ggcctgatta tcagctatag cattgccgcg
           Translate   A  A  A  G  I  V  A  G  P  F  G  L  I  I  S  Y  S  I  A  A
I198N      Sequence    gctgcagccg gcattgtggc tggtccgttt ggcctgatta tcagctatag caatgccgcg
           Translate   A  A  A  G  I  V  A  G  P  F  G  L  I  I  S  Y  S  N  A  A
198,199,204 Sequence   GCTGCAGCCG GCATTGTGGC TGGTCCGTTT GGCCTGATTA TCAGCTATAG CAATGACGCG
           Translate   A  A  A  G  I  V  A  G  P  F  G  L  I  I  S  Y  S  N  D  A 610        620        630        640        650        660
wt ClyA    Sequence    ggcgttattg aaggcaaact gattccggaa ctgaataacc gtctgaaaac cgttcagaat
           Translate   G  V  I  E  G  K  L  I  P  E  L  N  N  R  L  K  T  V  Q  N
I198N      Sequence    ggcgttattg aaggcaaact gattccggaa ctgaataacc gtctgaaaac cgttcagaat
           Translate   G  V  I  E  G  K  L  I  P  E  L  N  N  R  L  K  T  V  Q  N
198,199,204 Sequence   GGCGTTATTA AAGGCAAACT GATTCCGGAA CTGAATAACC GTCTGAAAAC CGTTCAGAAT
           Translate   G  V  I  K  G  K  L  I  P  E  L  N  N  R  L  K  T  V  Q  N 670        680        690        700        710        720
wt ClyA    Sequence    ttctttacaa gcttaagcgc gaccgtgaaa caggcgaaca aagatatcga tgcggcaaaa
           Translate   F  F  T  S  L  S  A  T  V  K  Q  A  N  K  D  I  D  A  A  K
I198N      Sequence    ttctttacaa gcttaagcgc gaccgtgaaa caggcgaaca aagatatcga tgcggcaaaa
           Translate   F  F  T  S  L  S  A  T  V  K  Q  A  N  K  D  I  D  A  A  K
198,199,204 Sequence   TTCTTTACAA GCTTAAGCGC GACCGTGAAA CAGGCGAACA AAGATATCGA TGCGGCAAAA
           Translate   F  F  T  S  L  S  A  T  V  K  Q  A  N  K  D  I  D  A  A  K 730        740        750        760        770        780
wt ClyA    Sequence    ctgaaactgg cgaccgaaat tgcggctatt ggcgaaatta aaaccgaaac cgaaaccacc
           Translate   L  K  L  A  T  E  I  A  A  I  G  E  I  K  T  E  T  E  T  T
I198N      Sequence    ctgaaactgg cgaccgaaat tgcggctatt ggcgaaatta aaaccgaaac cgaaaccacc
           Translate   L  K  L  A  T  E  I  A  A  I  G  E  I  K  T  E  T  E  T  T
198,199,204 Sequence   CTGAAACTGG CGACCGAAAT TGCGGCTATT GGCGAAATTA AAACCGAAAC CGAAACCACC
           Translate   L  K  L  A  T  E  I  A  A  I  G  E  I  K  T  E  T  E  T  T 790        800        810        820        830        840
wt ClyA    Sequence    cgttttatg tggattatga tgacctgatg ctgagcctgc tgaaaggcgc ggcaaagaaa
           Translate   R  F  Y  V  D  Y  D  D  L  M  L  S  L  L  K  G  A  A  K  K
I198N      Sequence    cgttttatg tggattatga tgacctgatg ctgagcctgc tgaaaggcgc ggcaaagaaa
           Translate   R  F  Y  V  D  Y  D  D  L  M  L  S  L  L  K  G  A  A  K  K
198,199,204 Sequence   CGTTTTATG TGGATTATGA TGACCTGATG CTGAGCCTGC TGAAAGGCGC GGCAAAGAAA
           Translate   R  F  Y  V  D  Y  D  D  L  M  L  S  L  L  K  G  A  A  K  K
```

Figure 15

| Group | Immunization regimen[a] | | | Percentage of mice[b] with seroconversion and (GMT)[c] | | | | |
|---|---|---|---|---|---|---|---|---|
| | Prime 1 | Prime 2 | Boost | Day 42 | Day 49 | Day 56 | Day 70 | |
| 1 | CVD 908-*htrA* | CVD 908-*htrA* | PA | 0 (16) | 20 (104) | 100 (9,807) | 100 (223,230) | |
| 2 | CVD 908-*htrA*(pSEC91-83) | CVD 908-*htrA*(pSEC91-83) | PA | 80 (479) | 100 (84,498) | 100 (297,860) | 100 (967,681) | |
| 3 | CVD 908-*htrA* (pS-CPA83-I198N) | CVD 908-*htrA* (pS-CPA83-I198N) | PA | 10 (31) | 100 (15,223) | 100 (120,477) | 100 (670,169) | |
| 4 | CVD 908-*htrA* (pS-CPA83-C285W) | CVD 908-*htrA* (pS-CPA83-C285W) | PA | 0 (15) | 100 (14,079) | 100 (137,606) | 100 (607,847) | |
| 5 | CVD 908-*htrA* (pS-CPA83-DM) | CVD 908-*htrA* (pS-CPA83-DM) | PA | 0 (21) | 100 (4,258) | 100 (85,290) | 100 (699,931) | |
| 6 | PBS | PBS | PBS | 0 (21) | 0 (21) | 0 (21) | 0 (28) | |

[a] Animals received primary immunizations on days 0 and 14 and booster immunizations on day 42.
[b] Represents the percentage of mice that developed reciprocal serum IgG anti-PA titers after vaccination. Sera were tested from twofold serial dilutions starting at 1:50.
[c] Represents geometric mean serum anti-PA titers (GMTs), ELISA units (EUs).

US 9,051,574 B2

NON-HEMOLYTIC CLYA FOR EXCRETION OF PROTEINS

GOVERNMENT SUPPORT

This invention was made with government support under Grant No. MARCE AI057168 awarded by the National Institutes of Health. The government has certain rights in this invention.

BACKGROUND OF THE INVENTION

1. Field of the Invention

The disclosure below relates to the use of a protein export system. The disclosed system provides effective methods and compositions useful for the production of recombinant proteins.

2. Description of the Related Art

Protein expression systems have long used high copy number expression plasmids or expression vectors in an attempt to increase yields of recombinant proteins of interest. High copy number expression plasmids and the proteins of interest they encode can exert a negative effect on the fitness of a host containing an expression plasmid. The notable burden placed upon prokaryotic host cells carrying multicopy plasmids is the cumulative result of a metabolic cascade triggered by two processes: 1) the replication and maintenance of expression plasmids and 2) transcription and translation of the various plasmid-encoded functions including the gene of interest. Such mechanisms could explain the observation that plasmid-bearing bacteria grow slower than plasmid-less bacteria. This burden can also explain the observation that growth rate decreases as copy number increases.

As the gene of interest is expressed, the growth rate of the recombinant host cell decreases. The decrease in growth rate may trigger the induction of various cellular proteases that can degrade recombinantly produced protein present in cytoplasm of the host cell. Reduced growth rate is therefore the inevitable consequence of metabolic burden, which in turn is the cumulative result of a number of physiological perturbations. Because this reduction in the growth rate creates a selective pressure for loss of resident plasmids in the absence of selection, significant loss of expression plasmids from the host cell carrying an expression vector may occur after transformation of the host cell.

Host cells with reduced growth rates can spontaneously shed an expression plasmid to remove from the host cell an unnecessary metabolic burden and allow plasmid-less host cells to quickly outgrow the population of plasmid-bearing host cells. Such a shift in protein expression within a population of host cells would be expected to reduce the protein production.

Accordingly, it would be desirable to prepare a protein expression system that would optimize protein expression from the expression vector while minimizing the metabolic burden on the host cell generated by the expression vector.

SUMMARY OF THE INVENTION

The disclosed material relates to the use of an export protein to facilitate export of a fusion protein out of a host cell. One disclosed embodiment provides a method for expressing a gene in a bacterial cell comprising providing an expression vector to a population of untransformed bacterial host cells, wherein the expression vector comprises an expression cassette comprising an export protein coding sequence genetically fused to a protein of interest coding sequence, expressing the expression cassette such that an export protein::protein of interest fusion protein is produced and exported or transported into the culture medium.

Another disclosed embodiment relates to a method for eliciting an immune response from an animal comprising providing to an animal a population of bacterial host cells transformed with an expression vector which comprises an expression cassette comprising an export protein coding sequence genetically fused to a protein of interest coding sequence, expressing the expression cassette such that an export protein::protein of interest fusion protein is produced and exported or transported into the animal, and eliciting an immune response from the animal against the fusion protein.

Another disclosed embodiment relates to a system for expressing a protein of interest comprising: an expression vector comprising an expression cassette, wherein the expression cassette comprises an export protein coding sequence genetically fused to a protein of interest coding sequence, a host cell transformed with the expression vector, and a culturing environment for the transformed host cell, wherein the expression cassette expresses an export protein::protein of interest fusion protein, which is exported out of the transformed host cell.

In a preferred embodiment, the present invention is directed to a method for producing a fusion protein, comprising (a) transforming a population of bacteria with an expression vector encoding a fusion protein, wherein the fusion protein comprises a protein of interest linked to the carboxy terminus of an export protein, wherein said export protein is a *Salmonella enterica* serovar *Typhi* (*S. Typhi*) cytolysin A (ClyA) protein having substantially reduced hemolytic activity, and (b) culturing transformed bacteria of (a) in a culture medium under conditions such that said fusion protein is expressed and exported into the culture medium. The bacteria may be *Salmonella* spp., *Shigella* spp., *Vibrio* spp., or *E. coli*. Non-limiting exemplary embodiments include but are not limited to *S. Typhi*, such as *S. Typhi* CVD 908 having an htrA mutation, *E. coli*, such as enterotoxigenic *E. coli* (ETEC) or enteroaggregative *E. coli* (EAEC), *Vibrio cholerae*, and *Shigella flexneri* 2a. Further, the protein of interest is an antigen. The method may include the additional step of collecting the fusion protein from the culture medium.

In equally preferred embodiments of this method, the *S. Typhi* cytolysin A (ClyA) protein has the amino acid sequence set forth in SEQ ID NO:2 and a single mutation selected from the group consisting of an S195N mutation, an I198N mutation, an A199D mutation, an E204K mutation, and a C285W mutation; an I198N, C285W double mutation; and an I198N, A199D, E204K triple mutation. The *S. Typhi* cytolysin A (ClyA) protein may also have the amino acid sequence set forth in SEQ ID NO:2 and a C285W mutation, as well as one additional mutation selected from the group consisting of an I198N mutation, an A199D mutation, and an E204K mutation. Alternatively, the *S. Typhi* cytolysin A (ClyA) protein has the amino acid sequence set forth in SEQ ID NO:2 and the protein of interest is anthrax toxin PA83 protein.

In another preferred embodiment, the present invention is directed to a method for eliciting an immune response to a fusion protein in a subject comprising administering to a subject a population of bacteria which produces and exports a fusion protein in an amount sufficient to elicit an immune response in said subject to said fusion protein, wherein said bacteria comprises an expression vector encoding said fusion protein, wherein the fusion protein comprises a protein of interest linked to the carboxy terminus of an export protein, and wherein said export protein is a *Salmonella enterica* serovar *Typhi* (*S. Typhi*) cytolysin A (ClyA) protein having substantially reduced hemolytic activity, thereby eliciting an immune response to said fusion protein in said subject. Preferably the subject is an animal, more preferably a human. The bacteria may be *Salmonella* spp., *Shigella* spp., *Vibrio* spp., or *E. coli*. Non-limiting exemplary embodiments include but are not limited to *S. Typhi*, such as *S. Typhi* CVD 908 having an htrA mutation, *E. coli*, such as enterotoxigenic *E. coli* (ETEC) or enteroaggregative *E. coli* (EAEC), *Vibrio cholerae*, and *Shigella flexneri* 2a. Further, the protein of interest is an antigen.

In equally preferred embodiments of this method, the *S. Typhi* cytolysin A (ClyA) protein has the amino acid sequence set forth in SEQ ID NO:2 and a single mutation selected from the group consisting of an S195N mutation, an I198N mutation, an A199D mutation, an E204K mutation, and a C285W mutation; an I198N, C285W double mutation; and an I198N, A199D, E204K triple mutation. The *S. Typhi* cytolysin A (ClyA) protein may also have the amino acid sequence set forth in SEQ ID NO:2 and a C285W mutation, as well as one additional mutation selected from the group consisting of an I198N mutation, an A199D mutation, and an E204K mutation. Alternatively, the *S. Typhi* cytolysin A (ClyA) protein has the amino acid sequence set forth in SEQ ID NO:2 and the protein of interest is anthrax toxin PA83.

In yet another preferred embodiment, the present invention is directed to an expression vector comprising an expression cassette, wherein the expression cassette comprises an export protein coding sequence linked to a protein of interest coding sequence in a 5' to 3' arrangement, wherein said export protein is a *Salmonella enterica* serovar *Typhi* (*S. Typhi*) cytolysin A (ClyA) protein having substantially reduced hemolytic activity.

In equally preferred embodiments of the expression vector, the *S. Typhi* cytolysin A (ClyA) protein has the amino acid sequence set forth in SEQ ID NO:2 and a single mutation selected from the group consisting of an S195N mutation, an I198N mutation, an A199D mutation, an E204K mutation, and a C285W mutation; an I198N, C285W double mutation; and an I198N, A199D, E204K triple mutation. The *S. Typhi* cytolysin A (ClyA) protein may also have the amino acid sequence set forth in SEQ ID NO:2 and a C285W mutation, as well as one additional mutation selected from the group consisting of an I198N mutation, an A199D mutation, and an E204K mutation. Alternatively, the *S. Typhi* cytolysin A (ClyA) protein has the amino acid sequence set forth in SEQ ID NO:2 and the protein of interest is anthrax toxin PA83.

BRIEF DESCRIPTION OF THE DRAWINGS

FIG. 1A illustrates pSEC84 expression vector. FIG. 1B illustrates pSEC84bla expression vector. FIG. 1C illustrates pSEC84sacB. FIG. 1D illustrates pSEC84gfpuv.

FIG. 2 illustrates exportation of ClyA-SacB protein fusion which results in the metabolism of sucrose in solid growth medium. The strains were grown on media containing either 8% sucrose (2A and 2B), 16% sucrose (2C and 2D), or 8% sucrose+8% L-arabinose (2E and 2F). FIGS. 2A, 2C, and 2E demonstrate the growth of CVD 908-htrA expressing ClyA. FIGS. 2B, 2D, and 2F demonstrate the growth of CVD 908-htrA expressing ClyA-SacB.

FIG. 11 provides an alignment of a portion of the wild-type *S. Typhi* ClyA amino acid sequence ("wt ClyA"), the I198N variant sequence, and the I198N, A199D, E204K variant sequence.

Figure 1:
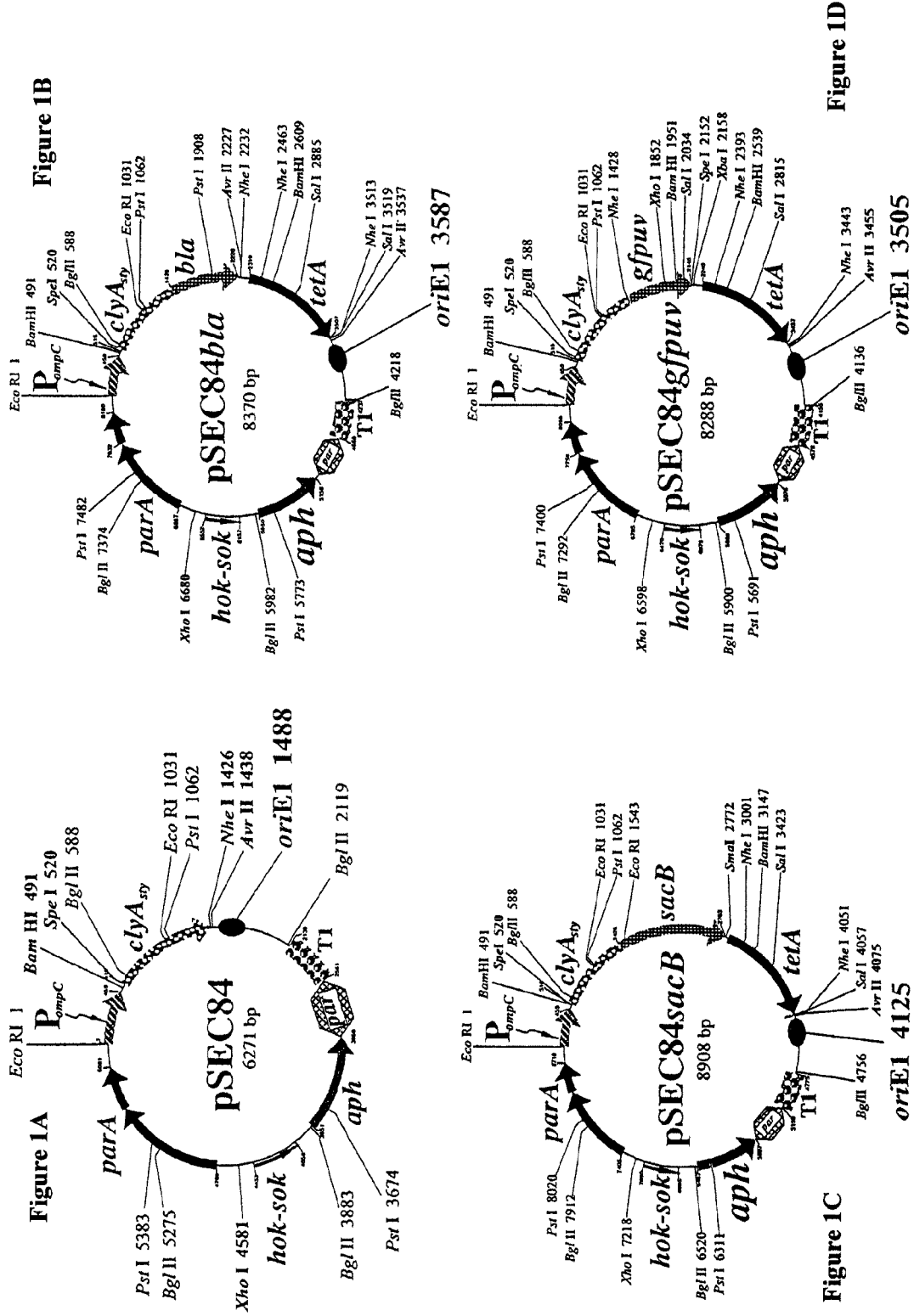
FIG. 1 provides examples of the expression vector of this invention.

In addition, when compared to the sequence encoded by hlyE, N-terminal sequencing of secreted HlyE revealed that HlyE is not N-terminally processed during transport. Oscarsson et al. reported that HlyE binds to cholesterol and that the presence of cholesterol in target membranes stimulates pore formation and lysis (Oscarsson, J., Y. Mizunoe, L. Li, X. Lai, A. Wieslander, and B. E. Uhlin. 1999. Molecular analysis of the cytolytic protein ClyA (SheA) from *Escherichia coli*. Mol. Microbiol. 32:1226-1238). It is estimated that ~$10^3$ molecules of HlyE are required for lysis of a target erythrocyte suggesting significant accumulation of HlyE prior to detection of cell lysis. HlyE is remarkably stable within a range of pH values between 3.0 and 9.0, and is resistant to cleavage by proteases including trypsin and pepsin (Atkins, A., N. R. Wybom, A. J. Wallace, T. J. Stillman, L. K. Black, A. B. Fielding, M. Hisakado, P. J. Artymiuk, and J. Green. 2000. Structure-function relationships of a novel bacterial toxin, hemolysin E. The role of $\alpha_G$. J. Biol. Chem. 275:41150-41155).

The HlyE family of proteins typically causes hemolysis in target cells. Hemolytically active or inactive HlyE family members can both be used with the disclosed teachings. For example, it is known that mutation of the hlyE gene can reduce or eliminate hemolytic activity. For example, loss of hemolytic activity has been reported when hlyE is mutated such that amino acid substitutions occur at positions 180, 185, 187, and 193. Specifically, G180V, V185S, A187S, and I193S result in a loss of hemolytic activity from a HlyE protein expressed from a mutated hlyE gene.

The present disclosure utilizes the export characteristics of the HlyE family of proteins to produce a protein export system. For example, fusion proteins comprising any member of the HlyE family and a protein of interest are disclosed. More specifically, fusion proteins comprising *S. Typhi* ClyA and a protein of interest are disclosed. As discussed below, ClyA-containing fusion proteins are exported from the bacterial host cell and into the surrounding medium. This feature of the expression system comprising an export protein::protein of interest fusion protein component which facilitates production of the protein of interest and exportation of the export protein::protein of interest fusion protein. In preferred embodiments, variants of HlyE family members lacking or having reduced hemolytic activity are used as the export proteins.

B. Cytolysin A (ClyA) Protein Export System

A preferred embodiment of the present disclosure relates to the use of the *S. Typhi* Cytolysin A (ClyA) protein in a protein export system. ClyA from *S. Typhi* was first described by Wallace et al. who also reported the crystal structure for the homologous hemolysin from *E. coli* (Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276). This hemolysin has been described previously and variously referred to as ClyA, HlyE, or SheA. To avoid confusion, the *E. coli* hemolysin is referred to herein as HlyE and is encoded by hlyE. Also for clarity, the *S. Typhi* hemolysin is referred to herein as ClyA, which is encoded by clyA.

The crystal structure of ClyA in *E. coli* has been resolved (Wallace et al, 2000). The unique structure can be roughly divided into several domains, a head domain, a body domain and a tail domain. The body domain consists of a bundle of helixes (A, B, C, D, F). The tail domain is a helix G which extends to half the length of the body. The head domain consists of a short β hairpin (β-tongue) and two small helicies (D and E), each flanking the β-tongue. Wallace et al suggested that the β-tongue might be critical for pore formation and hence for the hemolytic activity (Wallace et al, 2000). Through site directed mutagenesis, Oscarsson et al found many regions of ClyA that were important for the hemolytic activity (Oscars son et al, 1999). But their mutagenesis strategy could have distorted the structure of ClyA and affected the export of ClyA without actually abolishing hemolytic activity per se.

An approximately 1 kb clyA gene was cloned from *S. Typhi* CVD 908-htrA for use in a protein export system. The ClyA protein is exported from both *E. coli* and *S. Typhi* and it is capable of exporting passenger proteins that have been genetically fused to the 3'-terminus of the clyA open reading frame. Passenger protein referred to herein is also referred to as a protein of interest. It is demonstrated that the proper folding of these fusion proteins occurs such that the inherent biological activity of the domains involved is maintained.

The nucleotide and amino acid sequence for the isolated *S. Typhi* clyA gene and ClyA protein are provided as SEQ ID NO:21 and SEQ ID NO:2, respectively. The nucleotide sequence of SEQ ID NO:21 is the wild-type nucleotide sequence recovered from *Salmonella* serovar *Typhi* strain Ty2. A synthetic codon-optimized version of the *S. Typhi* clyA gene, as described and utilized herein, is provided in SEQ ID NO:33. Other HlyE family members that may be utilized as export proteins herein are also available and known to those of ordinary skill in the art. The family members include a second *S. Typhi* cytolysin A (the clyA gene is set forth in SEQ ID NO:22 and it is available under GENBANK Accession No. AJ313034); *Salmonella paratyphi* cytolysin A (the clyA gene sequence for cytolysin A is set forth in SEQ ID NO:23 and it is available under GENBANK Accession No. AJ313033); *Shigella flexneri* truncated HlyE (the hlyE gene sequence is set forth in SEQ ID NO:24 and it is available under GENBANK Accession No. AF200955); *Escherichia coli* HlyE (the hlyE gene sequence is set forth in SEQ ID NO:25 and it is available under GENBANK Accession No. AJ001829).

C. Non-Hemolytic Variants of HlyE Family Members

As indicated above, the HlyE family of proteins typically causes cytolysis of target cells, including hemolysis of erythrocytes. Because cytolysins/hemolysins may be considered to be virulence factors, the present invention also encompasses variants of HlyE family members that have been mutated such that they lack, or have reduced, hemolytic activity. The ability of these variants to be exported from a bacterial cell producing them, alone or in the context of fusion to a protein of interest, has been maintained. Thus, the non-hemolytic variants of HlyE family members have reduced or no hemolytic activity, and yet are fully functional in the protein export systems of the present invention.

The non-hemolytic variants of HlyE family members may have any number of genetic mutations in the polynucleotide sequence encoding them such that the hemolytic activity of the variant is either reduced or completely abolished. In order to preserve other activities and functions of the variants, it is preferably that the fewest number of mutations be made to the coding sequence of the variants. In particular, mutations may be made to the coding sequence of a HlyE family member such that only 1, 2, 3, 4, 5, 6, 7, 8, 9, 10, 11, 12, 13, 14, 15 or more amino acid changes result. The amino acid changes include deletions, additions and substitutions. The amino acid substitutions may be conservative or non-conservative amino acid substitutions. The mutations may be made to any region of the polynucleotide encoding the variant, but in preferred embodiments the mutation(s) result in amino acid substitutions in the beta-tongue or the small helix E.

As indicated above, the hemolytic activity of the non-hemolytic variants of HlyE family members of the present invention may be either reduced or completely abolished. Where the hemolytic activity is reduced, the reduction is about 5, 10, 15, 20, 25, 30, 35, 40, 45, 50, 55, 60, 65, 70, 75, 80, 85, 90, 95, 96, 97, 98 or 99% reduction in activity compared to the wild-type family member from which the variant was derived. As used herein, a non-hemolytic variant of an HlyE family member of the present invention having "substantially reduced" hemolytic activity is a variant exhibiting a reduction of at least about 90, 91, 92, 93, 94, 95, 96, 97, 98 or 99% of the hemolytic activity of the wild-type protein from which it was derived. Specific hemolytic activity may be measured by quantifying the release of hemoglobin from erythrocytes, as described by Sansonetti et al. 1986. Infect. Immun. 51: 461-9.

The skilled artisan will understand that while each of the variants of the present invention will retain the ability to be exported from the cell in which it is produced, either alone or as a fusion with a protein of interest, a small reduction in the ability of the variant to be exported may be acceptable. Therefore the present invention also encompasses those variants having reduced or abolished hemolytic activity, along with a reduction in the ability to be exported of about 1, 2, 3, 4, 5, 10, 15, 20, 25, 30, 35, 40, 45 or 50% in comparison to the wild-type family member from which the variant was derived.

In a preferred embodiment, the non-hemolytic variant of an HlyE family member is a non-hemolytic variant of the *S. Typhi* ClyA protein. Such *S. Typhi* ClyA variants include those having 1, 2, 3, 4, 5, 6, 7, 8, 9, 10, 11, 12, 13, 14 15 or more amino acid changes. Further, such *S. Typhi* ClyA variants have a reduction in hemolytic activity of about 5, 10, 15, 20, 25, 30, 35, 40, 45, 50, 55, 60, 65, 70, 75, 80, 85, 90, 95, 96, 97, 98 or 99% compared to the wild-type *S. Typhi* ClyA protein. Furthermore, such *S. Typhi* ClyA variants may have a reduction in the ability to be exported of about 1, 2, 3, 4, 5, 10, 15, 20, 25, 30, 35, 40, 45 or 50% in comparison to the wild-type *S. Typhi* ClyA protein.

The skilled artisan will understand that the mutations may be introduced into the sequence encoding *S. Typhi* ClyA using a variety of techniques, including commercially available kits for site directed mutagenesis. The variants of the present invention may be produced by introducing mutations into the sequence encoding *S. Typhi* ClyA alone or into a sequence encoding a fusion protein comprising *S. Typhi* ClyA genetically fused to a sequence encoding a protein of interest or a reporter protein. In one embodiment, the sequence encoding *S. Typhi* ClyA is fused to a sequence encoding green fluorescent protein (GFPuv) to produce a clyA::gfpuv genetic fusion. It is well known that GFPuv will not fluoresce if it is fused to upstream domains that do not fold correctly. Therefore, a clyA::gfpuv genetic fusion may be used to screen for non-hemolytic, fluorescent, correctly-folded mutants, likely to be correctly exported.

In addition to the non-hemolytic variants of HlyE family members, the present invention includes fusions proteins comprising a wild-type HlyE family member linked to a protein of interest. Due to the innate characteristics of some proteins of interest, simply creating a fusion protein comprising a wild-type HlyE family member and a protein of interest can result in the production of a fusion protein that is exported from the cell in which it is produced, yet that has reduced or abolished hemolytic activity. In one embodiment, such a fusion protein comprises the *S. Typhi* ClyA protein linked to the anthrax toxin PA83 protein. The ClyA::PA83 protein fusion retains the ability to be exported from the cell in which it is produced, yet has reduced hemolytic activity.

Examples of preferred non-hemolytic variants of the *S. Typhi* ClyA protein of the present invention include those variants shown in Table 1 that have a single mutation in the indicated position. The noted "position" and wild-type sequence ("wt") in Table 1 corresponds to the amino acid sequence of the *S. Typhi* ClyA polypeptide shown in SEQ ID NO:2. The "domain" is the particular domain of the *S. Typhi* ClyA polypeptide. The single letter amino acid substitutions in Table 1, and used herein, are: Alanine—A; Arginine—R; Asparagine—N; Aspartic acid—D; Cysteine—C; Glutamic acid—E; Glutamine—Q; Glycine—G; Histidine—H; Isoleucine—I; Leucine—L; Lysine—K; Methionine—M; Phenylalanine—F; Proline—P; Serine—S; Threonine—T; Tryptophan—W; Tyrosine—Y; Valine—V.

TABLE 1

| clone | position | wt | mutation | domain | SEQ ID NO: |
|---|---|---|---|---|---|
| M133 | 109 | A | T | αC | |
| M165 | 109 | A | V | αC | |
| M188 | 116 | L | Q | αC | |
| M187 | 148 | L | P | αC | |
| M179 | 163 | S | C | turn between αC & αD | |
| M103 | 195 | S | N | β tongue | |
| M30 | 198 | I | N | αE | 30 |
| M128 | 199 | A | D | αE | |
| M135 | 204 | E | K | αE | |
| M182 | 204 | E | D | αE | |
| M109 | 205 | G | D | αE | |
| M64 | 207 | L | R | αF | |
| M185 | 215 | L | P | αF | |
| M163 | 225 | L | S | αF | |
| M176 | 229 | V | L | αF | |
| M150 | 281 | M | K | αG | |
| M171 | 284 | T | P | αG | |
| M148 | 285 | C | W | αG | |

The C285W mutation of *S. Typhi* ClyA disrupts a naturally occurring intramolecular cysteine bridge that prevents oligomerization of ClyA required for cytolytic pore formation.

Export Protein Expression Vectors

The protein export system described herein can be used to express and export a wide variety of fusion proteins comprising an export protein and a protein of interest. The export protein is selected from the HlyE family of proteins, and the variants thereof described herein. In one embodiment, the protein of interest is encoded by a gene of interest. The gene of interest can be foreign to the bacteria containing the protein export system or it can be a gene that is endogenous to the bacteria. Typically, an export protein::protein of interest fusion protein construct is present in an expression cassette, which in turn is present in an expression vector. Each of these units is discussed below.

Expression Vectors

The protein export system utilizes an expression vector to facilitate the recombinant production of the protein of interest. Typically the expression vector will comprise an origin of replication and other structural features that control and regulate the maintenance of the expression vector in the host cell. By definition, the term "expression vector" refers to a plasmid, virus or other vehicle known in the art that has been manipulated by insertion or incorporation of the expression cassette comprising the export protein::protein of interest fusion protein expression cassette. An example of an expression vector system which teaches expression vectors that confer plasmid stability at two independent levels as described in Galen, et al., Immun. 67:6424-6433 (1999) and in U.S. patent application Ser. No. 09/204,117, filed Dec. 2, 1998, now U.S. Pat. No. 6,413,768, and Ser. No. 09/453,313, filed Dec. 2, 1999, now U.S. Pat. No. 6,703,233, which are hereby incorporated by reference in their entirety.

Exemplary expression vectors that may be utilized include those shown in FIG. 1 which includes pSEC84, pSEC84bla, pSEC84sacB, pSEC84toxC, pSECgfpuv, pSEC92gfpuv, pSEC93gfpuv, pSEC92M30gfpuv, pGEN222A3S, and pGEN222A3S-ClyA-PA83. Additional vectors include the lower copy number plasmids derived from pSC101, including pGEN206 and pSEC10, and fusions thereof such as pSEC91-83 and pSEC10-835 (Galen et al. *Immunol. Cell Biol.* May 5, 2009, pp 1-13; Galen et al. *J. Infect. Dis.* 119:326-335 (2009)). The cassette technology allows any replicon to be adapted for expression of ClyA variants because the clyA fusion cassette (comprising the ompC promoter, clyA, and downstream fusion partner) is completely self-contained and requires only a plasmid replicon to be successfully used in any permissive bacterial background. Thus, any of the vectors disclosed herein and any other vector known in the art to be useful for the purposes contemplate herein may be used. Furthermore, each of the expressions vectors disclosed herein may be used as provided. However, the skilled artisan will understand that these expression vectors may also be used as a backbone vector from which the sequence encoding the export protein, the sequence encoding the protein of interest, or the sequence encoding the export protein:protein of interest fusion protein (when they are present) can be removed and replaced by a different sequence encoding these elements. For example the sequence encoding GFPuv in pSEC93gfpuv can be removed and replaced by a sequence encoding an antigen of interest.

Export Protein-Fusion Protein Expression Cassettes

The protein export system described herein can be used to express and export a wide variety of fusion proteins comprising an export protein and a protein of interest. The protein of interest is encoded by the protein of interest coding sequence which is also the gene of interest. The gene of interest can be foreign to the bacteria containing the protein export system or it can be a gene that is endogenous to the bacteria. The protein of interest can range from a single amino acid to proteins several times the size of the export protein molecule. More preferably, the protein of interest can range from ten amino acids to two times the size of the export protein. It is preferable that the size of the protein of interest be such that it not interfere with the ability of the export protein to be exported entirely out of the bacterium. Exemplary proteins of interest are from 0 kDa to at least 50 kDa in mass. Greater masses, and thus longer proteins may also be used as proteins of interest. For example, the proteins of interest may have a mass of 55 kDa, 60 kDa, 65 kDa, 70 kDa, 75 kDa, 80 kDa, 85 kDa, 90 kDa, 95 kDa, 100 kDa, or larger.

Alternatively, the protein of interest can consist of 1 to 1000 amino acids, or more. For example, the protein of interest may have 10, 20, 30, 40, 50, 60, 70, 80, 90, 100, 150, 200, 250, 300, 350, 400, 450, 500, 550, 600, 650, 700, 750, 800, 850, 900, 950, 1000 amino acids, or more.

Typically, the gene of interest to be expressed is present in an expression cassette. An expression cassette will typically contain suitable structural features, such as a promoter, terminator, etc., to permit transcription of the gene of interest.

Polynucleotide sequences encoding an export protein::protein of interest fusion protein (also known as "export protein::protein of interest fusion protein coding sequences") can be operatively linked to expression control sequences to form an expression cassette. The term "operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, transcription terminators, optimized ribosome binding sequences, a start codon (i.e., ATG) in front of a protein-encoding gene, the correct reading frame of that gene to permit proper translation of mRNA, and stop codons. The term "control sequences" is intended to include, at a minimum, components whose presence can influence expression, and can also include additional components whose presence is advantageous, for example, leader sequences. Expression control sequences can include a promoter.

A "promoter" is the minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the export protein::protein of interest fusion protein coding sequence. Both constitutive and inducible promoters are useful with the disclosed methods. The expression of export protein::protein of interest fusion protein coding sequences can be driven by a number of promoters. Although the endogenous promoter of an export protein can be utilized for transcriptional regulation of the expression cassette, preferably, the promoter is a foreign regulatory sequence. An example of an inducible endogenous promoter is the ompC promoter which can be used to drive transcription of the expression cassette.

Promoters useful in the invention include both constitutive and inducible natural promoters as well as engineered promoters. A preferred inducible promoter should 1) provide low expression in the absence of the inducer; 2) provide high expression in the presence of the inducer; 3) use an induction scheme that does not interfere with the normal physiology of the host cell; and 4) have little or no effect on the expression of other genes. Examples of inducible promoters include those induced by chemical means. Those of skill in the art will know other promoters, both constitutive and inducible.

The particular promoter selected should be capable of causing sufficient expression to result in the production of an effective amount of the export protein::protein of interest fusion protein. The effective amount of export protein::protein of interest fusion protein can vary depending on the goal of the expression. The promoters used in the vector constructs of the present disclosure can be modified, if desired, to affect their control characteristics.

The export protein::protein of interest fusion protein comprising the export protein and the protein of interest can further comprise purification tags engineered into the expression cassette to be expressed as a part of the export protein::protein of interest fusion protein. The tag is chosen to facilitate purification of the export protein::protein of interest fusion protein and/or the protein of interested produced by the described methods. For example, a plurality of histidine residues can be engineered into the C-terminal portion or N-terminal portion of the protein of interest to facilitate protein purification. It is preferable that the introduction of the tag minimizes improper folding of the protein of interest.

In addition to the polyhistidine tag, there are a number of other protein tags that can be used to facilitate protein purification. For example, antigenic tags such as the maltose binding protein tag, a c-myc epitope tag, a green fluorescent protein tag, a luciferase tag, a beta-galactosidase tag, a polyhistidine tag, or any other suitable protein expression tag that can be used with the described system.

The export protein::protein of interest fusion protein comprising the export protein and the protein of interest can further comprise additional features to facilitate the use of the expressed and exported protein. For example, protease recognition sites can be engineered between various components of export protein::protein of interest fusion protein, including, if applicable, the tags described above, to promote the separation of the components of the export protein::protein of interest fusion protein. For example, a protease recognition site can be introduced between the export protein and protein of interest sequences in the expression cassette. Also a protease recognition site can be introduced between the tag and the protein of interest sequences in the expression cassette. These protease recognition sites facilitate the separation of the export protein from the protein of interest.

The export protein::protein of interest fusion protein is typically arranged such that the protein of interest is connected to the carboxy terminus of the export protein. However, the skilled artisan will understand that, depending on the identity of the export protein and the protein of interest, the fusion protein may be constructed such that the export protein is connected to the carboxy terminus of the protein of interest.

Optionally, a selectable marker may be associated with the expression cassette. As used herein, the term "marker" refers to a gene encoding a trait or a phenotype that permits the selection of, or the screening for, a host cell containing the marker. The marker gene may be an antibiotic resistance gene whereby the appropriate antibiotic can be used to select for transformed host cells from among cells that are not transformed or the marker gene may be some other drug resistance gene. Examples of suitable selectable markers include adenosine deaminase, dihydrofolate reductase, hygromycin-B-phosphotransferase, thymidine kinase, xanthine-guanine phospho-ribosyltransferase, glyphosphate and glufosinate resistance and amino-glycoside 3'-O-phosphotransferase II (kanamycin, neomycin and G418 resistance). Those of skill in the art will know other suitable markers that can be employed with the disclosed teachings.

An example of an expression vector is shown in FIG. 1. In FIG. 1A, the pSEC84 expression vector is shown. The nucleotide sequence of the pSEC84 vector can be found at SEQ ID NO:1. The amino acid sequence of ClyA encoded by the clyA gene is found at SEQ ID NO:2.

Each vector shown in FIGS. 1A-D comprises a promoter ($P_{ompC}$—a modified osmotically controlled ompC promoter from *E. coli*), an export protein (clyA), an origin of replication, a transcriptional terminator (T1), a passive partitioning function (par), resistance to kanamycin (aph), a post-segregational killing system (hok-sok), and an active partitioning system (parA). It should be noted that these vector components are merely exemplary of a single embodiment of the disclosed system.

FIG. 1B illustrates the pSEC84bla expression vector. This expression vector contains the same features as the pSEC84 vector and further comprises a export protein::protein of interest fusion protein construct. Specifically, the bla gene encoding β-lactamase was cloned into the pSEC84 vector at the Nhe I site at position 1426 of the parent vector. Other fusion constructs are shown in FIG. 1C (pSEC84sacB) and FIG. 1D (pSEC84gfpuv).

Figure 5:
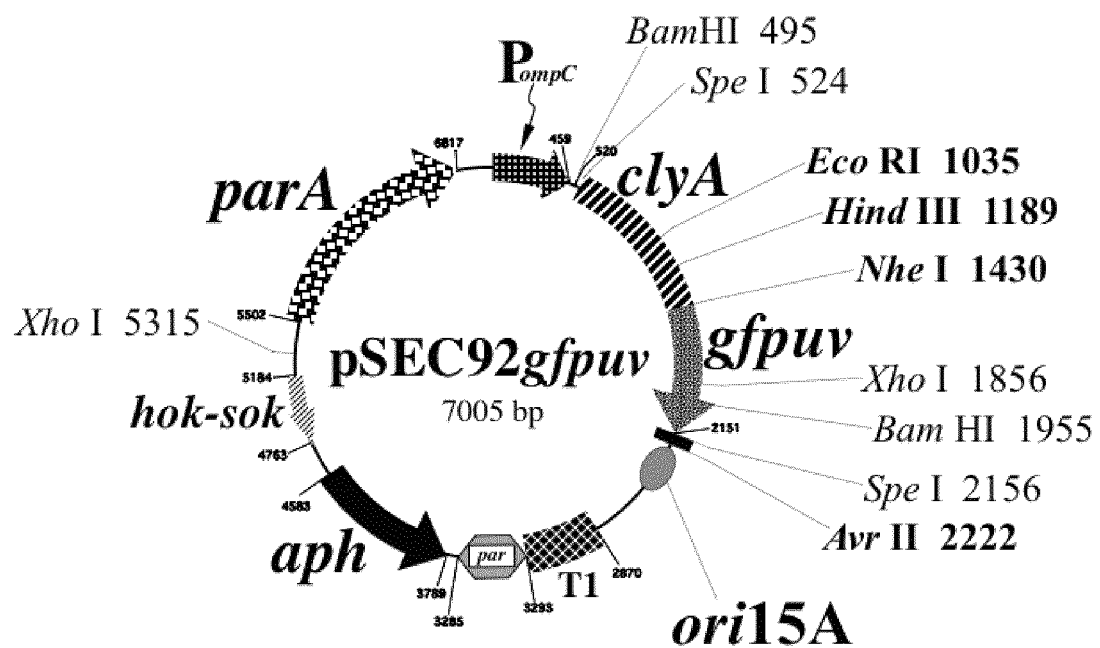
FIG. 5 shows the expression plasmid pSEC92gfpuv. pSEC92gfpuv has an insertion of a codon optimized *Salmonella Typhi* clyA sequence. In a further derivation of this expression plasmid, pSEC93gfp has the same genetic structure as pSEC92gfpuv except that it has three point mutations, I198→N, A199→D, E204→K in the clyA sequence.

FIG. 5 illustrates the additional vector pSEC92gfpuv containing the coding sequence for *S. Typhi* ClyA wherein the codons have been optimized for expression in prokaryotes, including but not limited to the genera *Salmonella* and *Escherichia*. It is appreciated by one skilled in the art that codon optimization of foreign genes introduced into a bacterial host allows for high level expression of the encoded foreign protein of interest. The present invention describes the genetic fusion of codon-optimized clyA to gfpuv encoding the green fluorescent protein GFPuv, encoded by the expression plasmid pSEC92gfpuv. The nucleotide sequence of codon-optimized clyA is set forth in SEQ ID NO:33. pSEC92gfpuv is particularly useful in the generation and testing of different point mutations within the clyA gene. It is well known that GFPuv will not fluoresce if it is fused to upstream domains that do not fold correctly. Therefore, a clyA::gfpuv genetic fusion may be used to screen for point mutations in the clyA coding region that result in non-hemolytic, fluorescent, correctly-folded mutants, likely to be correctly exported. pSEC93gfpuv is derived from pSEC92gfpuv, and encodes codon optimized *S. Typhi* ClyA with the addition of three engineered point mutations in the clyA coding region: I198N, A199D and E204K, fused to the coding region for green fluorescent protein (gfpuv).

Genes of Interest

The protein export system disclosed herein can be used with a variety of genes of interest. In one embodiment, the gene of interest encodes a desired protein. Any protein amenable to recombinant bacterial expression can be used with the disclosed export system. The gene of interest can encode for any polypeptide such as, for example, a mammalian polypeptide such as an enzyme, an enzyme inhibitor, a hormone, a lymphokine, a plasminogen activator, or any other protein of interest. The gene of interest can encode a eucaryotic gene, a procaryotic gene, a plant gene, or viral gene of interest.

One advantage of the disclosed system is that it provides a method by which proteins that were toxic to a host bacterium can now be expressed. For example, recombinant expression of certain proteins is complicated or impossible when the expressed protein is not exported from the host bacterial cell. With the methods disclosed herein, one of ordinary skill in the art could express a previously unexpressible or underexpressed protein to produce the desired protein in usable quantities.

In another embodiment, the gene of interest is an immunogenic antigen-encoding gene, and the protein of interest is an antigen which may be a protein or antigenic fragment thereof from any pathogen, such as viral pathogens, bacterial pathogens, and parasitic pathogens. Alternatively, the gene of interest may be a synthetic gene, constructed using recombinant DNA methods, which encode antigens or parts thereof from viral, bacterial, parasitic pathogens, or another antigen of interest. These pathogens can be infectious in humans, domestic animals or wild animal hosts.

Examples of particular viral pathogens, from which the viral antigens are derived, include, but are not limited to, Orthomyxoviruses, such as influenza virus; Retroviruses, such as Rous sarcoma virus (RSV) and simian immunodeficiency virus (SIV), Herpesviruses, such as Epstein Barr virus (EBV); cytomegalovirus (CMV) or herpes simplex virus; Lentiviruses, such as human immunodeficiency virus; Rhabdoviruses, such as rabies; Picomoviruses, such as poliovirus; Poxviruses, such as vaccinia; Rotavirus; and Parvoviruses.

Examples of immunogenic antigens from viral pathogens include the human immunodeficiency virus antigens Nef, p24, gp120, gp41, Tat, Rev, and Pol. Additional examples of antigens include the T cell and B cell epitopes of gp120, the hepatitis B surface antigen, rotavirus antigens, such as VP4, VP6, and VP7, influenza virus antigens such as hemagglutinin or nucleoprotein, and herpes simplex virus thymidine kinase. The nucleic acid and amino acid sequences for each of these virus antigens are well known in the art and readily available.

Bacterial pathogens, from which the bacterial antigens can be derived, include, but are not limited to, *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., *Clostridium* spp., *Yersinia* spp., and *Borellia burgdorferi*.

Examples of immunogenic antigens of bacterial pathogens include, but are not limited to, the *Shigella sonnei* form 1 antigen, the O-antigen of *V. cholerae* Inaba strain 569B, immunogenic antigens of enterotoxigenic *E. coli*, such as the CFA/I fimbrial antigen, and the nontoxic B-subunit of the heat-labile toxin, pertactin of *Bordetella pertussis*, adenylate cyclase-hemolysin of *B. pertussis*, Protective Antigen (PA83) of anthrax toxin from *Bacillus anthracis* and fragment C of tetanus toxin of *Clostridium tetani*, F1 and/or V antigen from *Yersinia pestis, Shigella* enterotoxins 1 and 2 (i.e., ShET1, ShET2) of *Shigella* spp., the EAEC proteins described in U.S. Pat. No. 7,090,850, enterotoxigenic *Escherichia coli* fimbriae, and the *E. coli* surface antigens (CSs) or colonization factor antigens (CFAs), enterotoxigenic *Escherichia coli* (ETEC) fimbriae including enterotoxigenic *Escherichia coli* (ETEC) CS4 fimbriae (specifically any of csaA, csaB, csaC, csaE and/or csaD, which is described further in U.S. Pat. No. 6,902,736).

Examples of immunogenic antigens of parasitic pathogens, from which the parasitic antigens can be derived, include, but are not limited to, *Plasmodium* spp., *Trypanosome* spp., *Giardia* spp., *Boophilus* spp., *Babesia* spp., *Entamoeba* spp., *Eimeria* spp., *Leishmania* spp., *Schistosome* spp., *Brugia* spp., *Fascida* spp., *Dirofilaria* spp., *Wuchereria* spp., and *Onchocerea* spp.

Examples of immunogenic antigens of parasitic pathogens include, but are not limited to, the circumsporozoite antigens of *Plasmodium* spp., such as the circumsporozoite antigen of *P. bergerii* or the circumsporozoite antigen of *P. falciparum*; the merozoite surface antigen of *Plasmodium* spp.; the galactose specific lectin of *Entamoeba histolytica*, gp63 of *Leishmania* spp., paramyosin of *Brugia malayi*, the triose-phosphate isomerase of *Schistosoma mansoni*; the secreted globin-like protein of *Trichostrongylus colubriformis*; the glutathione-S-transferase of *Frasciola hepatica, Schistosoma bovis* and *S. japonicum*; and KLH of *Schistosoma bovis* and *S. japonicum*.

In another embodiment, the gene of interest can encode a therapeutic agent, such as, but not limited to, tumor-specific, transplant, or autoimmune antigens or parts thereof. Alternatively, the gene of interest can encode synthetic genes, which encode for tumor-specific, transplant, or autoimmune antigens or parts thereof.

Examples of tumor specific antigens include prostate specific antigen, TAG-72 and CEA, MAGE-1 and tyrosinase. Recently it has been shown in mice that immunization with non-malignant cells expressing a tumor antigen provides a vaccine-type effect, and also helps the animal mount an immune response to clear malignant tumor cells displaying the same antigen.

Examples of transplant antigens include the CD3 receptor on T cells. Treatment with an antibody to CD3 receptor has been shown to rapidly clear circulating T cells and reverse most rejection episodes.

Examples of autoimmune antigens include IAS chain. Vaccination of mice with an 18 amino acid peptide from IAS chain has been demonstrated to provide protection and treatment to mice with experimental autoimmune encephalomyelitis.

Alternatively, the gene of interest can encode immunoregulatory molecules. These immunoregulatory molecules include, but are not limited to, growth factors, such as M-CSF, GM-CSF; and cytokines, such as IL-2, IL-4, IL-5, IL-6, IL-10, IL-12 or IFN-gamma. Recently, localized delivery of cytokines to tumor tissue has been shown to stimulate potent systemic immunity and enhanced tumor antigen presentation without producing a systemic cytokine toxicity.

Stabilized Plasmid-Based Expression Systems

Bacterial expression systems, by design, typically utilize expression vectors to harness and exploit the protein synthesis machinery of a bacterial host cell to produce a protein of interest. Protein expression levels can often be increased by using high copy number plasmids, or high copy number expression vectors, with the host cells. As discussed above, the introduction of a high copy number expression vector into a bacterial host cell, however, places certain metabolic stresses on the host cell that can cause the host cell to expel the expression vector and thus reduce protein expression levels.

Often overlooked in expression vector engineering is the effect high copy number expression vectors frequently exert on the fitness of the host cell in which the expression vector is introduced. The burden placed upon host bacterial cells carrying multicopy plasmids is the cumulative result of a metabolic cascade. The cascade is triggered by the replication and maintenance of expression vectors (see Bailey, J. E., Host-vector interactions in *Escherichia coli*, p. 29-77. In A. Fiechter (ed.), Advances in Biochemical Engineering. Biotechnology. Springer-Verlag, Berlin (1993), Glick, B. R., Biotechnol. Adv. 13:247-261 (1995), and Smith & Bidochka. Can. J. Microbiol. 44:351-355 (1998)). The cascade is also triggered by transcription and translation of the various expression vector-encoded functions, including the protein of interest. Mechanisms such as those described above explain the observation that plasmid-bearing bacteria grow slower than plasmid-less bacteria. These mechanisms can also explain the observation that growth rate decreases as copy number increases.

Growth rates of recombinant organisms containing expression vectors have been observed to decrease as the expression of a gene of interest increases. The decrease in growth may trigger the induction of various cellular proteases that can degrade the expressed recombinant protein of interest. Reduced growth rate is therefore the inevitable consequence of metabolic burden, which in turn is the cumulative result of a number of physiological perturbations. For example, physiological perturbations result from the expression and accumulation of the protein of interest inside the host bacterium.

This accumulation can be harmful to the viability of the host organism and thus a negative selection pressure.

Because metabolic burdens such as those discussed above create a selective pressure for loss of resident expression vectors in the absence of selection, significant loss of expression vectors from the host cell can occur after the host cell has been transformed with the expression vector containing the gene of interest. Spontaneous plasmid loss removes any metabolic burden from the host cell and allows plasmid-less host cell to quickly outgrow the population of plasmid-bearing host cell. The overgrowth of host cells that do not contain and thus do not express the protein of interest reduces overall protein production levels. Therefore, host cells that are not genetically constrained to maintain expression vectors directing the synthesis of high levels of a given protein of interest may produce significantly less protein.

There are a number of means by which this metabolic stress can be reduced. Controlled expression of a protein of interest from multicopy expression vectors represents one solution for synthesis of high levels of protein of interest within host cells. This solution is one embodiment with which to practice the disclosed methods. Utilization of inducible promoters, for example, is one method by which expression from an expression vector can be controlled. Such inducible promoters are discussed in the expression cassette section of this disclosure.

Another embodiment of the methods disclosed herein relates to a plasmid-based expression system engineered to permit the stable expression of high levels of one or more proteins throughout a growing population of cells. Preferably, a stable expression vector is one that perpetuates the expression vector as the host cell replicates. Expression vectors that confer plasmid stability at two independent levels have recently been described in Galen, et al., Immun. 67:6424-6433 (1999) and in U.S. patent application Ser. No. 09/204,117, filed Dec. 2, 1998, now U.S. Pat. No. 6,413,768, and Ser. No. 09/453,313, filed Dec. 2, 1999, now U.S. Pat. No. 6,703,233, both of which are hereby incorporated by reference in their entirety.

In this embodiment, partition functions can be incorporated into an expression vector to enhance the inheritance of the plasmid as a given bacterium or host cell grows and subsequently divides. In rare cases where a daughter cell does not inherit at least one copy of the expression vector, a latent post-segregational killing system becomes activated and removes this bacterium or host cell from the growing population through cell lysis.

D. Host Organisms

A number of species of bacteria are suitable for use with the teachings disclosed herein. Preferably, a suitable bacterial species will be capable of protein export such that the gene of interest can be suitably transcribed such that the protein of interest is translated and exported out of the bacteria. In one embodiment of the invention, the bacteria are administered to an animal, and thus the protein of interest must be exported out of the bacteria into the animal. Invasive and non-invasive bacteria may be used. Examples of some invasive bacteria include *Clostridium* spp. (such as *C. difficile*), *Shigella* spp., *Listeria* spp., *Rickettsia* spp., and enteroinvasive *Escherichia coli*. Specific embodiments utilize *Vibrio, Salmonella, Shigella* and/or *Clostridium* species. Non-limiting exemplary embodiments include but are not limited to *S. Typhi*, such as *S. Typhi* CVD 908 having an htrA mutation, *E. coli*, such as enterotoxigenic *E. coli* (ETEC) or enteroaggregative *E. coli* (EAEC), *Vibrio cholerae, Shigella flexneri* 2a, and *Clostridium difficile*.

The particular *Salmonella* strain employed with the disclosure below is not critical. Examples of *Salmonella* strains which can be employed in the present invention include *S. Typhi* (ATCC No. 7251) and *S. Typhimurium* (ATCC No. 13311). Attenuated *Salmonella* strains are preferably used in the present invention and include *S. Typhi* aroAaroD (Hone et al, Vacc., 9:810-816 (1991)), *S. Typhi* CVD 908-htrA and *S. Typhimurium* aroA mutant (Mastroeni et al, Micro. Pathol., 13:477-491 (1992))). Alternatively, new attenuated *Salmonella* strains can be constructed by introducing one or more attenuating mutations as described for *Salmonella* spp. above.

The host organism may also be a virus, such as: (i) a phage; (ii) a double-stranded DNA virus, such as an adenovirus, a herpesvirus, or a poxvirus; (iii) a single-stranded DNA virus, such as a Parvovirus; (iv) a double-stranded RNA virus, such as a reovirus; (v) a single-stranded RNA virus, such as a Picornavirus, a Togavirus, a Orthomyxovirus; or a Rhabdovirus, (vi) a retrovirus; or (vii) a tobacco mosaic virus.

E. Bioreactors

The protein export system described herein is suited for use with bioreactors and similar devices that facilitate the growth of bacteria and the harvesting or use of a desired product or protein of interest. Traditionally there are five stages for recovery of biomolecules from the prior art bioreactors: pre-treatment, solid/liquid separation, concentration, purification, and formulation. There can be a wide range of operations available within each stage. These ranges of operations for each stage are as follows: Pre-treatment: cell disruption, stabilization, sterilization, pasteurization, and flocculation; Solid/liquid Separation: filtration, sedimentation, and centrifugation; Concentration: membranes, precipitation, evaporation, extraction, and freeze concentration; Purification: precipitation, extraction, diafiltration, adsorption, and chromatography; and Formulation: drying, prilling, extrusion, granulation, and tabletting.

In bioreactors where the bacteria do not export the desired product out of the bacteria, one has to scale up the bacteria, induce the bacteria to produce the desired product, and then lyse the bacteria to release the contents. Typically this disruption is performed in the same medium in which the bacteria were grown. One can use a homogenizer or bead mill to mechanically disrupt the bacteria. For non-mechanical disruption, one can use heat shock (which may destroy proteins), detergents, solvents, sequestrants, and enzymes. (Krijgsman, "Releases of Intracellular Components", pp. 27-42, in Product Recovery in Bioprocess Technology, publisher Butterworth-Heinemann Ltd, Oxford, England, 1992).

After the bacteria are disrupted one separates the solid particulates from the fluids (solid/liquid separation). The desired product is usually in the liquid, which one then has to concentrate. Then one extracts the desired product from the concentrated liquid.

Factors which affect separation of the desired product from either the undesired solids or liquids are size, diffusivity, ionic charge, solubility, and density. For size-dependent separation, one can use microfilters, cloth and fiber filters, ultrafiltration, screens/strainers, and gel chromatography. For diffusivity-dependent separation, one can use reverse osmosis and dialysis. Ion exchange chromatography is used for ionic charge-dependent separation. To separate the desired product based on its solubility, one can use solvent extractions. For density-dependent separation, one can use ultracentrifuges, centrifuges, and gravity sedimentation. (Krijgsman, "Downstream Processing in Biotechnology", pp. 2-12, in Product Recovery in Bioprocess Technology, publisher Butterworth-Heinemann Ltd, Oxford, England, 1992).

One advantage of using the disclosed system is that a population of recombinant bacterial host cells can be transformed with an expression vector comprising the disclosed protein export system and that population of bacterial host cells can be maintained in culture and used to produce protein without having to harvest and lyse the bacterial host cells. The culturing of bacterial host cells and the harvesting of the culture medium containing the recombinantly expressed protein of interest can be performed in any type of bioreactor.

There are various types of bioreactors but the family of devices can be divided to two main categories, "free floating" and "bed" bioreactors. In "free floating" bioreactors, the bacteria are floating freely within the media. Examples of "free floating" bioreactors are conventional stirred tank bioreactors, bubble column, airlift loop, multi-purpose tower bioreactors, liquid impelled loop bioreactors, and pumped tower loop bioreactors. An example of the "bed"-type bioreactor is the packed bed bioreactor. In a "bed"-type bioreactor, the bacteria are attached to beads, a membrane, or other solid support. A hybrid type of bioreactor can be produced using a fluidized bed bioreactor where the bacteria are attached to beads or other support but can float in the media. (Mijnbeek, "The Conventional Stirrer Tank Reactor" pp. 39-74; Mijnbeek, "Bubble Column, Airlift Reactors, and Other Reactor Designs" pp. 75-114; Geraats, "An Introduction to Immobilized Systems" pp 115-124; all in "Operational Modes of Bioreactors", publisher Butterworth-Heinemann Ltd, Oxford, England, 1992).

Using the protein export system described herein with a "bed" bioreactor avoids the step of pre-treatment and solid/liquid separation because the desired protein of interest is exported out of the bacteria into the media. One only needs to remove the media from the bed prior to attempting to isolate the desired product. For "free floating" bioreactors, one can centrifuge the liquid/bacteria mixture to pellet the bacteria. Then one removes the liquid containing the desired protein of interest from the pelleted bacteria. Next one isolates the desired protein of interest from the media. A further benefit of the disclosed system is that the media will contain less undesired proteins than are present in media in which bacteria were disrupted; all the intracellular components of the disrupted bacteria are absent from the media in the present invention. Thus purification of the desired protein of interest is easier. Furthermore, having tags and protease cleavage sites present within the export protein::protein of interest fusion protein further facilitate the isolation and purification of the protein of interest.

One example of a bioreactor is the apparatus taught in U.S. Pat. No. 5,635,368, "Bioreactor with immobilized lactic acid bacteria and the use thereof," to Lommi, et al., Jun. 3, 1997, which is hereby incorporated by reference in its entirety. The Lommi apparatus relates to a bioreactor with immobilized bacteria, which is characterized in that the bacteria are fixed on the surface of a substantially non-compressible carrier. Another example of a bioreactor is found at U.S. Pat. No. 4,910,139, "Method for continuously producing citric acid by dual hollow fiber membrane bioreactor," to Chang, et al., Mar. 20, 1990, which is hereby incorporated by reference in its entirety. This invention relates to growing immobilized bacteria to produce citric acid continuously.

An additional bioreactor apparatus is disclosed in U.S. Pat. No. 5,585,266, "Immobilized cell bioreactor," to Plitt, et al., Dec. 17, 1996, which is hereby incorporated by reference in its entirety. The disclosed Plitt device relates to an immobilized cell bioreactor wherein the cells are harbored within or upon an immobilization matrix including cell support sheets comprised of common textile fabric. U.S. Pat. Nos. 4,665,027 and 5,512,480, both of which are incorporated by reference, disclose other bioreactor embodiments.

F. Vaccines

The protein export system described herein has utility in the production of vaccines. For example, the production of subunit vaccines can be achieved using the protein export system as the system facilitates recombinant protein harvest and reduces the presence of contaminating proteins from the growth medium in which the recombinant host cells are propagated. Recombinant host cell vaccines can also be used to generate immunogenic compositions where the recombinant host cell is provided to a subject and the subject's immune system generates an immune response against the proteins exported from the recombinant host cell. Thus, the present invention encompasses subunit vaccines, comprising proteins produced using the protein export systems of the present invention, as well as live bacterial vector vaccines comprising recombinant host cells transformed with a protein export system of the present invention.

The protein export system described herein can be used with any antigen to prepare a vaccine therefrom, where the antigen is the protein of interest as described above. Vaccine preparation is generally described in New Trends and Developments in Vaccines, edited by Voller et al., University Park Press, Baltimore, Md. U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of antigen in each vaccine dose is selected as an amount which induces an immunoprotective response without significant, adverse side effects in typical vaccines. An immunoprotective response is one that confers an increased ability to prevent, delay or reduce the severity of the onset of a disease, as compared to such abilities in the absence of vaccination. Such an amount will vary depending on which specific antigens are employed and the delivery technology used (by way of example only, purified proteins or live bacteria), as well as factors such as the weight, age and health of the recipient. Generally it is expected that doses comprising purified proteins in subunit vaccines will comprise 1-1000 μg of total antigen, preferably 2-200 μg. Generally it is expected that doses comprising live bacteria delivering proteins of interest (live bacterial vector vaccines) will comprise 1-1000 ng of total antigen of interest. An optimal amount for a particular vaccine can be ascertained by standard studies involving observation of antibody titers and other responses in subjects. Following an initial vaccination, subjects (animal or human) may receive one or more booster doses, for example after 1 and 6 months.

The protein export system can also be used with a live bacterial vector vaccine to increase the efficacy of the preparation. For example, U.S. Pat. No. 5,387,744, to Curtiss et al., entitled "Avirulent microbes and uses therefore: *Salmonella typhi*," which is hereby incorporated by reference, provides for a live bacterial vector vaccine against *S. Typhi*. More specifically, the Curtiss patent provides immunogenic compositions for the immunization of a vertebrate or invertebrate comprising an avirulent derivative of *S. Typhi*. The derivatives having a mutation of the cya and/or crp and/or cdt genes.

The avirulent derivatives taught by Curtiss et al., can be transformed with the protein export system described herein to allow the resulting recombinant organism to act as an immunogenic composition against *S. Typhi*, as well as any other antigen or antigens that are coupled to the protein export protein of the described system.

It is contemplated that the subunit vaccines and the bacterial live vector vaccines of the present invention will be administered in pharmaceutical formulations for use in vaccination of individuals, preferably humans. Such pharmaceutical formulations may include pharmaceutically effective carriers, and optionally, may include other therapeutic ingredients, such as various adjuvants known in the art.

The carrier or carriers must be pharmaceutically acceptable in the sense that they are compatible with the vaccine components and are not unduly deleterious to the recipient thereof. Suitable carriers may include water or a saline solution, with or without a stabilizing agent, buffered solutions, dispersion media, coatings, isotonic preparations.

The modes of administration may comprise the use of any suitable means and/or methods for delivering the subunit vaccines and the bacterial live vector vaccines to a corporeal locus of the host animal where the subunit vaccines and the bacterial live vector vaccines are immunogenic, generating protective levels of relevant and desired immune responses. Delivery modes may include, without limitation, parenteral administration methods, such as subcutaneous (SC) injection, intravenous (IV) injection, transdermal, intramuscular (IM), intradermal (ID), as well as non-parenteral, e.g., oral, nasal, intravaginal, pulmonary, opthalmic and/or rectal administration.

The bacterial live vector vaccines of the present invention may be usefully administered to the host animal with any other suitable pharmacologically or physiologically active agents, e.g., antigenic and/or other biologically active substances. The animals to which the fusion proteins and vaccines of the present invention may be administered include mammalian species such as humans, non-human primates (e.g., monkeys, baboons, and chimpanzees), horses, bovine animals (e.g., bulls, cows, or oxen), pigs, goats, sheep, dogs, cats, rabbits, gerbils, hamsters, rats, and mice, and non-mammalian species such birds (e.g., chickens, turkeys, and ducks) and fish.

Pharmaceutical formulations of the present invention can be presented, for example, as discrete units such as capsules, cachets, tablets or lozenges, each containing a predetermined amount of the vector delivery structure; or as a suspension.

G. Additional Utility

In addition to therapeutic proteins and antigens which are useful for the pharmaceutical industry, the gene of interest may encode for enzymes, polypeptides, proteins, or amino acids which maybe useful for, by way of example only, the food industry, the nutritional supplement industry, the animal feed industry, the biomediation industry, the waste disposal industry, and the waste treatment industry. For these industries, the protein of interest encoded by the gene of interest may not need to be isolated from the medium of a bioreactor for the protein of interest to serve its function. The protein of interest may be a catalyst for a desired reaction or may act as a precursor component for a desired reaction.

The following examples are provided for illustrative purposes only, and are in no way intended to limit the scope of the present invention.

EXAMPLES

Example 1

Cloning and Mutagenesis of *S. Typhi* clyA

Identification of clyA was accomplished by BLASTN analysis of the recently completed *S. Typhi* genome sequence available from the Sanger Centre (Wellcome Trust Genome Campus, Hinxton, Cambridge, CB10 1SA, UK) (See the website having the address sanger.ac.uk/Projects/S_typhi/blast_server.shtml), using the DNA sequence from *E. coli* hlyE (GenBank accession number U57430).

The clyA open reading frame was identified as a 912 bp sequence predicted to encode a 304 residue protein with a molecular mass of 33.8 kDa that is 89.4% identical to *E. coli* HlyE. Although clyA is 85.3% identical to the 915 bp *E. coli* hlyE open reading frame, the upstream transcriptional control region is distantly related with only 33.6% identical bases within a 250 bp region.

Based on this analysis, primers were designed for PCR amplification of a promoterless genetic cassette encoding ClyA in which an optimized ribosome-binding site was engineered 5'-proximal to the ATG start codon. The primer sequences are listed in Table 2.

TABLE 2

Primers used in construction and sequence analysis of the plasmid cassettes

| Primer Number | Sequence[a] | Cassette created | Template |
|---|---|---|---|
| 1 | 5'GGATCCAAAATAAGGAGGAAAAAAAAATGACTAGTATTT TTGCAGAACAAACTGTAGAGGTAGTTAAAAGCGCGATCGA AACCGC AGATGGGCATTAGATC-3' (SEQ ID NO: 3) | clyA-tetA | CVD 908-htrA |
| 2 | 5'CCTAGGTTATCAGCTAGCGACGTCAGGAACCTCGAAAAG CGTCTTCTTACCATGACGTTGTTGGTATTCATTACAGGTGTT AATCAT TTTCTTTGCAGCTC-3' (SEQ ID NO: 4) | " | " |
| 3 | 5'CACGGTAAGAAGACGCTTTTCGAGGTTCCTGACGTCGCTA GCTGATAACCTAGGTCATGTTAGACAGCTTATCATCGATA AGCTTT AATGCGGTAGT-3' (SEQ ID NO: 5) | " | pBR322 |
| 4 | 5'AGATCTACTAGTGTCGACGCTAGCTATCAGGTCGAGGTG GCCCGGCTCCATGCACCGCGACGCAACGCG-3' (SEQ ID NO: 6) | " | " |
| 5 | 5'ACTAGTCACCCAGAAACGCTGGTGAAAGTAAAAGATGCT GAA GATCAGTTGGGTGCACGA-3' (SEQ ID NO: 7) | bla-tetA | pGEM-T |

TABLE 2-continued

Primers used in construction and sequence analysis of the plasmid cassettes

| Primer Number | Sequence[a] | Cassette created | Template |
|---|---|---|---|
| 6 | 5'CATTAAAGGTTATCGATGATAAGCTGTCAAACATGAGCT AGCCTAGGTCATTACCAATGCTTAATCAGTGAGGCACCTAT CTCAGC GATCTGTCTATTTCG-3' (SEQ ID NO: 8) | " | " |
| 7 | 5'CGAAATAGACAGATCGCTGAGATAGGTGCCTCACTGATTA AGCATTGGTAATGACCTAGGCTAGCTCATGTTTGACAGCT TATCAT CGATAACCTTTAATG-3' (SEQ ID NO: 9) | " | pBR322 |
| 8 | 5'GCGCACTAGTAAAGAAACGAACCAAAAGCCATATAAGG AAA CATACGGCATTTCCCATATTACACGCCATG-3' (SEQ ID NO: 10) | *sacB-tetA* | pIB279 |
| 9 | 5'TAAACTACCGCATTAAAGCTTATCGATGATAAGCTGTCAA ACATGACCCGGGTCACTATTTGTTAACTGTTAATTGTCCTT GTTCAA GGATGCTGTCTTTGAC-3' (SEQ ID NO: 11) | " | " |
| 10 | 5'TCATGTTTGACAGCTTATCATCGATAAGCTTTAATGCGGT AGT TTA-3' (SEQ ID NO: 12) | " | pBR322 |
| 11 | 5'GCGCAGATCTTAATCATCCAC*AGGAGGC*GCTAGCATGAG TAAAGGAGAAGAACTTTTCACTGGAGTTGTCCCAATTCTTG-3' (SEQ ID NO: 13) | *gfpuv-tetA* | pGEN84 |
| 12 | 5'GTGATAAACTACCGCATTAAAGCTTATCGATGATAAGCTG TCAAACATGAGCGCTCTAGAACTAGTTCATTATTTGTAGA GCTCATCCATGCCATGTGTAATCCCAGCAG-3' (SEQ ID NO: 14) | " | " |

[a]Relevant restriction sites are designated in bold case, underlined; ribosome binding sites and start codons are designated in *italics*.

To facilitate recovery, overlapping PCR techniques were used to create a promoterless 2252 base pair clyA-tetA genetic cassette synthesized by overlapping PCR as previously described using primers 1 and 2 with chromosomal template DNA from CVD 908-htrA, and primers 3 and 4 with template derived from pBR322, and recovered in pGEM-T (Promega, Madison Wis.) transformed into *E. coli* DH5α.

Recombinant clones were screened on solid agar medium containing sheep red blood cells. Specifically, screening for hemolytic activity was performed on freshly prepared 1×LB agar medium containing appropriate antibiotic selection and 5% sheep blood. Plates were then incubated at 37° C. for 24 hours to detect zones of red blood cell (RBC) hemolysis. Several colonies were immediately identified which produced clear halos of hemolysis. This observation suggested that if clyA requires accessory proteins for translocation out of the bacterium, these proteins are apparently common to both *S. Typhi* and *E. coli*. A positive isolate, designated pGEM-TclyA, was chosen for further use.

The functional roles of various regions of ClyA were examined to provide information for the proper engineering of recombinant fusion proteins encoding an antigen fused to ClyA. Specifically, the role played by the amino terminus, the carboxyl terminus, or both, in exportation of hemolysin out of the bacterium was examined.

To accomplish this, clyA was randomly mutagenize using the transposon TnphoA. The "phoa" of "TnphoA" encodes alkaline phosphatase (See Manoil & Bechwith, PNAS Vol 82, pp 8129-8133, 1985). Transposition of TnphoA allows for random formation of in-frame fusions of the N-terminus of PhoA onto a given target protein. TnphoA mutagenesis was carried out after electroporation of pGEM-TclyA, expressing functional *S. Typhi* ClyA hemolysin, into DH5α to yield DH5α (pGEM-TclyA). A cross-streak mating was then performed between DH5α (pGEM-TclyA) and the TnphoA donor strain SM10 (pRT733) and selecting transconjugants on 2×LB50 supplemented with tetracycline, carbenicillin, and kanamycin at 10 μg/ml, 50 μg/ml, and 10 μg/ml respectively (2×LB50+T10050K10). Bacteria were then pooled and grown up in broth cultures for plasmid purification, and purified plasmids retransformed into the phoAΔ20 mutant *E. coli* strain CC118 for selection of Pho+ transformants on 2×LB50+T10C50K10 supplemented with 200 μg/ml of the alkaline phosphatase substrate 5-Bromo-4-Chloro-3-Indolyl-Phosphate (BCIP; Sigma, St. Louis, Mo.). Target protein fusions that are N-terminally secreted into the periplasm, surface exposed, or exported out of the bacterium entirely, can easily be screened using the chromogenic substrate BCIP to detect deep blue halos of hydrolysis; proteins which are C-terminally secreted will not be detected using this method.

Using TnphoA mutagenesis, 4 of 621 PhoA+ colonies were identified that no longer displayed hemolytic activity. Sequencing of one isolate confirmed the in-frame insertion of PhoA after residue 179 (Ala) of ClyA. This insertion truncated ClyA in the proposed hydrophobic transmembrane region and removes the remaining 125 carboxyl-terminal residues. It was therefore concluded that the carboxyl-terminus of *S. Typhi* ClyA is not required for transport of the cytoplasm of *E. coli* (and presumably from *S. Typhi* also), and that genetic fusion of heterologous genes potentially encoding exported protein fusions should be carried out at the 3'-terminus of clyA.

Example 2

Construction of Carboxyl-Terminal Fusions of Test Antigens to ClyA

To test the ability to export passenger proteins fused at the carboxyl terminus of ClyA, the bla gene encoding the RTEM-1 β-lactamase protein which confers resistance to both ampicillin and carbenicillin, was chosen for experimentation.

This protein fusion was engineered as a genetic fusion of a SpeI cassette inserted in-frame into the NheI site adjacent to the tandem stop codons at the clyA 3'-terminus of pSEC84. Initially, an 807 bp SpeI-NheI fragment encoding the mature 268 amino acid β-lactamase without the 23 residue signal sequence was synthesized from a pBR322 derivative by PCR. The purified fragment was then inserted in-frame into the engineered carboxyl terminal NheI site of clyA to create a 1742 bp clyA-bla genetic fusion encoding a predicted 62.9 kDa fusion protein. The desired plasmid construct was easily recovered in isolated colonies from cultures grown in the presence of 5 μg/ml carbenicillin, but plasmids recovered after selection with 50 μg/ml carbenicillin appeared to be unstable and genetically rearranged.

bla-tetA Fusion

Because of the problem with plasmid stability and genetic rearrangement of the clyA-bla construct described above, the bla-tetA fusion was synthesized as a 2111 bp SpeI cassette by overlapping PCR using primers 5 and 6 with pGEM-T template and primers 7 and 4 with template derived from pBR322; insertion of this cassette into pSEC84 cleaved with NheI yielded pSEC84bla (see FIG. 1B).

After introduction into CVD 908-htrA, colonies were screened for retention of hemolytic activity, and then screened for β-lactamase activity using the chromogenic substrate nitrocefin at a concentration of 100 μg/ml in 2×LA50+DHB+T10; plates were incubated at 30° C. for at least 16 hours and examined for the presence of red halos around colonies indicating cleavage of nitrocefin. Red halos were observed around CVD 908-htrA(pSEC84bla), indicating cleavage of nitrocefin, confirmed the presence of enzymatically active β-lactamase. It was concluded that an approximate doubling of the molecular mass of ClyA from 34 kDa to 63 kDa resulted in a 2 domain fusion protein in which both domains apparently folded correctly to maintain the expected biological activity of each domain.

sacB-tetA Fusion

To investigate the versatility of ClyA as a fusion partner to export heterologous antigens out of S. Typhi, the efficiency of ClyA to export the potentially lethal levansucrase encoded by sacB from Bacillus subtilis was examined. Expression of the sacB gene is lethal when expressed within the cytoplasm of enteric bacteria, including S. Typhi, growing in the presence of sucrose. Construction of a ClyA-SacB protein fusion with a predicted molecular mass of 83.9 kDa, for introduction into CVD 908-htrA was attempted. This fusion was engineered as a sacB-tetA SpeI cassette encoding the mature 445 residue 50.0 kDa levansucrase, without the 29 amino acid signal sequence, and inserted in-frame into the engineered carboxyl terminal NheI site of ClyA in pSEC84. CVD 908-htrA carrying the desired construct was selected using tetracycline and screened in the presence of sucrose for survival. If ClyA-SacB failed to be exported out of the cytoplasm, no isolates would be recovered, but for fusions either surface expressed or fully exported out of the bacterium into the surrounding medium, an enzymatically active SacB moiety would be expected to cleave sucrose to release glucose, which would immediately be transported into the bacterium and metabolized.

The sacB-tetA cassette was synthesized using primers 8 and 9 with pIB279 template and primers 10 and 4 as above to create a 2653 bp SpeI cassette inserted into pSEC84 generating the clyA::sacB fusion of pSEC84sacB (SEQ ID NO:18) (see FIG. 1C). After introduction into CVD 908-htrA, colonies were again screened for retention of hemolytic activity, and then examined for levansucrase activity by plating on MacConkey agar base medium (Difco) supplemented with DHB and either sucrose (8% or 16% w/v) or 8% sucrose+8% arabinose as the sole carbohydrate source. Plates were incubated at 30° C. for 16-24 hours to recover isolated cfus and determine fermentation of the carbohydrate; additional incubation at room temperature for several more days was required to observe formation of the polysaccharide-like domes over colonies.

As shown in FIGS. 2B and 2D, growth of CVD 908-htrA (pSEC84sacB) was excellent when grown on indicator medium containing either 8% sucrose or 16% sucrose as the sole carbohydrate source (where grown on MacConkey agar base medium). Indeed, a polysaccharide-like dome was observed to form over isolated CVD 908-htrA(pSEC84sacB) colonies which was not observed for CVD 908-htrA (FIGS. 2A and 2C), and intensified with increasing concentration of sucrose. Hypothesizing that this polysaccharide-like material was levan, formed by the levansucrase-catalyzed polymerization of fructose liberated from hydrolysis of sucrose, we attempted to block this polymerization by introducing 8% L-arabinose which is known to inhibit levansucrase. As shown in FIG. 2F, domes were no longer observed, with CVD 908-htrA and CVD 908-htrA(pSEC84sacB) colonies now appearing similar.

Figure 3:
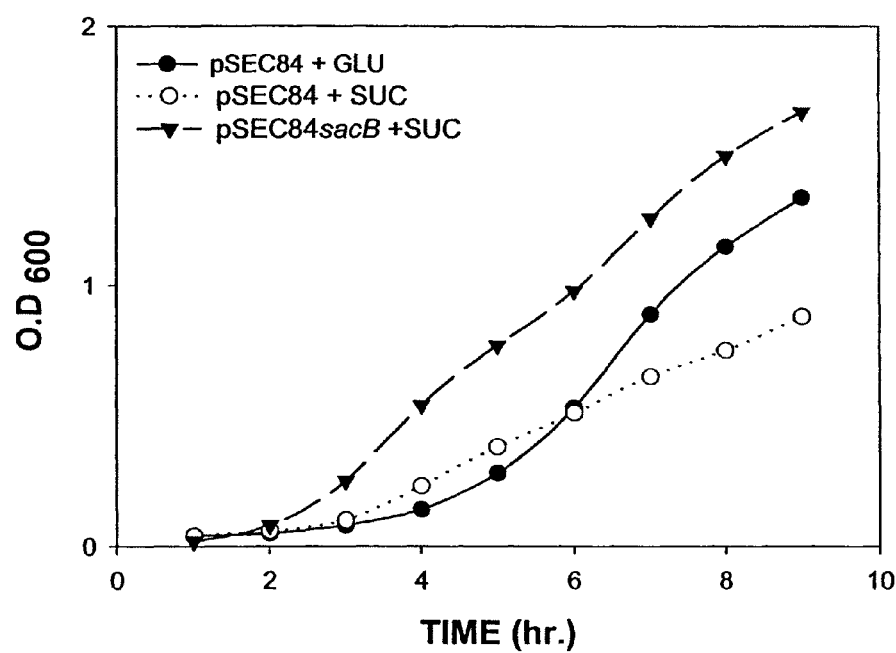
FIG. 3 illustrates the growth of CVD 908-htrA expressing either ClyA (pSEC84) or ClyA-SacB (pSEC84sacB), grown in 2XLB50 broth supplemented with DHB and either 10% sucrose or 10% glucose.

If ClyA-SacB protein fusions are indeed exported out of CVD 908-htrA(pSEC84sacB), then cleavage of sucrose by the SacB domain to liberate free glucose should provide a metabolic advantage compared CVD 908-htrA when these strains are grown as broth cultures in the presence of sucrose. To test this hypothesis, 100 ml broth cultures of either CVD 908-htrA(pSEC84) or CVD 908-htrA(pSEC84sacB) were set up in 1 liter baffle flasks containing 2×LB50+DHB+K10 plus 10% sucrose and growth was compared to CVD 908-htrA(pSEC84) cultures grown in the presence of 10% glucose as a positive control. As shown in FIG. 3, CVD 908-htrA (pSEC84sacB) was observed to grow faster in the presence of sucrose than either CVD 908-htrA(pSEC84) growing with glucose or sucrose, an observation confirmed with viable counts. When taken together with results observed above for ClyA-Bla, the data strongly suggest that ClyA is a versatile fusion partner for export out of out of bacteria properly folded fusion proteins in which the biological activity of the fused domains is preserved.

clyA::gfpuv Fusion

Figure 4:
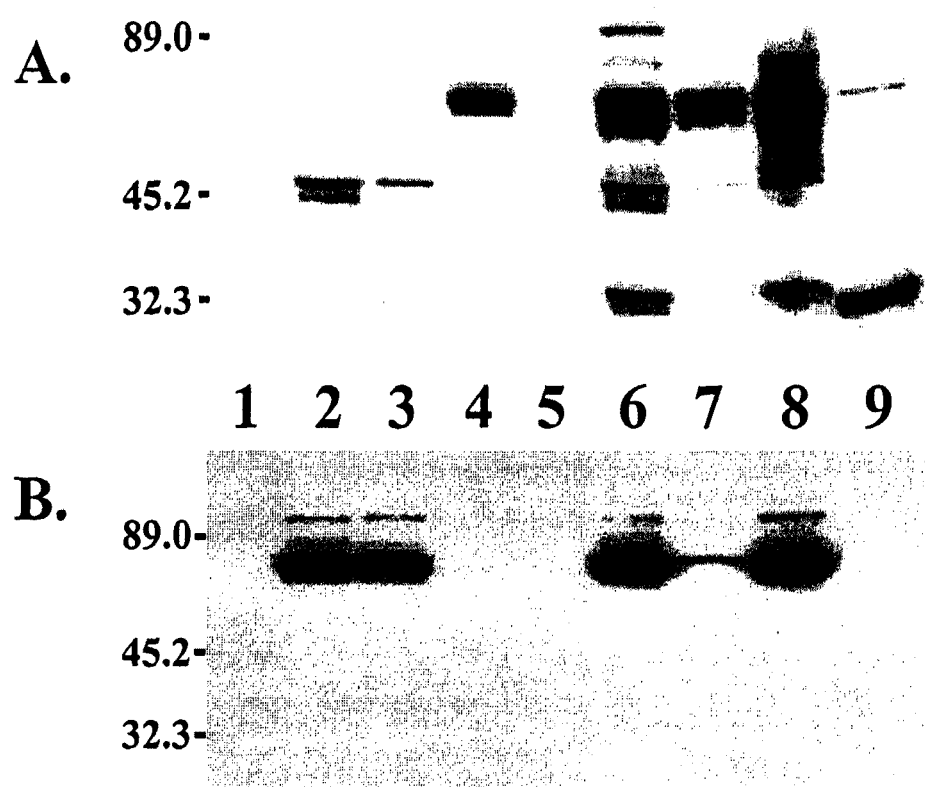
FIG. 4 illustrates Western immunoblot analysis of bacterial cell fractions from either CVD 908-htrA (lanes 1-3) or CVD 908-htrA(pSEC84gfpuv) (lanes 4-8). Cell fractions are loaded as follows: supernatants, lanes 1 and 4; cytoplasmic, lanes 2 and 6; periplasmic, lane 5; insoluble, lane 7; whole cell, lanes 3 and 8; and 50 ng GFPuv, lane 9. Membranes with identical samples were probed with antibodies specific for GFPuv (panel A) or *E. coli* GroEL (panel B).

To further define the export properties of ClyA and specifically verify the presence of ClyA fusion products in the supernatant of exponentially growing CVD 908-htrA, a genetic fusion of clyA was constructed where clyA was fused to the fluorescent reporter green fluorescent protein (GFPuv) creating the clyA::gfpuv cassette of pSEC84gfpuv (see FIG. 1D), and isogenic to both pSEC84bla and pSEC84sacB. Again, CVD 908-htrA(pSEC84gfpuv) remained hemolytic but with reduced fluorescence when compared to cytoplasmically expressed GFPuv. Using GFP polyclonal antibody (BD Biosciences Clontech, Palo Alto, Calif.), the export of ClyA-GFPuv into the culture supernatant was examined using Western immunoblot analysis, as shown in FIG. 4. FIG. 4 illustrates a set of Western immunoblots analyzing bacterial cell fractions from either CVD 908-htrA (lanes 1-3) or CVD 908-htrA(pSEC84gfpuv) (lanes 4-8). Cell fractions are loaded as follows: supernatants, lanes 1 and 4; cytoplasmic, lanes 2 and 6; periplasmic, lane 5; insoluble, lane 7; whole cell, lanes 3 and 8; and 50 ng GFPuv, lane 9. Membranes with identical samples were probed with antibodies specific for GFPuv (panel A) or E. coli GroEL (panel B). As can be seen in this figure, a significant amount of the expected 61 kDa protein fusion is detected in 0.5 ml of TCA-precipitated supernatant from CVD 908-htrA(pSEC84gfpuv) (lane 4); an irrelevant cross-reacting species of approximately 45 kDa is also detected in the cytoplasm of CVD 908-htrA (lane 2) and in the cytoplasmic, insoluble, and whole cell fractions of CVD 908-htrA(pSEC84gfpuv); interestingly, lane 5 suggests that very little ClyA-GFPuv is recovered from the periplasmic space.

Conclusion

The results from this work clearly support the conclusion that the cryptic hemolysin ClyA from S. Typhi can be used to facilitate the export of heterologous antigen domains out of the attenuated vaccine strain CVD 908-htrA and into the surrounding medium. Furthermore this work demonstrates that ClyA can be used to facilitate the export of a fusion protein out of bacteria into the surrounding medium. As illustrated above, the ability to export properly folded proteins of interest fused at the carboxyl terminus of ClyA was shown using the bla gene encoding the RTEM-1 β-lactamase protein which confers resistance to both ampicillin and carbenicillin. The bla gene of pBR322 is 861 bp in length and encodes a 31.5 kDa protein with a 23 amino acid signal sequence directing N-terminal secretion of β-lactamase into the periplasmic space. The work above indicates the successful engineering of a gene fusion encoding a functional ClyA-β-lactamase protein fusion which retained both hemolytic activity and the ability to cleave the chromogenic β-lactamase substrate nitrocefin to produce red halos against a yellow background of uncleaved nitrocefin.

Interestingly, attempts to select for such expression vectors when growing transformants in rich medium supplemented with 50 μg/ml of either carbenicillin or ampicillin were unsuccessful and only extensively rearranged plasmids were recovered as judged by restriction mapping. It has been conclusively demonstrated that cytoplasmically expressed β-lactamase confers resistance to ~5 μg/ml of ampicillin, while appropriately expressed periplasmic β-lactamase confers resistance to >4000 μg/ml of ampicillin. However, surface display of β-lactamase protein fusions have been shown to confer resistance to ~100 μg/ml of ampicillin. Indeed, Chervaux et al. have reported that HlyA-mediated secretion of β-lactamase fusions out of *E. coli* again confer low-level resistance to ~5 μg/ml of ampicillin. They demonstrated that even though the specific activity of the intact β-lactamase domain of the surface fusion remained similar to that of unmodified β-lactamase, resistance to high levels of ampicillin was not observed, and they concluded that bacterial resistance to β-lactam antibiotics requires significant concentrations of β-lactamase within the periplasmic space close to the killing targets. Based on such observations, it was concluded that properly folded ClyA-β-lactamase protein fusions were synthesized within CVD 908-htrA(pSEC84bla) and exported to confer a hemolytic phenotype, as well as β-lactamase-mediated hydrolysis of the chromogenic cephalosporin nitrocefin, without conferring resistance to ampicillin or carbenicillin.

To more clearly define the nature of ClyA-mediated export of heterologous antigen domains out of CVD 908-htrA, and perhaps rule out the involvement of periplasmic intermediates, fusions of sacB, encoding the potentially lethal levansucrase from *B. subtilis* were studied. Levansucrase is a 50 kDa single polypeptide exoenzyme that catalyzes the hydrolysis of sucrose to yield free glucose and fructose, and in turn catalyzes the polymerization of fructose into long polymers called levan. Secretion of levansucrase from *B. subtilis* growing on medium containing sucrose results in the growth of isolated colonies covered by an impressive dome of viscous levan after extended incubation at room temperature.

It is well established that cytoplasmic and periplasmic expression of levansucrase encoded by sacB is lethal for a variety of bacteria growing in the presence of sucrose. It has recently been shown using signal peptide mutations that levansucrase becomes lethal within the cytoplasm of *B. subtilis* grown in the presence of sucrose, and that inactivation of the fructose polymerase activity was essential for removal of sucrose-induced lethality. It was therefore reasoned that failure of ClyA-SacB fusions to be exported out of both the cytoplasm and periplasmic space of CVD 908-htrA should result in significant intracellular accumulation of the fusion protein resulting in lethality for CVD 908-htrA (pSEC84sacB) growing in the presence of sucrose.

As shown in FIG. 2B, however, CVD 908-htrA (pSEC84sacB) was observed not only to grow in the presence of 8% sucrose but to ferment the sugar, a phenotype not observed for CVD 908-htrA(pSEC84) grown under the identical conditions. As the concentration of sucrose was increased from 8% to 16% sucrose, fermentation of sucrose also increased with the accumulation of impressive domes of levan-like material which vanished in the presence of the levansucrase inhibitor arabinose. Similar observations of levansucrase activity were reported by Jung et al. for a surface expressed levansucrase domain fused to the carboxyl terminus of the ice nucleation protein of *Pseudomonas syringae* and expressed within *E. coli*. In view of these results, it was concluded that the engineered CVD 908-htrA(pSEC84sacB) had the ability to utilize sucrose as a carbon source in broth culture experiments in which CVD 908-htrA(pSEC84sacB) was observed to grow faster than CVD 908-htrA(pSEC84) grown either in the presence of sucrose or pure glucose. It was again concluded that, as with the ClyA-β-lactamase protein fusions described above, that properly folded ClyA-SacB protein fusions were synthesized within CVD 908-htrA, and exported to confer both the expected hemolytic phenotype, as well as levansucrase activity allowing for the extracellular catabolism of an alternate carbohydrate source not utilized by the plasmid-less host strain.

Example 3

Bioreactor Protein Expression of a ClyA-SacB Fusion

A bioreactor is prepared according to the teachings of U.S. Pat. No. 5,635,368, which is hereby incorporated by reference in its entirety. Briefly, granular derivatized cellulose is manufactured according to U.S. Pat. No. 4,355,117 as follows: 25 parts of fibrous cellulose is mixed with 25 parts of titanium dioxide and the mixture is compounded with 50 parts of high-impact polystyrene using a twin-screw extruder. The extrudate is cooled in water, and sieved to a particle size of 0.35-0.85 mm. The sieved granular agglomerated cellulose particles are derivatized to form DEAE cellulose as described in the U.S. patent above.

Next, ten (10) grams of the granular DEAE-cellulose is reduced to a slurry in distilled water and soaked for 5 hours with occasional stirring. The hydrated carrier is then decanted with the distilled water and transferred into a glass column with an inner diameter of 15 mm where it forms a bed with a height of 145 mm.

Bacteria transformed with pSEC84sacB (see Example 2) are cultured for 48 hours at 30° C. Fifty (50) milliliters of the cell suspension is pumped through the carrier bed at a flow velocity of 25 ml/hour. Subsequently, additional amounts of culture medium is pumped through the carrier bed. The outflow of the column is collected and the recombinantly expressed ClyA-SacB fusion protein (encoded by SEQ ID NO: 19) is isolated and purified from the outflow. Cleavage of SacB would provide ample commercial amounts of levansucrase for the generation of levan.

Example 4

His-Tag Protein Purification Under Denaturing Conditions

A bacterial culture is transformed with an expression vector containing an expression cassette comprising the coding sequence for an attenuated ClyA protein fused to a sacB gene, which is fused to a coding sequence encoding a protease recognition site, which is fused to a polyhistidine tag encoding sequence. The bacterial culture is introduced into a bioreactor such as that described in Example 3.

The culture is placed under conditions promoting expression of the recombinant fusion protein, which is exported into the culture medium. The culture medium is collected and applied to a Ni column (HISTRAP; Pharmacia) equilibrated with a urea containing buffer at a concentration sufficiently high to denature the protein. The column is then washed and eluted. The eluate is analyzed by gel electrophoresis to determine the presence of the purified protein.

Purified protein containing fractions are dialyzed against an enzyme digestion buffer. The dialyzed samples are then pooled and subjected proteolysis catalyzed by the appropriate enzyme. The proteolyzed sample is purified to eliminate the deleted polyhistidine tag, leaving the isolated, purified protein.

Example 5

Construction of Attenuated CVD 908-htrA that Expresses Frag C and Raising an Immune Response Thereto A ClyA-Frag C fusion protein is generated in CVD 908-htrA according to the steps discussed in Example 1. Our approach is to express a codon-optimized toxC open reading frame encoding fragment C of tetanus toxin inserted into ClyA expressed from the expression vector disclosed herein. Export of fragment C is accomplished through an in-frame genetic fusion of toxC to the 3' terminus of clyA and carried on the oriE1 replicon pSEC84 as a 1426 bp $P_{ompC}$-clyA EcoRI-NheI cassette. toxC encoding fragment C is re-engineered from prior art constructs using the forward primer 5'-GCGCA ACTAGTAAAAACCTTGATTGTTGGGTCGACAA CGAAGAAGACATCGATGTT-ATCCTGAAAAAGTC-TACCATTCTGAACTTGGACATCAAC-3' (SEQ ID NO: 15) and the reverse primer 5'-AACTACCGCATTAAAGCT-TATCGATGATAAGCTGTCAAACATGA GCTAGCCTAGGT CATTAGT-CGTTGGTCCAACCT-TCATCGGTCGGAACGAAGTA-3' (SEQ ID NO: 16) to generate the desired PCR product (1424 bp). The toxC cassette is then subcloned into pSEC84 digested with NheI to construct pSEC84toxC. The DNA sequence of the intended clyA-toxC fusion junction is confirmed using the sequencing primer 5'-CGATGCGGCAAAATTGAAATTAGC-CACTGA-3' (SEQ ID NO: 17) which hybridizes 172 bases upstream of the engineered NheI site at the 3'-terminus of clyA. Constructs are screened for retention of hemolytic activity and confirmed for export of the ClyA-Frag C into the supernatant by Western immunoblot analysis.

Groups of ten 6 weeks old Balb/c mice are immunized intranasally with $1.0 \times 10^{10}$ cfu of strain CVD 908-htrA expressing the ClyA-Frag C fusion protein. Mice are bled prior and 30 days after their immunization, and their serum is stored at $-20°$ C. until use. Antibodies present in the serum against ClyA and Frag C antigens are determined by ELISA. The results indicate that immunization with strain CVD 908-htrA expressing the ClyA-Frag C fusion protein elicits antibody levels against the Frag C antigen that are significantly higher than those obtained with strain 908-htrA not expressing the ClyA-Frag C fusion protein. The results demonstrate that the expression of the Frag C antigen as a fusion protein with ClyA enhances the immune response against this antigen. Protective immunity against tetanus toxin is confirmed by challenging immunized mice with otherwise lethal doses of natural tetanus toxin.

Example 6

Construction and Analysis of Non-Hemolytic Variants of S. Typhi ClyA

Although as demonstrated herein ClyA can be adapted for use in an export system for foreign antigens, ClyA being a theoretical virulence factor poses a potential problem in vaccine applications. Therefore, variants of S. Typhi ClyA were produced through mutation wherein the export activity of the variants was maintained, but their hemolytic activity was abolished.

Materials and Method
Bacterial Strains and Culture Conditions

All plasmid constructions were recovered in E. coli strain DH5α (Invitrogen Life Technologies, Carlsbad, Calif.). Live-vector Salmonella serovar Typhi CVD 908-htrA is an auxotrophic derivative of wild-type strain Ty2 with deletions in aroC, aroD, and htrA (Tacket et al, 1997). Salmonella enterica serovar Typhi strains used in this work were grown in media supplemented with 2,3-dihydroxybenzoic acid (DHB) (Sigma, St. Louis, Mo.) (Galen et al 1997, Hone et al, 1991). Plasmid-bearing strains of CVD 908-htrA were streaked from frozen ($-70°$ C.) master stocks on 2× Luria-Bertani agar (solid medium) containing 20 g of Bacto Tryptone, 10 g of Bacto Yeast Extract, and 50 mM NaCl (2×LB50 agar) plus kanamycin at 15 mg/ml. Plates were incubated at 30° C. for 24 to 36 h to obtain isolated colonies 2 mm in diameter and to minimize any toxicity of heterologous antigen expression in CVD 908-htrA.

Mutation of clyA Gene

Random mutagenesis was carried out using the GeneMorph II random mutagenesis kit (Stratagene, La Jolla, Calif.) and following the manufacture's instructions. To generate low mutation frequencies, 700 ng of pSEC92gfpuv was used as template and the mutation PCR was performed for 25 cycles. To generate high mutation frequencies, 10 ng of pSEC92gfpuv was used as template and the mutation PCR was carried out for 2 rounds, each with 30 cycles. Primers G751 (CTTCTCCTTTACTCATGCTAGCCACA; SEQ ID NO:26)) and G755 (AAATGGTACCTCCAAAATAAG-GAGGAAAAAAAAATG; SEQ ID NO:27)) were used to amplify the full length of clyA. After PCR, the reaction was digested with DpnI to eliminate the template plasmid. After purification, PCR products were digested with PvuI and NheI and cloned back into pSEC92gfpuv, which also had been digested with the same restriction enzymes, to regenerate an intact ClyA open reading frame. Clones were recovered in E. coli strain DH5a on TSA agar containing 5% sheep blood and incubated at 37° C. for 24 to 48 h to detect zones of hemolysis.

Green fluorescent protein expression was visualized by ultraviolet subillumination. After identifying the specific mutations abolishing hemolytic activity, selected mutations were assembled into a single ClyA open reading frame by site-directed mutagenesis using the QuikChange II-E site-directed mutagenesis kit (Stratagene, La Jolla, Calif.) and manufacturer's instructions. Primers G835 (AGCTATAG-CAATGACGCGGGCGTTATTAAAGGCAAACTGA; SEQ ID NO:28)) and G836 (TCAGTTTGCCTTTAATAACGC-CCGCGTCATTGCTATAGCT; SEQ ID NO:29)) were used to construct the clyA triple mutant encoded by pSEC93gfpuv.

Hemolytic Assay

Measurement of hemoglobin release from erythrocytes was performed as described (Sansonetti et al. 1986. Infect. Immun. 51: 461-9.), with several modifications. Bacteria were cultured to late log phase (OD600 at 0.9-1.0) and harvested. $1 \times 10^9$ cells in 50 ul PBS were mixed with equal volume of washed sheep erythrocytes (Lampire Biological, Pipersville, Pa.) in the concentration of $4 \times 10^9$/ml. The mixture was centrifuged at 2,200×g for 15 min at 30° C. and then incubated at 37° C. for two hours. The reaction was resuspended by adding 150 ul of cold PBS and then centrifuged at 2,200×g for 15 min at 4° C. At the end of the reaction, 100 μl of supernatant was transferred to a flat bottom microtiter plate. Hemolytic activity was measured by reading the optical density at 545 nm in a Versamax microplate reader (Molecular Devices, Toronto, Canada).

Immunoblot Analysis

Western immunoblot analysis was carried out as described (Galen et al, 2004 Infect. Immun. 72 (12): 7096-7106)), with care taken to analyze samples from cultures grown at 30° C. to optical densities at 600 nm ($OD_{600}$) that did not exceed 1.0. Proteins in the culture supernatant were precipitated with 10% ice cold TCA and washed twice with ice cold acetone. The pellet was dried, re-suspended in 100 mM Tris-Cl pH 8.0, and mixed with 2× sample buffer (Biorad).

Detection of GFPuv was carried out using polyclonal mouse anti-GFP primary antibody (BD Biosciences/Clontech, Palo Alto, Calif.) and a peroxidase-labeled affinity-purified goat anti-mouse secondary antibody (Kirkegaard & Perry Laboratories, Inc., Gaithersburg, Md.). Immunoblots were developed using an ECL+Plus detection system (Amersham Biosciences, Piscataway, N.J.), and blots were exposed to Kodak X-OMAT XAR-2 film. To estimate the amount of cell lysis possibly contributing to the release of ClyA-GFPuv fusions into supernatants, contamination of supernatants with cytoplasmic protein GroEL was detected using anti-*E. coli* GroEL rabbit antibody (Sigma) and an alkaline phosphatase-conjugated goat anti-rabbit secondary antibody (BioRad). Immunoblots of GroEL were developed using Immun-star AP conjugate substrate (BioRad).

Results clyA Variants

The *S. Typhi* gene clyA was mutated in plasmid pSEC92gfpuv (FIG. 5). pSEC92gfpuv (SEQ ID NO:32) encodes a codon-optimized ClyA fused to GFPuv. The codon-optimized clyA sequence is shown in SEQ ID NO:33. The clyA genes that harbor random point mutations, and thus encode the variants of the present invention, are referred to herein as clyM (see, e.g., Table 3). The target sequence subjected to mutagenesis spanned residues 18 to 303. A series of pClyM plasmids were constructed that were very similar to pSEC92gfpuv except that they harbored clyM instead of clyA. In each pClyM, a gfpuv gene was fused downstream of clyM. This fusion not only allowed the expression of ClyM to be tracked, but also served as an indicator for the correct folding of ClyM (Waldo, G S et al, 1999. Nat. Biotechnol. 17(7):691-5).

Hemolytic Activity of ClyA Variants clyM was sequenced from 43 clones that still maintained their hemolytic activity. ClyM in these clones harbored from 1 to 4 mutations (Table 3; the positions of mutations in ClyA correspond to the ClyA polypeptide sequence of SEQ ID NO:2). The sequence results indicated that a mutation can be introduced in many positions of any sub-domain of ClyA without affecting its hemolytic activity. Therefore amino acids in these positions are not critical for hemolytic activity of ClyA in the context of downstream fusion domain.

TABLE 3

| Mutation position in ClyA | ClyM clone # | Domain |
|---|---|---|
| 19 | HM42 | αA/A' |
| 20 | HM30 | αA/A' |
| 25 | HM42 | αA/A' |
| 29 | HM32 | αA/A' |
| 33 | HM15 | αA/A' |
| 51 | HM42 | |
| 55 | HM17 | |
| 55 | HM23 | |
| 58 | HM25 | αB |
| 66 | HM14 | αB |
| 71 | HM10 | αB |
| 72 | HM45 | αB |
| 73 | HM40 | αB |
| 73 | HM26 | αB |
| 73 | HM18 | αB |
| 78 | HM26 | αB |
| 84 | HM45 | αB |
| 84 | HM37 | αB |
| 90 | HM11 | αB |
| 104 | HM53 | |
| 106 | HM42 | αC |
| 107 | HM53 | αC |
| 110 | HM14 | αC |
| 110 | HM26 | αC |
| 111 | HM44 | αC |
| 114 | HM46 | αC |
| 114 | HM51 | αC |
| 122 | HM20 | αC |
| 123 | HM51 | αC |
| 128 | HM13 | αC |
| 131 | HM45 | αC |
| 143 | HM52 | αC |
| 150 | HM57 | αC |
| 157 | HM2 | αC |
| 160 | HM39 | |
| 167 | HM49 | αD |
| 168 | HM23 | αD |
| 168 | HM54 | αD |
| 169 | HM20 | αD |
| 170 | HM44 | αD |
| 171 | HM27 | αD |
| 171 | HM35 | αD |
| 172 | HM44 | αD |
| 180 | HM20 | |
| 182 | HM35 | |
| 193 | HM54 | β tongue |
| 203 | HM28 | αE |
| 203 | HM39 | αE |
| 208 | HM26 | αF |
| 219 | HM23 | αF |
| 222 | HM8 | αF |
| 224 | HM32 | αF |
| 226 | HM45 | αF |
| 230 | HM8 | αF |
| 234 | HM11 | αF |
| 234 | HM43 | αF |
| 234 | HM44 | αF |
| 242 | HM46 | αF |
| 244 | HM29 | αF |

TABLE 3-continued

| Mutation position in ClyA | ClyM clone # | Domain |
|---|---|---|
| 246 | HM28 | αF |
| 250 | HM32 | αF |
| 263 | HM10 | |
| 272 | HM44 | αG |
| 279 | HM46 | αG |
| 280 | HM2 | αG |
| 285 | HM37 | αG |
| 286 | HM39 | αG |
| 294 | HM7 | |

To determine which amino acids are critical for the hemolysin activity of S. Typhi ClyA, clyM was sequenced from 111 clones that had no visible (or much reduced) hemolytic activity, but were still fluorescent on sheep blood agar. 18 of these clones were found to have only one amino acid mutation (Table 4). Most of these amino acids are located in alpha helices C, E, F, or G. No mutations in this group were located in helices A, B or D. It has been previously reported that disruption of the naturally occurring intramolecular cysteine bridge between residues 87 and 285 of ClyA abolishes hemolytic activity by preventing oligomerization required for pore formation and cytolytic activity (Atkins A. et al. 2000. J. Biol. Chem. 275: 41150-5). The noted "Position" and wild-type amino acid ("wt") in Table 4 corresponds to the amino acid sequence of the S. Typhi ClyA polypeptide shown in SEQ ID NO:2. The "domain" is the particular domain the S. Typhi ClyA polypeptide.

TABLE 4

| Clone | Position | wt | Mutation | Domain | SEQ ID NO: |
|---|---|---|---|---|---|
| M133 | 109 | A | T | αC | |
| M165 | 109 | A | V | αC | |
| M188 | 116 | L | Q | αC | |
| M187 | 148 | L | P | αC | |
| M179 | 163 | S | C | turn between αC & αD | |
| M103 | 195 | S | N | β tongue | |
| M30 | 198 | I | N | αE | 30 |
| M128 | 199 | A | D | αE | |
| M135 | 204 | E | K | αE | |
| M182 | 204 | E | D | αE | |
| M109 | 205 | G | D | αE | |
| M64 | 207 | L | R | αF | |
| M185 | 215 | L | P | αF | |
| M163 | 225 | L | S | αF | |
| M176 | 229 | V | L | αF | |
| M150 | 281 | M | K | αG | |
| M171 | 284 | T | P | αG | |
| M148 | 285 | C | W | αG | |

Export of ClyA Variants

Figure 6:
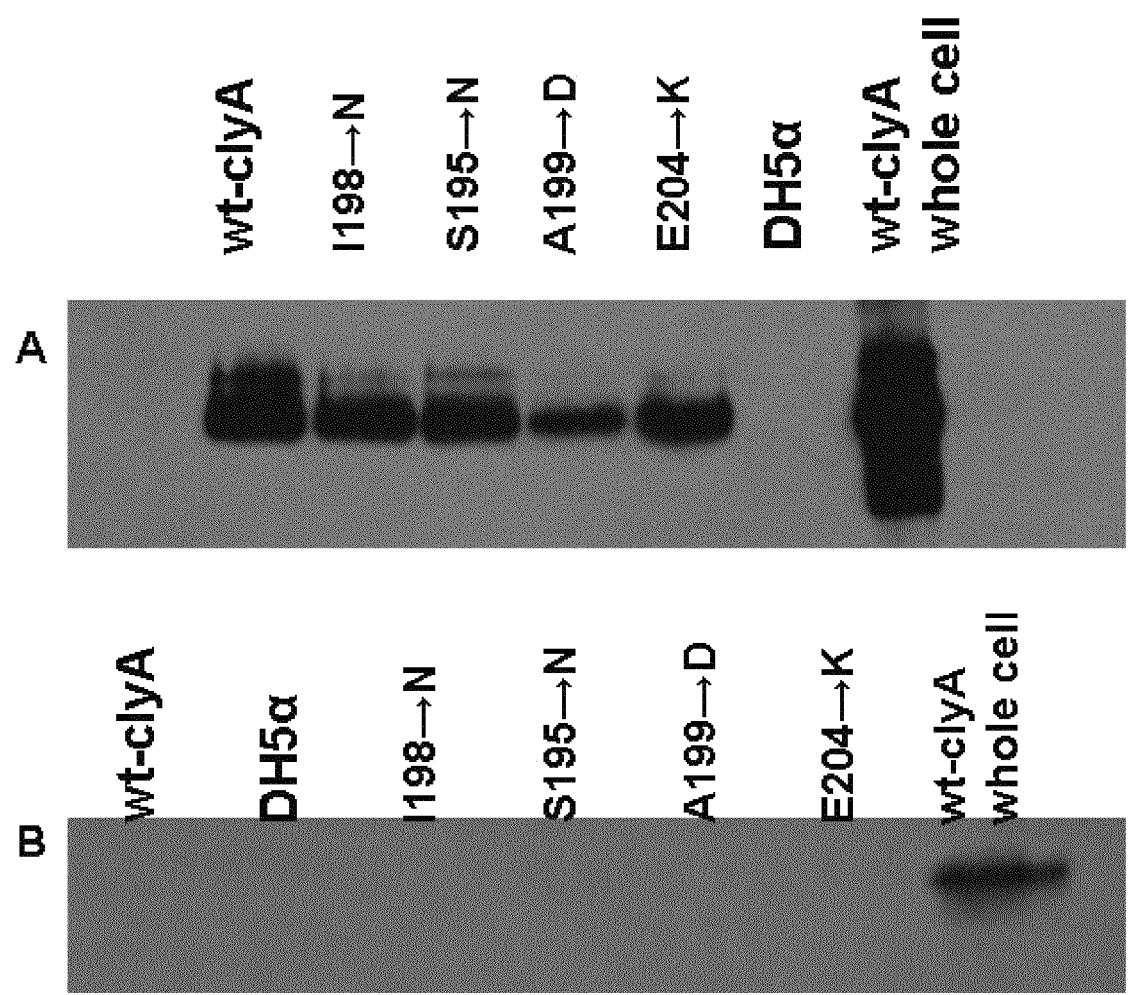
FIG. 6 shows immunoblots of clyA non-hemolytic mutants. Wt ClyA ("wt-clyA", hemolytic) and non-hemolytic mutants are expressed as fused proteins of ClyA fused to the reporter fluorescent protein GFPuv expressed from plasmids derived from pSEC92gfpuv in DH5α. A. Detection of ClyA::GFPuv fusion proteins in the culture supernatants of wt clyA (hemolytic) or clyA mutants (non-hemolytic). B. Detection of GroEL in the culture supernatants.

To investigate the export activity of the 18 non-hemolytic (or reduced hemolytic activity) fluorescent clones listed in Table 4, culture supernatants from these 18 clones were screened for the presence of GFPuv by immunoblotting. The results showed that 6 individual mutations, i.e. S195→N, I198→N, A199→D, E204→K, E204→D, and G205→D, retained export properties similar to protein fusions of wild-type (hemolytic) ClyA::GFPuv, while remaining non-hemolytic and fluorescent (FIG. 6). The 6 amino acids were clustered in a very narrow range, all located in the small helix E next to the β tongue.

Figure 7:
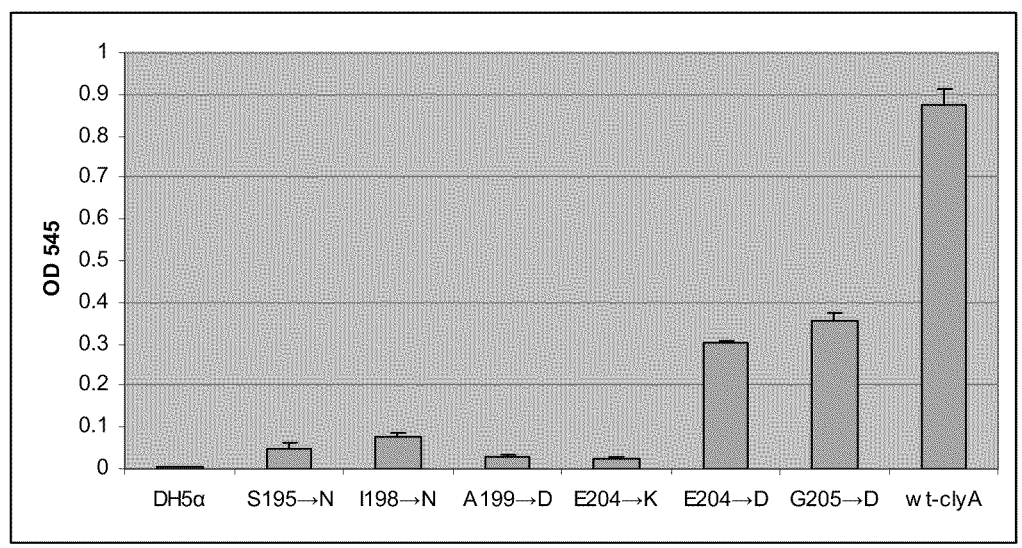
FIG. 7 shows the quantitated hemolytic activity of the ClyA single amino acid mutants. ClyA and its non-hemolytic mutants are expressed from plasmids derived from pSEC92gfpuv in *E. coli* DH5α.

The hemolytic activity of these 6 ClyA variants was then specifically measured (FIG. 7). Mutations S195N, I198N, A199D or E204K all dramatically reduced hemolytic activity to 2-8% of wt. A G205D mutation reduced the hemolytic activity to less than 50% of wt. Interestingly, an E204D substitution had much less effect (30% reduction) on the hemolytic activity versus the E204K substitution (reduction to less than 2% of wild-type), which clearly demonstrated the effect of different amino acids introduced into a given position within ClyA. These results showed that the functions of cytolysis and protein export can be uncoupled in ClyA. The uncoupling of these two functions can be achieved by mutation of single amino acid residues within a very small region of ClyA, i.e., amino acids in the small helix E adjacent to the β-tongue.

Construction of a Triple Mutant

Figure 8:
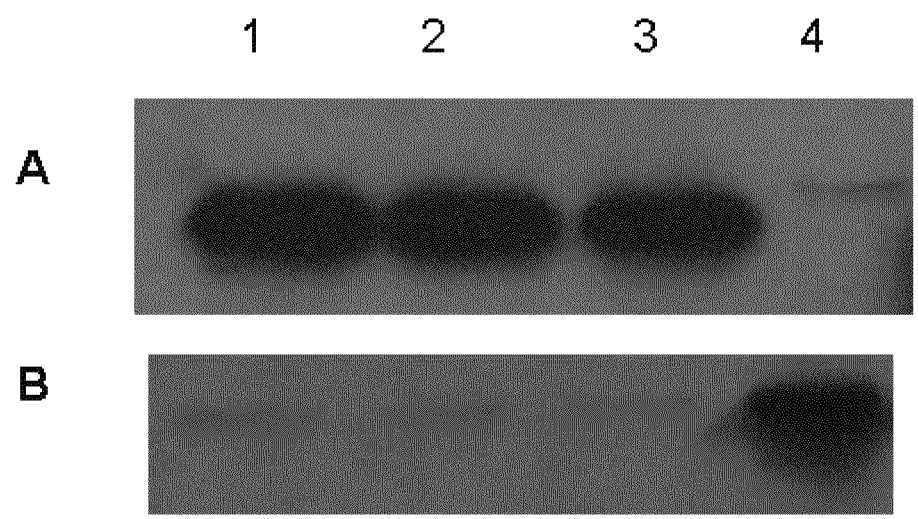
FIG. 8 shows immunoblots of ClyA non-hemolytic mutants. Wt ClyA (hemolytic) and non-hemolytic mutants are expressed in *Salmonella Typhi* CVD 908-htrA as fused proteins encoded by plasmids derived from pSEC92gfpuv. A. Detection of GFPuv in the culture supernatants of wt ClyA or ClyA non-hemolytic mutants. B. Detection of GroEL in the culture supernatants. 1, clyA non-hemolytic mutant carrying the mutation I198→N. 2, wt ClyA. 3, ClyA triple non-hemolytic triple mutant carrying I198→N, A199→D, E204→K. 4, whole cell extract of *Salmonella Typhi* CVD 908-htrA without plasmid.
Figure 9:
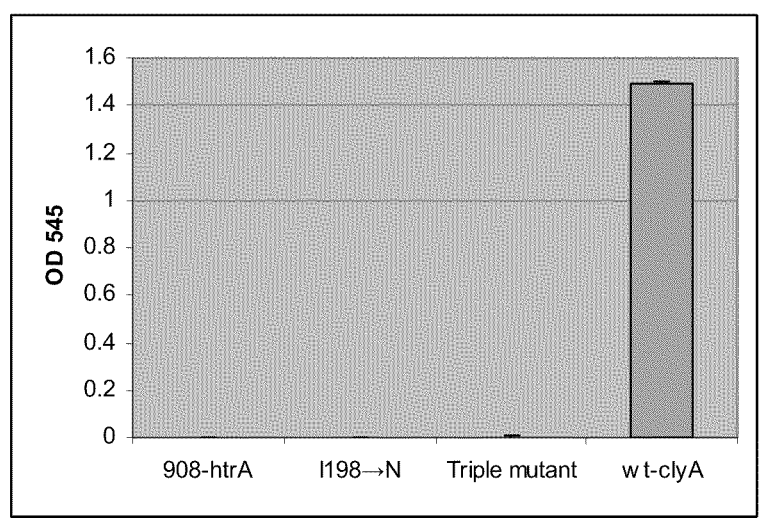
FIG. 9 shows the hemolytic activity of the non-hemolytic clyA triple mutant (I198→N, A199→D and E204→K) expressed in *Salmonella Typhi* CVD 908-htrA from plasmid pSEC93-gfp.

Using the results from above, the codon-optimized clyA gene in pSEC92gfpuv was then re-engineered to contain the triple mutation: I198N, A199D, E204K (SEQ ID NO:31), creating pSEC93gfpuv. Since each of these single mutations substantially reduced hemolytic activity while having no apparent effect on export, it was expected that the combination of these 3 mutations would completely abolish hemolytic activity. Export of the triple mutant ClyA::GFPuv fusion was tested by immunoblot (FIG. 8A). The results showed that export of the triple mutant from the live vector vaccine strain CVD908-htrA was virtually indistinguishable from wt ClyA::GFPuv fusions, and assays of hemolytic activity confirmed that this triple mutant had no cytolytic activity with erythrocytes (FIG. 9). Again, the absence of GroEL in the supernatants strongly suggests that ClyA variant fusions are being efficiently exported into the supernatant in the absence of detectable autolysis (FIG. 8B).

Immunogenicity of Exported Fusion Proteins

In a preferred embodiment, these non-hemolytic mutants will be fused to antigens other than GFPuv, for the purpose of developing live vector vaccines against human pathogens, including but not limited to full-length Protective Antigen PA83 from anthrax toxin. Therefore, it is critical to assess if fusions of non-hemolytic ClyA remain immunogenic, with relevant immune responses (protective humoral and/or cellular responses) able to target the downstream foreign domain.

Figure 10:
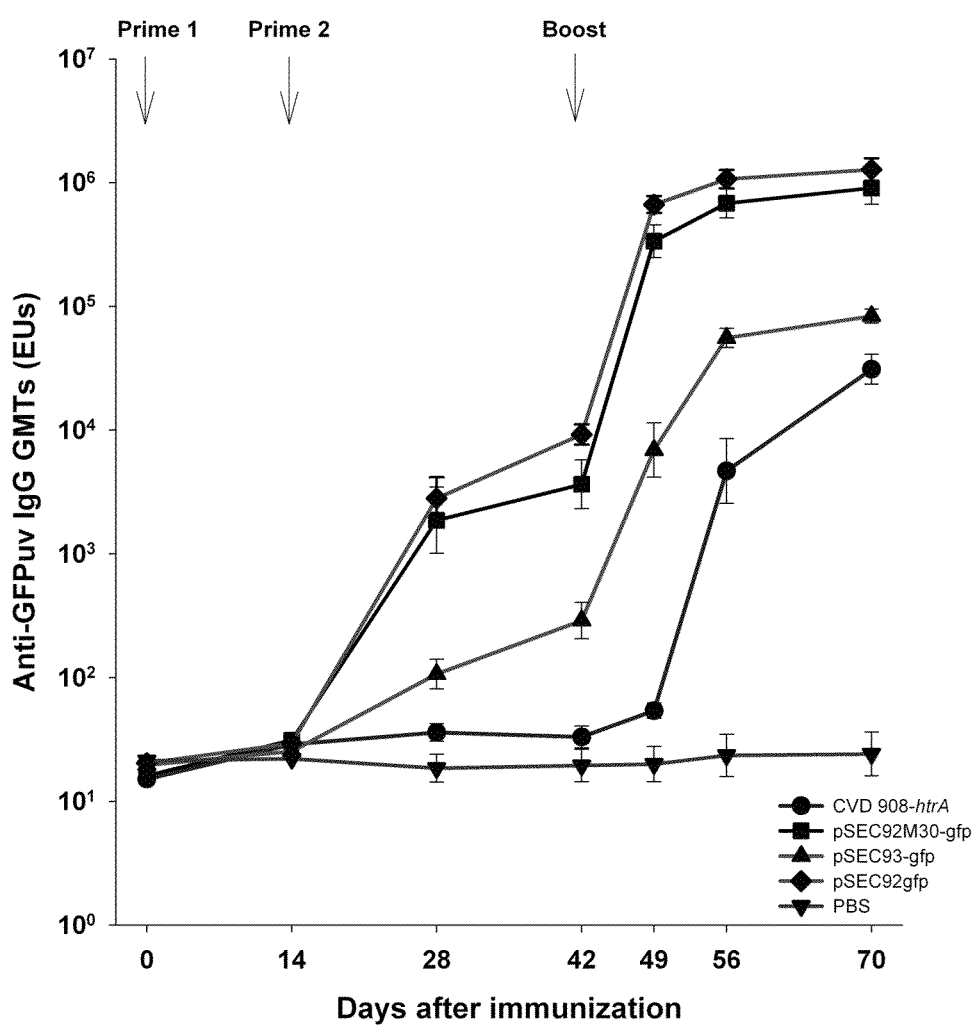
FIG. 10 shows the results of an immunogenicity experiment in which mice were immunized intranasally with two doses ($10^9$ colony forming units [CFUs] per dose) of CVD 908-htrA attenuated live vector strains carrying plasmids derived from pSEC92gfpuv that express non-hemolytic ClyA::GFPuv fusion variant proteins. All mice were boosted intramuscularly with purified GFPuv on day 42. Results are reported as geometric mean titers (in ELISA units [EU]) of serum IgG against the GFPuv domain of ClyA::GFPuv.

The immunogenicity of variant non-hemolytic ClyA::GFPuv protein fusions was therefore tested in mice. Mice were immunized intranasally with two doses ($10^9$ colony forming units [CFUs] per dose) of CVD908-htrA attenuated live vector strains carrying plasmids derived from pSEC92gfpuv that express non-hemolytic variant ClyA-GFPuv fusion proteins. All mice were boosted intramuscularly with purified GFPuv on day 42. Results are reported in FIG. 10 as geometric mean titers (in ELISA units [EU]) of serum IgG against the GFPuv domain of ClyA::GFPuv. It is immediately obvious that the immunogenicity of the triple mutant of ClyA encoded by pSEC93gfpuv (containing the 3 amino acid substitutions I198N, A199D, E204K) is not as immunogenic as the non-hemolytic variant expressed by pSEC92M30gfpuv (expressing a non-hemolytic mutant containing the single substitution I198N). As expected, unaltered ClyA-GFPuv expressed from strains carrying the original pSEC92gfpuv provides the highest GFPuv-specific humoral immunity, but the immunogenicity of the M30 non-hemolytic mutant (I198N) is comparable. The results of this critical experiment clearly demonstrate that although it is possible to genetically remove hemolytic activity from ClyA while preserving its export capabilities, subtle changes introduced into the structure of ClyA::GFPuv fusion proteins as substitutions of residues accumulate can dramatically affect the immunogenicity of these fusion proteins.

Example 7

Construction and Analysis of Additional Non-Hemolytic Variants of *S. Typhi* ClyA Each of the mutations created in the triple mutant (pSEC93gfpuv) discussed in Example 6 was derived from adjacent loci in the αE domain which may cause changes in the conformation of GFPuv protein (or other downstream fusion domain) expressed by the plasmid. Therefore, an additional strategy to alter the hemolytic activity of the ClyA protein was designed.

Construction of pSEC91-83-Derived Plasmids

Rather than optimize the non-hemolytic ClyA strategy using pSEC92gfpuv, point mutations were introduced into a previously described expression plasmid, pSEC91-83, encoding ClyA fused to the Protective Antigen (PA83) from anthrax toxin, to abolish ClyA hemolytic activity (Galen et al, 2009. J. Infect. Dis. 199:326-35). Because the single mutation (I198N) induced a level of anti-GFP IgG that was comparable to the positive control, this mutation comprised the primary mutation with which one other mutation was tested. Three derivatives of pSEC91-83 were constructed as follows:

1) Single mutant 1=I198N introduced into clyA of pSEC91-83 to create pSEC91-83I198N.

2) Single mutant 2=C285W introduced into clyA of pSEC91-83 to create pSEC91-83C285W; this location had previously been established as abolishing hemolytic activity of the ClyA protein (Kim et. al. (2008); Table 4 herein, clone M148).

3) Double Mutant (DM)—I198N and C285W introduced into clyA of pSEC91-83 to create pSEC91-83DM.

Two pairs of primers were designed to introduce the mutations into clyA encoded by pSEC91-83 using standard site-directed mutagenesis procedures:

```
1) I198N
G873:
                                         (SEQ ID NO: 33)
5'-TATTTCCTATTCTAATGCTGCGGGCGTGATTGAAGG-3'

G874:
                                         (SEQ ID NO: 34)
5'-CCTTCAATCACGCCCGCAGCATTAGAATAGGAAATA-3'

2) C285W
G875:
                                         (SEQ ID NO: 35)
5'-TGATTAACACCTGGAATGAATACCAACAACGTCATGG-3'
G876:
                                         (SEQ ID NO: 36)
5'-CCATGACGTTGTTGGTATTCATTCCAGGTGTTAATCA-3'
```

Each of the three constructs (pSEC91-83I198N, pSEC91-83C285W, and pSEC91-83DM) was successfully constructed and transformed into CVD908htrA live vector. However, initial results suggested that the strains were not stable using the pSEC91-83 backbone. Therefore, another backbone incorporating the SSB stabilizing system was selected for further engineering (pGEN222SXbaI).

Construction of CVD908htrA-ssb(pS-CPA83) Clones

Figure 16:
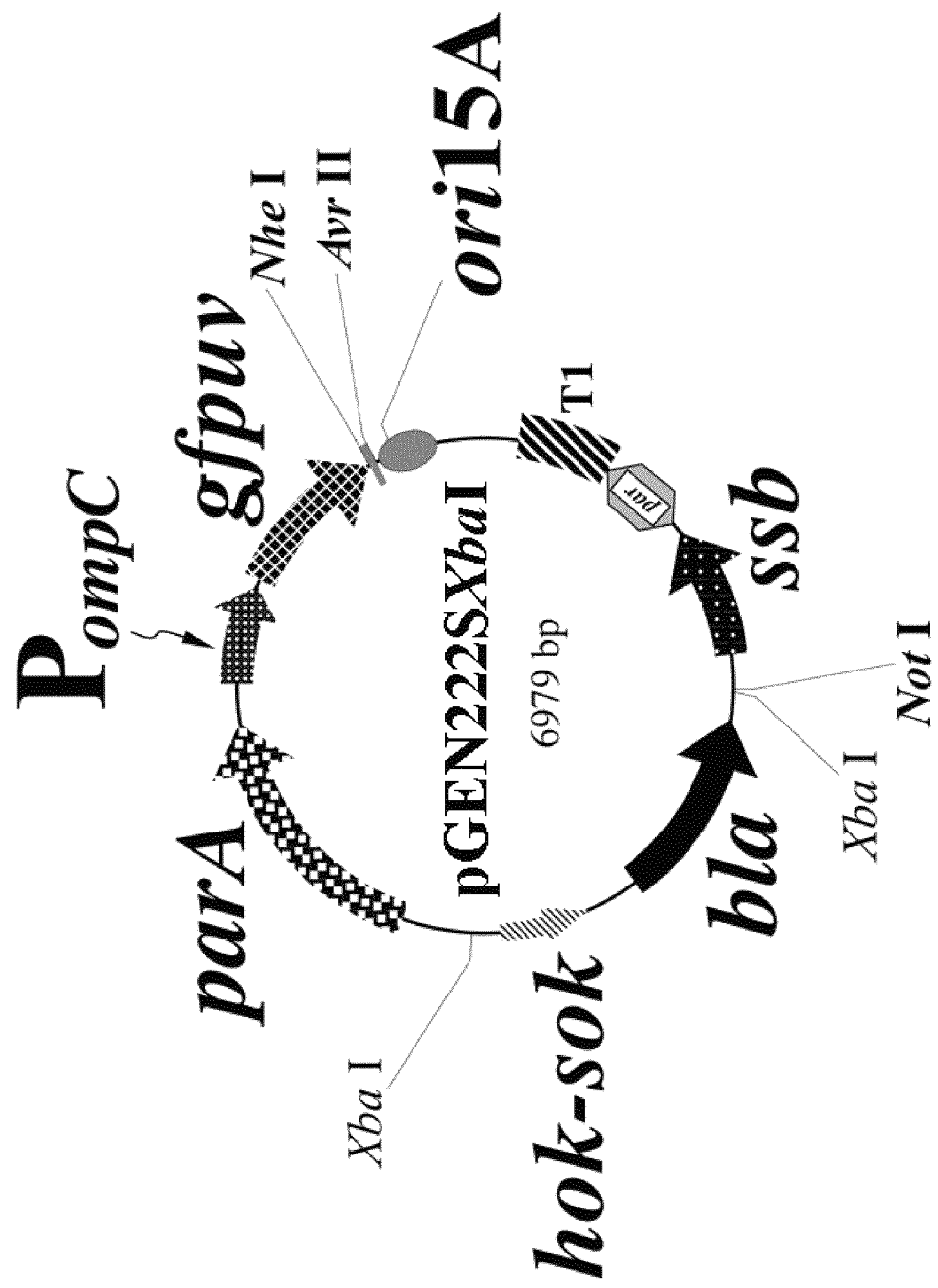

The pGEN222SXbaI (FIG. 16) is a derivative of the previously described pGEN222 plasmid (Galen et al. 1999. Infect. Immun. 67: 6424-33) into which the SSB stabilization system was introduced. To engineer this medium copy plasmid, the ssb cassette used in the construction of the temporary maintenance plasmid pBRmSSB was first excised from pCV546 as a 798 bp Xba I-Nhe I cassette and inserted into a derivative of pGEN222, destroying the unique Spe I site and creating pGEN222S. Since ssb will effectively function as a post-segregational killing function in vivo, inclusion of hok-sok was no longer necessary, so the Xho I site 5'-proximal to hok-sok was changed by site-specific mutagenesis to an Xba I site, creating pGEN222SXbaI for future deletion of both hok-sok and bla.

A special cassette was also designed and created to allow simple selection of plasmids prior to introduction into CVD 908-htrAssb strains. This cassette was comprised of a tetracycline gene flanked by FRT recombination sites, referred to here as FRT-tetA-FRT and flanked by the restriction sites Xba I and Not I. This FRT-tetA-FRT Xba I-Not I cassette was generated using the following primers with pSEC91 as the template DNA:

```
FRT-tetA-forward:
                                         (SEQ ID NO: 37)
TCTAGAgaagttcctattctatatatagtataggaacttcGCTAGCTCAT
GTTTGACAGCTTATCATCGATAAGCTTTAATGCGGTAGTTTATCAC FRT-tetA-reverse:
                                         (SEQ ID NO: 38)
TCTAGAgaagttcctatactatatatagaataggaacttcGCTAGCCTAT
CAGGTCGAGGTGGCCCGGCTCCATGCACCGCGACGCAACGCGGGGAG
```

This FRT-tetA-FRT cassette was recovered in pCR-BLUNT II-TOPO for easy excision as a 1397 bp Xba I-Not I fragment.

The following steps were undertaken in the construction of the expression vectors using the pGEN222SXbaI backbone. In separate constructs, the mutated clyA alleles were subcloned from pSEC91-83I198N, pSEC91-83C285W, and pSEC91-83DM by digestion with BamHI and AvrII, and ligation into pGEN222SXbaI cleaved with the same restriction enzymes, creating pGEN222SXbaI-I198N, pGEN222SXbaI-C285W and pGEN222SXbaII-DM.

Next, the bla-hok-sok cassettes of the resulting pGEN222SXbaI-I198N, pGEN222SXbaI-C285W and pGEN222SXbaII-DM plasmids were replaced with the FRT-tetA-FRT cassette by digesting pCR-BLUNT II-TOPO containing FRT-tetA-FRT with XbaI and NotI, and inserting this 1397 bp fragment into identically cleaved pGEN222SXbaI-I198N, pGEN222SXbaI-C285W and pGEN222SXbaII-DM plasmids, creating the tetracycline-resistant constructs, designated as below:

1) pTS-CPA83-I198N—Single Mutant 1
2) pTS-CPA83-C285W—Single Mutant 2
3) pTS-CPA83-DM—Double Mutant These constructs were recovered in DH5αΔssb.

Next, the pCP20 plasmid was introduced into the these three strains to induce excision of the tetracycline gene cassette using identical methodology to that used to delete ssb from the chromosomes of both DH5αΔssb and CVD 908-htrAssb.

Figure 12:
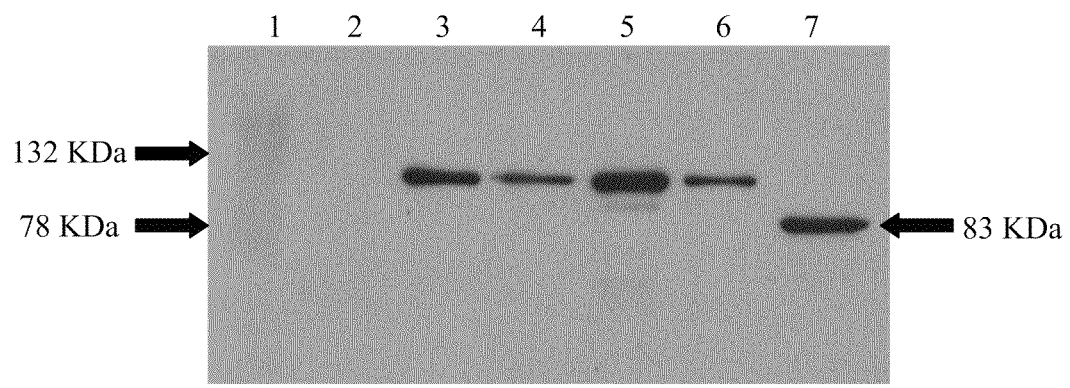
FIG. 12 shows immunoblots of clyA non-hemolytic mutants. Lane 1—Kaleidoscope protein marker; lane 2—CVD908htrA; lane 3—CVD908htrA(pSEC91-83); lane 4—CVD908-htrAssb(pS-CPA83-I198N)—Single Mutant 1; lane 5—CVD908-htrAssb(pS-CPA83-C285W)—Single Mutant 2; lane 6—CVD908-htrAssb(pS-CPA83-DM)—Double Mutant; lane 7—PA83 purified protein (250 ng).

Finally, the resulting constructs having a SSB stabilizing system and lacking antibiotic resistance markers were transformed into CVD908-htrAssb and designated as follows:

1) CVD908-htrAssb (pS-CPA83-I198N)—Single Mutant 1
2) CVD908-htrAssb (pS-CPA83-C285W)—Single Mutant 2
3) CVD908-htrAssb (pS-CPA83-DM)—Double Mutant Western immunoblot analysis for detection of fusion protein expression was carried out as described (Galen et al, 2009. J, Infect. Dis. 199:326-35). Whole cell lysates expressing ClyM-PA83 fusions were separated on SDS-polyacrylamide gels. Detection of PA83 fusion proteins of ~117 kDa relative molecular weight was carried out using goat anti-PA polyclonal IgG (List Biological Laboratories, Campbell, Calif.) and horseradish peroxidase (HRP)-labeled rabbit anti-goat IgG (Kirkegaard & Perry Labs, Inc., Gaithersburg, Md.). Immunoblots were developed using the ECL+Plus detection system (Amersham Biosciences, Piscataway, N.J.) and blots exposed to Kodak X-OMAT XAR-2 film. The results of the immunoblots are shown in FIG. 12.

Figure 13:
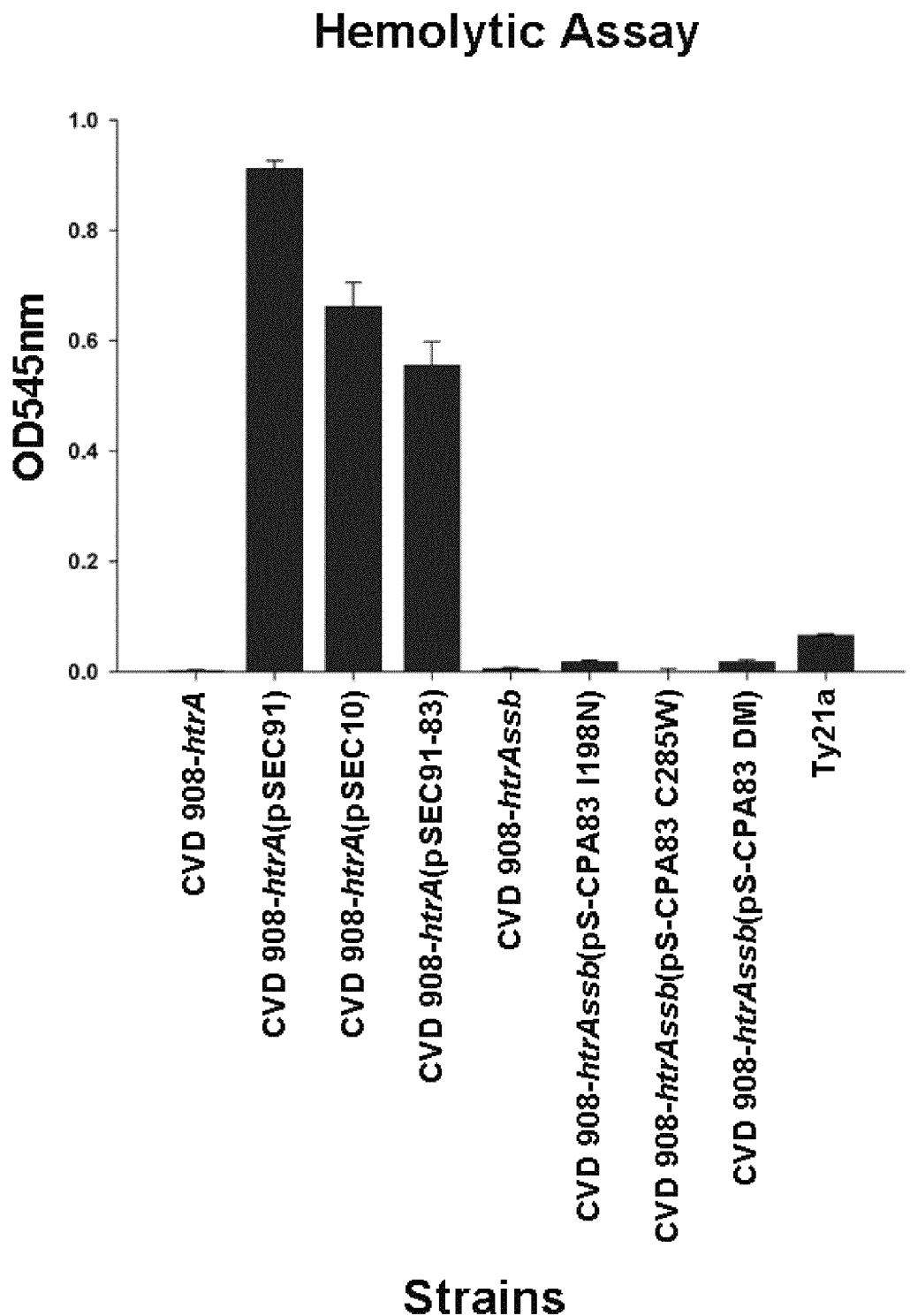
FIG. 13 shows the quantitated hemolytic activity of the ClyA single and double amino acid mutants. ClyA and its non-hemolytic mutants are expressed from different plasmids in CVD908htrA and CVD908-htrA-ssb.

Measurement of hemoglobin release from erythrocytes was performed as described (Sansonetti et al. 1986. *Infect. Immun.* 51: 461-9), with several modifications. Bacteria were cultured to late log phase (OD600 at 0.9-1.0) and harvested. $1 \times 10^9$ cells in 50 ul PBS were mixed with equal volume of washed sheep erythrocytes (Lampire Biological, Pipersville, Pa.) in the concentration of $4 \times 10^9$/ml. The mixture was centrifuged at 2,200×g for 15 min at 30° C. and then incubated at 37° C. for two hours. The reaction was resuspended by adding 150 ul of cold PBS and then centrifuged at 2,200×g for 15 min at 4° C. At the end of the reaction, 100 μl of supernatant was transferred to a flat bottom microtiter plate. Hemolytic activity was measured by reading the optical density at 545 nm in a Versamax microplate reader (Molecular Devices, Toronto, Canada). The results of the assay are shown in FIG. 13. The pSEC10, pSEC91 and pSEC91-83 each express unmodified ClyA. The strain Ty21a is the currently licensed typhoid vaccine strain; not surprisingly that it displays slight hemolytic activity, as noted previously by Oscarsson et al (Oscarsson et al. 2002. Infect. Immun. 70:5759-5769). These results clearly demonstrate that the hemolytic activity of each of the three pS-CPA83 constructs (I198N, C285W and DM) was abolished.

To compare the immunogenicity between the constructs expressing PA83 fused to wildtype ClyA (i.e. strain CVD 908-htrA(pSEC91-83)) versus PA83 delivered by strains expressing SSB-stabilized ClyA variants (i.e. CVD908-htrAssb (pS-CPA83-I198N), CVD908-htrAssb (pS-CPA83-C285W), and CVD908-htrAssb (pS-CPA83-DM)), BALB/c (H2d) female mice were immunized intranasally over 7 weeks as described in Table 5.

TABLE 5

| Group | Total mice | $1^{st}$ prime (October 22, 2008) $1\times10^9$ CFU/10 µl | $2^{nd}$ prime (November 5, 2008) $1\times10^9$ CFU/10 µl | $3^{rd}$ booster* (December 3, 2008) |
|---|---|---|---|---|
| 1 Cages (A, B) | 10 | CVD908htrA (Intra-nasal) | CVD908htrA (Intra-nasal) | PA protein plus alhydrogel (Intra-muscular) |
| 2 Cages (C, D) | 10 | CVD908htrA (pSEC91-83) (Intra-nasal) | CVD908htrA (pSEC91-83) (Intra-nasal) | PA protein plus alhydrogel (Intra-muscular) |
| 3 Cages (E, F) | 10 | CVD908htrA (Single mutant 1 pS-CPA83-I198N) (Intra-nasal) | CVD908htrA (Single mutant 1 pS-CPA83-I198N) (Intra-nasal) | PA protein plus alhydrogel (Intra-muscular) |
| 4 Cages (G, H) | 10 | CVD908htrA (Single mutant 2 pS-CPA83-C285W) (Intra-nasal) | CVD908htrA (Single mutant 2 pS-CPA83-C285W) (Intra-nasal) | PA protein plus alhydrogel (Intra-muscular) |
| 5 Cages (I, J) | 10 | CVD908htrA (Double mutant pS-CPA83-DM) (Intra-nasal) | CVD908htrA (Double mutant pS-CPA83-DM) (Intra-nasal) | PA protein plus alhydrogel (Intra-muscular) |
| 6 Cages (K) | 5 | PBS (Intra-nasal) | PBS (Intra-nasal) | PBS (Intra-muscular) |

*PA 83 protein plus alhydrogel: 10 µg of PA 83 absorbed to 0.5 mg of alhydrogel per dose (50 µl)

Bleeding:

Pre-immunization: day −1 (October 21, 2008)

Post-Immunization: day 13 (November 4, 2008), 28 (November 19, 2008), 40 (December 1, 2008), 49 (December 10, 2008), 56 (December 17, 2008) and 70 (December 31, 2008)

The conditions under which the different inoculums were produced are shown as follows.
1) CVD 908htrA
(i) Streaked out from master stock on 2×LA+DHB and incubated at 30° C. for 48 hours
(ii) Inoculated 2-3 isolated colonies from plate in 5 ml 2×LB+DHB and incubated at 30° C. overnight
(iii) Sub-cultured 2.5 ml overnight culture (1:100) in 250 ml 2×LB+DHB and waited till the $OD_{600nm}$ reached ~1.4 at 37° C. (Approximately 4 h)
(vi) Spun down (6,000 rpm, 20 min), discarded all the supernatant and re-suspended in 300 µl PBS
(v) Diluted 1:1,000 for OD reading to make sure the $OD_{600nm}$~0.4-0.5
(vi) 10 µl for immunization (1-2×10$^9$CFU/10 µl)
2) CVD 908htrA(pSEC91-83)
(i) Streaked out from master stock on 2×LA+DHB+Kan (25 µg/ml) and incubated at 30° C. for 48 hours
(ii) Inoculated 2-3 colonies from plate in 25 ml 2×LB+DHB+Kan (25 µg/ml) and incubated at 30° C. for overnight
(iii) Sub-cultured 20 ml overnight culture (1:12.5) in 250 ml 2×LB+DHB+Kan (25 µg/ml) and waited till the $OD_{600nm}$ reached ~1.4 at 37° C. (Approximately 5 h 30 min)
(iv) Spun down (6,000 rpm, 20 min), discarded all the supernatant and re-suspended in 300 µl PBS
(v) Diluted 1:1,000 for OD reading to make sure the $OD_{600nm}$~0.4-0.5
(vi) 10 µl for immunization (1-2×10$^9$CFU/10 µl)
3) CVD 908htrA-ssb(pS-CPA83-I198N)=ClyA-Single Mutant 1 (I198N in pSSB Backbone)
(i) Streaked out from master stock on 2×LA+DHB and incubated at 30° C. for 48 hours
(ii) Inoculated 2-3 colonies from plate in 25 ml 2×LB+DHB and incubated at 30° C. for overnight
(iii) Sub-cultured 20 ml overnight culture (1:12.5) in 250 ml 2×LB+DHB and waited till the $OD_{600nm}$ reached ~1.4 at 37° C. (Approximately 5 h)
(iv) Spun down (6,000 rpm, 20 min), discarded all the supernatant and re-suspended in 150 µl PBS
(v) Diluted 1:1,000 for OD reading to make sure the $OD_{600nm}$~0.4-0.5
(vi) 10 µl for immunization (1-2×10$^9$CFU/10 µm)
4) CVD 908htrA-ssb(pS-CPA83-C285W)=ClyA-Single Mutant 2 (C285W in pSSB Backbone)
(i) Streaked out from master stock on 2×LA+DHB and incubated at 30° C. for 48 hours
(ii) Inoculated 2-3 colonies from plate in 30 ml 2×LB+DHB and incubated at 30° C. for overnight
(iii) Sub-cultured 20 ml overnight culture (1:12.5) in 250 ml 2×LB+DHB and waited till the $OD_{600nm}$ reached ~1.4 at 37° C. (Approximately 5 h)
(iv) Spun down (6,000 rpm, 20 min), discarded all the supernatant and re-suspended in 150 µl PBS
(v) Diluted 1:1,000 for OD reading to make sure the $OD_{600nm}$~0.4-0.5
(vi) 10 µl for immunization (1-2×10$^9$CFU/10 µl)
5) CVD 908htrA-ssb(pS-CPA83-DM)=ClyA-Double Mutant (I198N and C285W in pSSB Backbone
(i) Streaked out from master stock on 2×LA+DHB and incubated at 30° C. for 48 hours
(ii) Inoculated 2-3 colonies from plate in 30 ml 2×LB+DHB and incubated at 30° C. for overnight
(iii) Sub-cultured 20 ml overnight culture (1:12.5) in 250 ml 2×LB+DHB and waited till the $OD_{600nm}$ reached ~1.4 at 37° C. (Approximately 5 h)
(iv) Spun down (6,000 rpm, 20 min), discarded all the supernatant and re-suspended in 150 µl PBS
(v) Diluted 1:1,000 for OD reading to make sure the $OD_{600nm}$~0.4-0.5
(vi) 10 µl for immunization (1-2×10$^9$CFU/10 µl)

Figure 14:
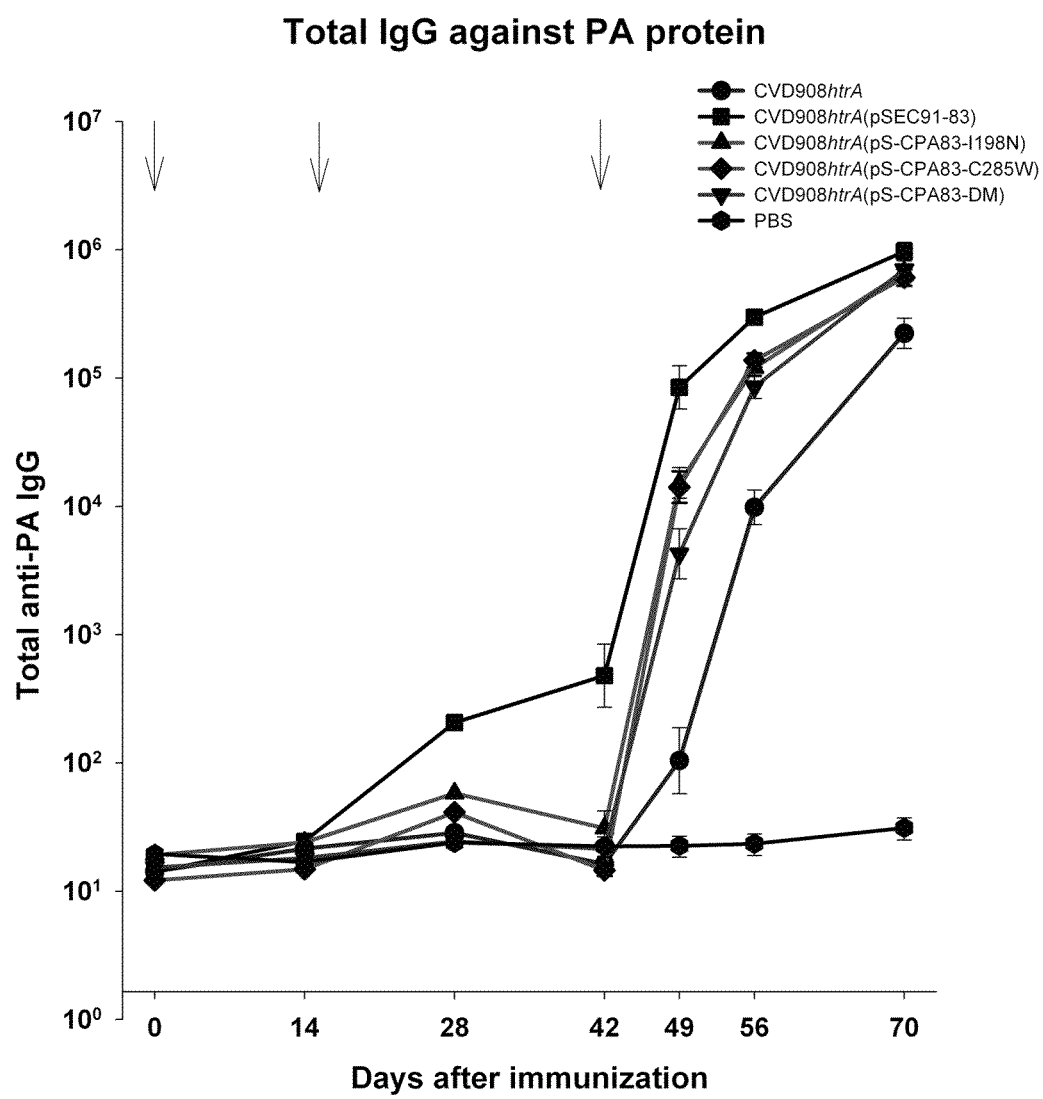
FIG. 14 shows the results of an immunogenicity experiment in which mice were immunized intranasally with two doses ($10^9$ colony forming units [CFUs] per dose) of CVD 908-htrA attenuated live vector strains carrying plasmids derived from pGEN222A3s that express non-hemolytic ClyA::PA83 fusion variant proteins. All mice were boosted intramuscularly with PA83 protein plus alhydrogel. Results are reported as geometric mean titers (in Castillo. 1997. The *Escherichia coli* K-12 sheA gene encodes a 34-kDa secreted haemolysin. Mol. Microbiol. 25:107-115). Ludwig and colleagues have reported that secretion of this cryptic hemolysin is accompanied by leakage of periplasmically confined proteins, but is not accompanied by loss of cytoplasmic proteins, arguing against outright cell lysis to release HlyE (Ludwig, A., S. Bauer, R. Benz, B. Bergmann, and W. Goebel. 1999. Analysis of the SlyA-controlled expression, subcellular localization and pore-forming activity of a 34 kDa haemolysin (ClyA) from *Escherichia coli* K-12. Mol. Microbiol. 31:557-567).

Total serum anti-PA831 g was measure by ELISA as previously described (Galen et al, 2009. J, Infect. Dis. 199:326-35). Plates were coated with PA83 (List Biological) at 2 µg/ml in PBS and blocked with 10% dry-milk in PBS. Duplicate samples were tested in serial dilutions. HRP-labeled anti-monkey IgG (KPL) was used as the conjugate, followed by TMB substrate (KPL). Anti-PA IgG titers were calculated by interpolation of regression corrected Absorbance values of experimental samples into a standard curve. The results are shown in FIG. 14. Further, FIG. 15 provides a table showing a comparison of the percentage of mice with seroconversion and GMTs after vaccination with attenuated S. Typhi live vectors carrying plasmids delivering PA83 fused to wild-type ClyA and the non-hemolytic ClyA variants. These data indicate that although both single mutant and double mutant ClyA variants elicit less PA83-specific humoral immunity 7 days after boosting, levels become indistinguishable from the immunogenicity of wildtype ClyA-PA83 4 weeks after boosting (day 70) and are significantly different than for mice primed with empty live vector and boosted with PA83 (group 1). The results clearly demonstrate that non-hemolytic ClyM variants can still preserve the immunogenicity of foreign proteins fused to the carboyl terminus of ClyM.

All U.S. and foreign patents, patent applications, and non-patent literature (including, but not limited to, abstracts, scientific journal articles, books and manuals) referred to or cited herein are hereby incorporated by reference in their entireties.

While the disclosure above describes the invention in detail and with reference to specific embodiments thereof, it will be apparent to one of ordinary skill in the art that various changes and modifications can be made therein without departing from the spirit and scope thereof.

REFERENCES

Atkins, A., N. R. Wyborn, A. J. Wallace, T. J. Stillman, L. K. Black, A. B. Fielding, M. Hisakado, P. J. Artymiuk, and J. Green. 2000. Structure-function relationships of a novel bacterial toxin, hemolysin E. The role of $α_G$ J. Biol. Chem. b:41150-41155.
Bailey, J. E., Host-vector interactions in Escherichia coli, p. 29-77. In A. Fiechter (ed.), Advances in Biochemical Engineering. Biotechnology. Springer-Verlag, Berlin (1993).
Balbas, P., X. Soberon, E. Merino, M. Zurita, H. Lomeli, F. Valle, N. Flores, and F. Bolivar. 1986. Plasmid vector pBR322 and its special-purpose derivatives—a review. Gene 50:3-40.
Blomfield, I. C., V. Vaughn, R. F. Rest, and B. I. Eisenstein. 1991. Allelic exchange in Escherichia coli using the Bacillus subtilis sacB gene and a temperature-sensitive pSC101 replicon. Mol. Microbiol. 5:1447-1457.
Boe, L., K. Gerdes, and S. Molin. 1987. Effects of genes exerting growth inhibition and plasmid stability on plasmid maintenance. J. Bacteriol. 169:4646-4650.
Borchert, T. V. and V. Nagarajan. 1991. Effect of signal sequence alterations on the export of levansucrase in Bacillus subtilis. J. Bacteriol. 173:276-282.
Bramucci, M. G. and V. Nagarajan. 1996. Direct selection of cloned DNA in Bacillus subtilis based on sucrose-induced lethality. Appl. Environ. Microbiol. 62:3948-3953.
Chervaux, C., N. Sauvonnet, A. Le Clainche, B. Kenny, A. L. Hunt, J. K. Broome-Smith, and I. B. Holland. 1995. Secretion of active β-lactamase to the medium mediated by the *Escherichia coli* haemolysin transport pathway. Mol. Gen. Genet. 249:237-245.

Corchero, J. L. and A. Villayerde. 1998. Plasmid maintenance in *Escherichia coli* recombinant cultures is dramatically, steadily, and specifically influenced by features of the encoded proteins. Biotechnol. Bioeng. 58:625-632.

Cserjan-Puschmann, M., W. Kramer, E. Duerrschmid, G. Streidner, and K. Bayer. 1999. Metabolic approaches for the optimisation of recombinant fermentation processes. Appl. Microbiol. Biotechnol. 53:43-50.

Datta, N. and P. Kontomichalou. 1965. Penicillinase synthesis controlled by infectious R factors in Enterobacteriaceae. Nature 208:239-241.

Dedonder, R. 1966. Levansucrase from *Bacillus subtilis*, p. 500-505. In E. F. Neufeld and V. Ginsburg (eds.), Methods in Enzymology. Academic Press, New York.

del Castillo, F. J., S. C. Leal, F. Moreno, and I. del Castillo. 1997. The *Escherichia coli* K-12 sheA gene encodes a 34-kDa secreted haemolysin. Mol. Microbiol. 25:107-115.

Fouet, A., M. Arnaud, A. Klier, and G. Rapoport. 1984. Characterization of the precursor form of the exocellular levansucrase from *Bacillus subtilis*. Biochem. Biophys. Res. Commun. 119:795-800.

Galen, J. E., O. G. Gomez-Duarte, G. Losonsky, J. L. Halpern, C. S. Lauderbaugh, S. Kaintuck, M. K. Reymann, and M. M. Levine. 1997. A murine model of intranasal immunization to assess the immunogenicity of attenuated *Salmonella typhi* live vector vaccines in stimulating serum antibody responses to expressed foreign antigens. Vaccine 15:700-708.

Galen, J. E. and M. M. Levine. 2001. Can a 'flawless' live vector vaccine strain be engineered? Trends in Microbiology 9:372-376.

Galen, J. E., J. Nair, J. Y. Wang, S. S. Wasserman, M. K. Tanner, M. Sztein, and M. M. Levine. 1999. Optimization of plasmid maintenance in the attenuated live vector vaccine strain *Salmonella typhi* CVD 908-htrA. Infect. Immun. 67:6424-6433.

Gay, P., D. Le Coq, M. Steinmetz, T. Berkelman, and C. I. Kado. 1985. Positive selection procedure for entrapment of insertion sequence elements in Gram-negative bacteria. J. Bacteriol. 164:918-921.

Gay, P., D. Le Coq, M. Steinmetz, E. Ferrari, and J. A. Hoch. 1983. Cloning structural gene sacB, which codes for exoenzyme levansucrase of *Bacillus subtilis*: expression of the gene in *Escherichia coli*. J. Bacteriol. 153:1424-1431.

Glick, B. R., Biotechnol. Adv. 13:247-261 (1995).

Han, Y. W. 1990. Microbial levan. Advances in Applied Microbiology 35:171-194.

Harcum and Bentley. 1993. Biotechnol. Bioeng. 42:675-685.

Hone, D. M., A. M. Harris, S. Chatfield, G. Dougan, and M. M. Levine. 1991. Construction of genetically defined double aro mutants of *Salmonella typhi*. Vaccine 9:810-816.

Jung, H., J. Lebeault, and J. Pan. 1998. Surface display of *Zymomonas mobilis* levansucrase by using the ice-nucleation protein of *Pseudomonas syringae*. Nat. Biotechnol. 16:576-580.

Lattemann, C. T., J. Maurer, E. Gerland, and T. F. Meyer. 2000. Autodisplay: functional display of active β-lactamase on the surface of *Escherichia coli* by the AIDA-I autotransporter. J. Bacteriol. 182:3726-3733.

Le Coq, D., P. Ratet, M. Steinmetz, and P. Gay. 1984. A genetic approach to levansucrase secretion in *Bacillus subtilis*, p. 141-152. In A. T. Ganesan and J. A. Hoch (eds.), Genetics and biotechnology of bacilli. Academic Press, New York.

LeBrun, E. and R. van Rapenbusch. 1980. The structure of *Bacillus subtilis* levansucrase at 3.8 A resolution. J. Biol. Chem. 255:12034-12036.

Ludwig, A., S. Bauer, R. Benz, B. Bergmann, and W. Goebel. 1999. Analysis of the SlyA-controlled expression, subcellular localization and pore-forming activity of a 34 kDa haemolysin (ClyA) from *Escherichia coli* K-12. Mol. Microbiol. 31:557-567.

Matthew, M. and R. W. Hedges. 1976. Analytical isoelectric focusing of R factor-determined β-lactamases: correlation with plasmid compatibility. J. Bacteriol. 125:713-718.

McDermott, P. J., P. Gowland, and P. C. Gowland. 1993. Adaptation of *Escherichia coli* growth rates to the presence of pBR322. Lett. Appl. Microbiol. 17:139-143.

Orr, N., J. E. Galen, and M. M. Levine. 1999. Expression and immunogenicity of a mutant diphtheria toxin molecule, $CRM_{197}$, and its fragments in *Salmonella typhi* vaccine strain CVD 908-htrA. Infect. Immun. 67:4290-4294.

Oscarsson, J., Y. Mizunoe, L. Li, X. Lai, A. Wieslander, and B. E. Uhlin 1999. Molecular analysis of the cytolytic protein ClyA (SheA) from *Escherichia coli*. Mol. Microbiol. 32:1226-1238.

Oscarsson, J., Y. Mizunoe, B. E. Uhlin, and D. J. Haydon. 1996. Induction of haemolytic activity in *Escherichia coli* by the slyA gene product. Mol. Microbiol. 20:191-199.

Pecota, D. C., C. S. Kim, K Wu, K. Gerdes, and T. K. Wood. 1997. Combining the hok/sok, parDE, and pnd postsegregational killer loci to enhance plasmid stability. Appl. Environ. Microbiol. 63:1917-1924.

Pluckthun, A. and J. R. Knowles. 1987. The consequences of stepwise deletions from the signal-processing site of β-lactamase. J. Biol. Chem. 262:3951-3957.

Ried, J. and A. Collmer. 1987. An npI-sacB-sacR cartridge for constructing directed, unmarked mutations in Gram-negative bacteria by marker exchange-eviction mutagenesis. Gene 57:239-246.

Sambrook, J., E. F. Fritsch, and T. Maniatis. 1989. AnonymousMolecular cloning: a laboratory manual. Cold Spring Harbor Laboratory Press, Cold Spring Harbor, N.Y.

Sambrook, J. and D. W. Russell. 2001. Expression of cloned genes in *Escherichia coli*, p. 15.35AnonymousMolecular cloning. A laboratory manual. Cold Spring Harbor Laboratory Press, Cold Spring Harbor.

Shaw, K. J., P. N. Rather, R. S. Hare, and G. H. Miller. 1993. Molecular genetics of aminoglycoside resistance genes and familial relationships of the aminoglycoside-modifying enzymes. Microbiol. Rev. 57:138-163.

Smith & Bidochka. Can. J. Microbiol. 44:351-355 (1998).

Steinmetz, M., D. Le Coq, H. B. Djemia, and P. Gay. 1983. Genetic analysis of sacB, the structural gene of a secreted enzyme, levansucrase of *Bacillus subtilis* Marburg. Mol. Gen. Genet. 191:138-144.

Summers, D. K. 1998. Timing, self-control and sense of direction are the secrets of multicopy plasmid stability. Mol. Microbiol. 29:1137-1145.

Sutcliffe, J. G. 1978. Nucleotide sequence of the ampicillin resistance gene of *Escherichia coli* plasmid pBR322. Proceedings of the National Academy of Sciences USA 75:3737-3741.

Tacket, C. O., M. Sztein, G. Losonsky, S. S. Wasserman, J. P. Nataro, R. Edelman, D. Pickard, G. Dougan, S. Chatfield, and M. M. Levine. 1997. Safety of live oral *Salmonella typhi* vaccine strains with deletions in htrA and aroC aroD and immune responses in humans. Infect. Immun. 65:452-456.

Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.

Wang, J. Y., F. Noriega, J. E. Galen, E. M. Barry, and M. M. Levine. 2000. Constititive expression of the Vi polysaccharide capsular antigen in attenuated *Salmonella enterica* serovar *Typhi* oral vaccine strain CVD 909. Infect. Immun. 68:4647-4652.

Wang, J. Y., M. F. Pasetti, F. Noriega, R. J. Anderson, S. S. Wasserman, J. E. Galen, M. Sztein, and M. M. Levine. 2001. Construction, genotypic and phenotypic characterization, and immunogenicity of attenuated DguaBA *Salmonella enterica* serovar *Typhi* strain CVD 915. Infect. Immun. 69:4734-4741.

Wu, K. and T. K Wood. 1994. Evaluation of the hok/sok killer locus for enhanced plasmid stability. Biotechnol. Bioeng. 44:912-921.

What is claimed is:

1. A method for producing a fusion protein, comprising:
   (a) transforming a population of bacteria with an expression vector encoding a fusion protein, wherein said fusion protein comprises a protein of interest linked to the carboxy terminus of an export protein, wherein said export protein is a *Salmonella enterica* serovar *Typhi* (*S. Typhi*) cytolysin A (ClyA) protein having substantially reduced hemolytic activity in comparison to the ClyA protein of SEQ ID NO:2, said export protein having the amino acid sequence set forth in SEQ ID NO:2 and having one or more mutations selected from the group consisting of an S195N mutation, an I198N mutation, an A199D mutation, an E204K mutation and a C285W mutation, and
   (b) culturing transformed bacteria of (a) in a culture medium under conditions such that said fusion protein is expressed and exported into the culture medium.

2. The method of claim 1, wherein said bacteria is selected from the group consisting of *Salmonella* spp., *Vibrio* spp., *Escherichia* spp., and *Shigella* spp.

3. The method of claim 1, wherein said bacteria is *S. Typhi*.

4. The method of claim 1, wherein said bacteria is *E. coli*, enterotoxigenic *E. coli* (ETEC) or enteroaggregative *E. coli* (EAEC).

5. The method of claim 1, wherein said bacteria is *Shigella flexneri* 2a.

6. The method of claim 1, wherein the protein of interest is an antigen.

7. The method of claim 1, further comprising collecting said fusion protein from the culture medium.

8. The method of claim 1, wherein said *S. Typhi* cytolysin A (ClyA) protein has the amino acid sequence set forth in SEQ ID NO:2 and has an S195N mutation.

9. The method of claim 1, wherein said *S. Typhi* cytolysin A (ClyA) protein has the amino acid sequence set forth in SEQ ID NO:2 and has an I198N mutation.

10. The method of claim 1, wherein said *S. Typhi* cytolysin A (ClyA) protein has the amino acid sequence set forth in SEQ ID NO:2 and has an A199D mutation.

11. The method of claim 1, wherein said *S. Typhi* cytolysin A (ClyA) protein has the amino acid sequence set forth in SEQ ID NO:2 and has an E204K mutation.

12. The method of claim 1, wherein said *S. Typhi* cytolysin A (ClyA) protein has the amino acid sequence set forth in SEQ ID NO:2 and has an C285W mutation.

13. The method of claim 1, wherein said *S. Typhi* cytolysin A (ClyA) protein has the amino acid sequence set forth in SEQ ID NO:2 and has a C285W mutation, and one additional mutation selected from the group consisting of an I198N mutation, an A199D mutation, and an E204K mutation.

14. The method of claim 1, wherein said *S. Typhi* cytolysin A (ClyA) protein has the amino acid sequence set forth in SEQ ID NO:2 and has an I198N mutation, an A199D mutation and an E204K mutation.

15. The method of claim 1, wherein said *S. Typhi* cytolysin A (ClyA) protein has the amino acid sequence set forth in SEQ ID NO:2 and has an I198N mutation and a C285W mutation.

16. The method of claim 1, wherein the protein of interest is anthrax toxin PA83 protein.

17. An expression vector comprising an expression cassette, wherein the expression cassette comprises an export protein coding sequence linked to a protein of interest coding sequence in a 5' to 3' arrangement, wherein said export protein is a *Salmonella enterica* serovar *Typhi* (*S. Typhi*) cytolysin A (ClyA) protein having substantially reduced hemolytic activity in comparison to the ClyA protein of SEQ ID NO:2, said export protein having the amino acid sequence set forth in SEQ ID NO:2 and having one or more mutations selected from the group consisting of an S195N mutation, an I198N mutation, an A199D mutation, an E204K mutation and a C285W mutation.

18. The expression vector of claim 17, wherein the protein of interest is an antigen.

19. The expression vector of claim 17, wherein said *S. Typhi* cytolysin A (ClyA) protein has the amino acid sequence set forth in SEQ ID NO:2 and has an S195N mutation.

20. The expression vector of claim 17, wherein said *S. Typhi* cytolysin A (ClyA) protein has the amino acid sequence set forth in SEQ ID NO:2 and has an I198N mutation.

21. The expression vector of claim 17, wherein said *S. Typhi* cytolysin A (ClyA) protein has the amino acid sequence set forth in SEQ ID NO:2 and has an A199D mutation.

22. The expression vector of claim 17, wherein said *S. Typhi* cytolysin A (ClyA) protein has the amino acid sequence set forth in SEQ ID NO:2 and has an E204K mutation.

23. The expression vector of claim 17, wherein said *S. Typhi* cytolysin A (ClyA) protein has the amino acid sequence set forth in SEQ ID NO:2 and has an C285W mutation.

24. The expression vector of claim 17, wherein said *S. Typhi* cytolysin A (ClyA) protein has the amino acid sequence set forth in SEQ ID NO:2 and has a C285W mutation, and one additional mutation selected from the group consisting of an I198N mutation, an A199D mutation, and an E204K mutation.

25. The expression vector of claim 17, wherein said *S. Typhi* cytolysin A (ClyA) protein has the amino acid sequence set forth in SEQ ID NO:2 and has an I198N mutation, an A199D mutation and an E204K mutation.

26. The expression vector of claim 17, wherein said *S. Typhi* cytolysin A (ClyA) protein has the amino acid sequence set forth in SEQ ID NO:2 and has an I198N mutation and a C285W mutation.

27. The expression vector of claim 17, wherein the protein of interest is anthrax toxin PA83 protein.

* * * * *

SEQUENCE LISTING

<160> NUMBER OF SEQ ID NOS: 41

<210> SEQ ID NO 1
<211> LENGTH: 6271
<212> TYPE: DNA
<213> ORGANISM: Artificial Sequence
<220> FEATURE:
<223> OTHER INFORMATION: pSEC84 Expression Plasmid

<400> SEQUENCE: 1

```
gaattctgtg gtagcacaga ataatgaaaa gtgtgtaaag aagggtaaaa aaaaccgaat        60
gcgaggcatc cggttgaaat aggggtaaac agacattcag aaatgaatga cggtaataaa       120
taaagttaat gatgatagcg ggagttattc tagttgcgag tgaaggtttt gttttgacat       180
tcagtgctgt caaatactta agaataagtt attgatttta accttgaatt attattgctt       240
gatgttaggt gcttatttcg ccattccgca ataatcttaa aaagttccct tgcatttaca       300
ttttgaaaca tctatagcga taaatgaaac atcttaaaag ttttagtatc atattcgtgt       360
tggattattc tgcatttttg gggagaatgg acttgccgac tgattaatga gggttaatca       420
gtatgcagtg gcataaaaaa gcaaataaag gcatataaca gatcgatctt aaacatccac       480
aggaggatgg gatccaaaat aaggaggaaa aaaaaatgac tagtatttttt gcagaacaaa       540 ctgtagaggt agttaaaagc gcgatcgaaa ccgcagatgg ggcattagat ctttataaca       600
aatacctcga ccaggtcatc ccctggaaga cctttgatga aaccataaaa gagttaagcc       660
gttttaaaca ggagtactcg caggaagctt ctgttttagt tggtgatatt aaagttttgc       720
ttatggacag ccaggacaag tattttgaag cgacacaaac tgtttatgaa tggtgtggtg       780
tcgtgacgca attactctca gcgtatattt tactatttga tgaatataat gagaaaaaag       840
catcagccca gaaagacatt ctcattagga tattagatga tggtgtcaag aaactgaatg       900
aagcgcaaaa atctctcctg acaagttcac aaagtttcaa caacgcttcc ggaaaactgc       960
tggcattaga tagccagtta actaatgatt tttcggaaaa aagtagttat ttccagtcac      1020
aggtggatag aattcgtaag gaagcttatg ccggtgctgc agccggcata gtcgccggtc      1080
cgtttggatt aattatttcc tattctattg ctgcgggcgt gattgaaggg aaattgattc      1140
cagaattgaa taacaggcta aaaacagtgc aaaatttctt tactagctta tcagctacag      1200
tgaaacaagc gaataaagat atcgatgcgg caaaattgaa attagccact gaaatagcag      1260
caattgggga gataaaaacg gaaaccgaaa caaccagatt ctacgttgat tatgatgatt      1320
taatgctttc tttattaaaa ggagctgcaa agaaaatgat taacacctgt aatgaatacc      1380
aacaacgtca tggtaagaag acgcttttcg aggttcctga cgtcgctagc tgataaccta      1440
gggccagcaa aaggccagga accgtaaaaa ggccgcgttg ctggcgtttt tccataggct      1500
```

```
ccgccccccct gacgagcatc acaaaaatcg acgctcaagt cagaggtggc gaaacccgac    1560
aggactataa agataccagg cgtttccccc tggaagctcc ctcgtgcgct ctcctgttcc    1620
gaccctgccg cttaccggat acctgtccgc ctttctccct tcgggaagcg tggcgctttc    1680
tcatagctca cgctgtaggt atctcagttc ggtgtaggtc gttcgctcca agctgggctg    1740
tgtgcacgaa ccccccgttc agcccgaccg ctgcgcctta ccggtaact atcgtcttga    1800 gtccaacccg gtaagacacg acttatcgcc actggcagca gccactggta acaggattag    1860
cagagcgagg tatgtaggcg gtgctacaga gttcttgaag tggtggccta actacggcta    1920
cactagaagg acagtatttg gtatctgcgc tctgctgaag ccagttacct tcggaaaaag    1980
agttggtagc tcttgatccg gcaaacaaac caccgctggt agcggtggtt tttttgtttg    2040
caagcagcag attacgcgca gaaaaaaagg atctcaagaa gatcctttga tcttttctac    2100
ggggtctgac gctcagtaga tctaaaacac taggcccaag agtttgtaga aacgcaaaaa    2160
ggccatccgt caggatggcc ttctgcttaa tttgatgcct ggcagtttat ggcgggcgtc    2220
ctgcccgcca cctccgggc cgttgcttcg caacgttcaa atccgctccc ggcggatttg    2280
tcctactcag gagagcgttc accgacaaac aacagataaa acgaaaggcc cagtctttcg    2340
actgagcctt tcgttttatt tgatgcctgg cagttcccta ctctcgcatg gggagacccc    2400
acactaccat cggcgctacg gcgtttcact tctgagttcg gcatgggggtc aggtgggacc    2460 accgcgctac tgccgccagg caaattcgt tttatcagac cgcttctgcg ttctgattta    2520
atctgtatca ggctgaaaat cttctctcat ccgccaaaac agccaagctg atctggcaa    2580 atcgctgaat attccttttg tctccgacca tcaggcacct gagtcgctgt cttttttcgtg    2640 acattcagtt cgctgcgctc acggctctgg cagtgaatgg gggtaaatgg cactacaggc    2700
gccttttatg gattcatgca aggaaactac ccataataca agaaaagccc gtcacgggct    2760
tctcagggcg ttttatggcg ggtctgctat gtggtgctat ctgactttt gctgttcagc    2820 agttcctgcc ctctgatttt ccagtctgac cacttcggat tatcccgtga caggtcattc    2880
agactggcta atgcacccag taaggcagcg gtatcatcaa caggcttacc cgtcttactg    2940
tcaaccggat ctaaaacact agcccaacct ttcatagaag gcggcggtgg aatcgaaatc    3000
tcgtgatggc aggttgggcg tcgcttggtc ggtcatttcg aaccccagag tcccgctcag    3060
aagaactcgt caagaaggcg atagaaggcg atgcgctgcg aatcgggagc ggcgataccg    3120
taaagcacga ggaagcggtc agcccattcg ccgccaagct cttcagcaat atcacgggta    3180
gccaacgcta tgtcctgata gcggtccgcc acacccagcc ggccacagtc gatgaatcca    3240
gaaaagcggc catttccac catgatattc ggcaagcagg catcgccatg ggtcacgacg    3300
agatcctcgc cgtcgggcat gcgcgccttg agcctggcga acagttcggc tggcgcgagc    3360
ccctgatgct cttcgtccag atcatcctga tcgacaagac cggcttccat ccgagtacgt    3420
gctcgctcga tgcgatgttt cgcttggtgg tcgaatgggc aggtagccgg atcaagcgta    3480
tgcagccgcc gcattgcatc agccatgatg gatactttct cggcaggagc aaggtgagat    3540
gacaggagat cctgccccgg cacttcgccc aatagcagcc agtcccttcc cgcttcagtg    3600
acaacgtcga gcacagctgc gcaaggaacg cccgtcgtgg ccagccacga tagccgcgct    3660
gcctcgtcct gcagttcatt cagggcaccg gacaggtcgg tcttgacaaa aagaaccggg    3720
cgcccctgcg ctgacagccg gaacacggcg gcatcagagc agccgattgt ctgttgtgcc    3780
cagtcatagc cgaatagcct ctccacccaa gcggccggag aacctgcgtg caatccatct    3840
tgttcaatca tgcgaaacga tcctcatcct gtctcttgat cagatcttga tccctgcgc    3900
```

```
catcagatcc ttggcggcaa gaaagccatc cagtttactt tgcagggctt cccaacctta    3960
ccagagggcg ccccagctgg caattccggt tcgctgctag acaacatcag caaggagaaa    4020
ggggctaccg gcgaaccagc agccccttta taaaggcgct tcagtagtca gaccagcatc    4080
agtcctgaaa aggcgggcct gcgcccgcct ccaggttgct acttaccgga ttcgtaagcc    4140
atgaaagccg ccacctccct gtgtccgtct ctgtaacgaa tctcgcacag cgattttcgt    4200
gtcagataag tgaatatcaa cagtgtgaga cacacgatca acacacacca gacaagggaa    4260
cttcgtggta gtttcatggc cttcttctcc ttgcgcaaag cgcggtaaga ggctatcctg    4320
atgtggacta gacatagga tgcctcgtgg tggttaatga aaattaactt actacggggc    4380
tatcttcttt ctgccacaca acacggcaac aaaccacctt cacgtcatga ggcagaaagc    4440
ctcaagcgcc gggcacatca tagcccatat acctgcacgc tgaccacact cactttccct    4500
gaaaataatc cgctcattca gaccgttcac gggaaatccg tgtgattgtt gccgcatcac    4560
gctgcctccc ggagtttgtc tcgagcactt ttgttacccg ccaaacaaaa cccaaaaaca    4620
acccataccc aacccaataa acaccaaaa caagacaaat aatcattgat tgatggttga    4680
aatggggtaa acttgacaaa caaacccact taaaacccaa aacatacca aacacacacc    4740
aaaaaaacac cataaggagt tttataaatg ttggtattca ttgatgacgg ttcaacaaac    4800
atcaaactac agtggcagga aagcgacgga acaattaaac agcacattag cccgaacagc    4860
ttcaaacgcg agtgggcagt ctcttttggt gataaaaagg tctttaacta cacactgaac    4920
ggcgaacagt attcatttga tccaatcagc ccggatgctg tagtcacaac caatatcgca    4980
tggcaataca gcgacgttaa tgtcgttgca gtgcatcacg ccttactgac cagtggtctg    5040
ccggtaagcg aagtggatat tgtttgcaca cttcctctga cagagtatta cgacagaaat    5100
aaccaaccca atacggaaaa tattgagcgt aagaaagcaa acttccggaa aaaaattaca    5160
ttaaatggcg gggatacatt cacaataaaa gatgtaaaag tcatgcctga atctataccg    5220
gcaggttatg aagttctaca agaactggat gagttagatt ctttattaat tatagatctc    5280
gggggcacca cattagatat ttctcaggta atggggaaat tatcggggat cagtaaaata    5340
tacggagact catctcttgg tgtctctctg gttacatctg cagtaaaaga tgcccttct    5400
cttgcgagaa caaaggaag tagctatctt gctgacgata taatcattca cagaaaagat    5460
aataactatc tgaagcaacg aattaatgat gagaacaaaa tatcaatagt caccgaagca    5520
atgaatgaag cacttcgtaa acttgagcaa cgtgtattaa atacgctcaa tgaattttct    5580
ggttatactc atgttatggt tataggcggt ggcgcagaat taatatgcga tgcagtaaaa    5640
aaacacacac agattcgtga tgaacgtttt ttcaaaacca ataactctca atatgattta    5700
gttaacggta tgtatctcat aggtaattaa tgatggacaa gcgcagaacc attgccttca    5760
aactaaatcc agatgtaaat caaacagata aaattgtttg tgatacactg gacagtatcc    5820
cgcaaggga acgaagccgc cttaaccggg ccgcactgac ggcaggtctg gccttataca    5880
gacaagatcc ccggaccct ttcctttat gtgagctgct gacgaaagaa accacatttt    5940
cagatatcgt gaatatattg agatcgctat ttccaaaaga gatggccgat tttaattctt    6000
caatagtcac tcaatcctct tcacaacaag agcaaaaaag tgatgaagag accaaaaaaa    6060
atgcgatgaa gctaataaat taattcaatt attattgagt tccctttatc cactatcagg    6120
ctggataaag ggaactcaat caagttattt tcttaccagt cattacataa tcgttattat    6180
gaaataatcg tttgcactgt ctctgttatt caggcaattt caataaaggc acttgctcac    6240
```

```
gctctgtcat tttctgaaac tcttcatgct g                               6271
```

<210> SEQ ID NO 2
<211> LENGTH: 305
<212> TYPE: PRT
<213> ORGANISM: Salmonella typhi

<400> SEQUENCE: 2

```
Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
        195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser
305
```

<210> SEQ ID NO 3
<211> LENGTH: 102
<212> TYPE: DNA
<213> ORGANISM: Artificial Sequence
<220> FEATURE:
<223> OTHER INFORMATION: Cloning Primer

<400> SEQUENCE: 3

```
ggatccaaaa taaggaggaa aaaaaaatga ctagtatttt tgcagaacaa actgtagagg      60
tagttaaaag cgcgatcgaa accgcagatg gggcattaga tc                       102

<210> SEQ ID NO 4
<211> LENGTH: 101
<212> TYPE: DNA
<213> ORGANISM: Artificial Sequence
<220> FEATURE:
<223> OTHER INFORMATION: Cloning Primer

<400> SEQUENCE: 4
cctaggttat cagctagcga cgtcaggaac ctcgaaaagc gtcttcttac catgacgttg      60
ttggtattca ttacaggtgt taatcatttt ctttgcagct c                        101

<210> SEQ ID NO 5
<211> LENGTH: 97
<212> TYPE: DNA
<213> ORGANISM: Artificial Sequence
<220> FEATURE:
<223> OTHER INFORMATION: Cloning Primer

<400> SEQUENCE: 5
cacggtaaga agacgctttt cgaggttcct gacgtcgcta gctgataacc taggtcatgt      60
tagacagctt atcatcgata agctttaatg cggtagt                              97

<210> SEQ ID NO 6
<211> LENGTH: 69
<212> TYPE: DNA
<213> ORGANISM: Artificial Sequence
<220> FEATURE:
<223> OTHER INFORMATION: Cloning Primer

<400> SEQUENCE: 6
agatctacta gtgtcgacgc tagctatcag gtcgaggtgg cccggctcca tgcaccgcga      60
cgcaacgcg                                                             69

<210> SEQ ID NO 7
<211> LENGTH: 60
<212> TYPE: DNA
<213> ORGANISM: Artificial Sequence
<220> FEATURE:
<223> OTHER INFORMATION: Cloning Primer

<400> SEQUENCE: 7
actagtcacc cagaaacgct ggtgaaagta aagatgctg aagatcagtt gggtgcacga      60

<210> SEQ ID NO 8
<211> LENGTH: 101
<212> TYPE: DNA
<213> ORGANISM: Artificial Sequence
<220> FEATURE:
<223> OTHER INFORMATION: Cloning Primer

<400> SEQUENCE: 8
cattaaaggt tatcgatgat aagctgtcaa acatgagcta gcctaggtca ttaccaatgc      60
ttaatcagtg aggcacctat ctcagcgatc tgtctatttc g                        101

<210> SEQ ID NO 9
<211> LENGTH: 101
<212> TYPE: DNA
<213> ORGANISM: Artificial Sequence
<220> FEATURE:
```

<223> OTHER INFORMATION: Cloning Primer

<400> SEQUENCE: 9

```
cgaaatagac agatcgctga gataggtgcc tcactgatta agcattggta atgacctagg      60
ctagctcatg tttgacagct tatcatcgat aacctttaat g                        101
```

<210> SEQ ID NO 10
<211> LENGTH: 71
<212> TYPE: DNA
<213> ORGANISM: Artificial Sequence
<220> FEATURE:
<223> OTHER INFORMATION: Cloning Primer

<400> SEQUENCE: 10

```
gcgcactagt aaagaaacga accaaaagcc atataaggaa acatacggca tttcccatat      60
tacacgccat g                                                          71
```

<210> SEQ ID NO 11
<211> LENGTH: 103
<212> TYPE: DNA
<213> ORGANISM: Artificial Sequence
<220> FEATURE:
<223> OTHER INFORMATION: Cloning Primer

<400> SEQUENCE: 11

```
taaactaccg cattaaagct tatcgatgat aagctgtcaa acatgacccg ggtcactatt      60
tgttaactgt taattgtcct tgttcaagga tgctgtcttt gac                      103
```

<210> SEQ ID NO 12
<211> LENGTH: 46
<212> TYPE: DNA
<213> ORGANISM: Artificial Sequence
<220> FEATURE:
<223> OTHER INFORMATION: Cloning Primer

<400> SEQUENCE: 12

```
tcatgtttga cagcttatca tcgataagct taatgcggt agttta                     46
```

<210> SEQ ID NO 13
<211> LENGTH: 80
<212> TYPE: DNA
<213> ORGANISM: Artificial Sequence
<220> FEATURE:
<223> OTHER INFORMATION: Cloning Primer

<400> SEQUENCE: 13

```
gcgcagatct taatcatcca caggaggcgc tagcatgagt aaaggagaag aactttttcac     60
tggagttgtc ccaattcttg                                                 80
```

<210> SEQ ID NO 14
<211> LENGTH: 110
<212> TYPE: DNA
<213> ORGANISM: Artificial Sequence
<220> FEATURE:
<223> OTHER INFORMATION: Cloning Primer

<400> SEQUENCE: 14

```
gtgataaact accgcattaa agcttatcga tgataagctg tcaaacatga gcgctctaga      60
actagttcat tatttgtaga gctcatccat gccatgtgta atcccagcag                110
```

<210> SEQ ID NO 15
<211> LENGTH: 94

<212> TYPE: DNA
<213> ORGANISM: Artificial Sequence
<220> FEATURE:
<223> OTHER INFORMATION: Cloning Primer

<400> SEQUENCE: 15

```
gcgcactagt aaaaaccttg attgttgggt cgacaacgaa gaagacatcg atgttatcct    60
gaaaaagtct accattctga acttggacat caac                                94
```

<210> SEQ ID NO 16
<211> LENGTH: 97
<212> TYPE: DNA
<213> ORGANISM: Artificial Sequence
<220> FEATURE:
<223> OTHER INFORMATION: Cloning Primer

<400> SEQUENCE: 16

```
aactaccgca ttaaagctta tcgatgataa gctgtcaaac atgagctagc ctaggtcatt    60
agtcgttggt ccaaccttca tcggtcggaa cgaagta                              97
```

<210> SEQ ID NO 17
<211> LENGTH: 30
<212> TYPE: DNA
<213> ORGANISM: Artificial Sequence
<220> FEATURE:
<223> OTHER INFORMATION: Cloning Primer

<400> SEQUENCE: 17

```
cgatgcggca aaattgaaat tagccactga                                      30
```

<210> SEQ ID NO 18
<211> LENGTH: 8908
<212> TYPE: DNA
<213> ORGANISM: Artificial Sequence
<220> FEATURE:
<223> OTHER INFORMATION: pSEC84sacB vector

<400> SEQUENCE: 18

```
gaattctgtg gtagcacaga ataatgaaaa gtgtgtaaag aagggtaaaa aaaaccgaat     60
gcgaggcatc cggttgaaat aggggtaaac agacattcag aaatgaatga cgtaataaa    120 taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcatttttg gggagaatgg acttgccgac tgattaatga gggttaatca    420
gtatgcagtg gcataaaaaa gcaaataaag gcatataaca gatcgatctt aaacatccac    480
aggaggatgg gatccaaaat aaggaggaaa aaaaatgac tagtatttt gcagaacaaa    540 ctgtagaggt agttaaaagc gcgatcgaaa ccgcagatgg gcattagat ctttataaca    600 aatacctcga ccaggtcatc ccctggaaga cctttgatga accataaaa gagttaagcc    660 gttttaaaca ggagtactcg caggaagctt ctgttttagt tggtgatatt aaagttttgc    720
ttatggacag ccaggacaag tattttgaag cgacacaaac tgtttatgaa tggtgtggtg    780
tcgtgacgca attactctca gcgtatattt tactatttga tgaatataat gagaaaaaag    840
catcagccca gaaagacatt ctcattagga tattagatga tggtgtcaag aaactgaatg    900
aagcgcaaaa atctctcctg acaagttcac aaagtttcaa caacgcttcc ggaaaactgc    960
```

```
tggcattaga tagccagtta actaatgatt tttcggaaaa aagtagttat ttccagtcac    1020
aggtggatag aattcgtaag gaagcttatg ccggtgctgc agccggcata gtcgccggtc    1080
cgtttggatt aattatttcc tattctattg ctgcgggcgt gattgaaggg aaattgattc    1140
cagaattgaa taacaggcta aaaacagtgc aaaatttctt tactagctta tcagctacag    1200
tgaaacaagc gaataaagat atcgatgcgg caaaattgaa attagccact gaaatagcag    1260
caattgggga gataaaaacg gaaaccgaaa caaccagatt ctacgttgat tatgatgatt    1320
taatgctttc tttattaaaa ggagctgcaa agaaaatgat taacacctgt aatgaatacc    1380
aacaacgtca tggtaagaag acgcttttcg aggttcctga cgtcgctagt aaagaaacga    1440
accaaaagcc atataaggaa acatacggca tttcccatat tacacgccat gatatgctgc    1500
aaatccctga acagcaaaaa aatgaaaaat atcaagttcc tgaattcgat tcgtccacaa    1560
ttaaaaatat ctcttctgca aaaggcctgg acgtttggga cagctggcca ttacaaaacg    1620 ctgacgcac tgtcgcaaac tatcacggct accacatcgt ctttgcatta gccggagatc    1680
ctaaaaatgc ggatgacaca tcgatttaca tgttctatca aaaagtcggc gaaacttcta    1740 ttgcagctg gaaaaacgct ggccgcgtct ttaaagacag cgacaaattc gatgcaaatg    1800
attctatcct aaaagaccaa acacaagaat ggtcaggttc agccacattt acatctgacg    1860
gaaaaatccg tttattctac actgatttct ccggtaaaca ttacggcaaa caaacactga    1920
caactgcaca agttaacgta tcagcatcag acagctcttt gaacatcaac ggtgtagagg    1980
attataaatc aatctttgac ggtgacggaa aaacgtatca aaatgtacag cagttcatcg    2040
atgaaggcaa ctacagctca ggcgacaacc atacgctgag agatcctcac tacgtagaag    2100
ataaaggcca caaatactta gtatttgaag caaacactgg aactgaagat ggctaccaag    2160
gcgaagaatc tttatttaac aaagcatact atggcaaaag cacatcattc ttccgtcaag    2220
aaagtcaaaa acttctgcaa agcgataaaa aacgcacggc tgagttagca acggcgctc    2280 tcggtatgat tgagctaaac gatgattaca cactgaaaaa agtgatgaaa ccgctgattg    2340
catctaacac agtaacagat gaaattgaac gcgcgaacgt cttttaaaatg aacggcaaat    2400 ggtacctgtt cactgactcc cgcggatcaa aaatgacgat tgacggcatt acgtctaacg    2460
atatttacat gcttggttat gtttctaatt ctttaactgg cccatacaag ccgctgaaca    2520
aaactggcct tgtgttaaaa atggatcttg atcctaacga tgtaacctt acttactcac    2580 acttcgctgt acctcaagcg aaaggaaaca atgtcgtgat tacaagctat atgacaaaca    2640
gaggattcta cgcagacaaa caatcaacgt ttgcgccaag cttcctgctg aacatcaaag    2700
gcaagaaaac atctgttgtc aaagacagca tccttgaaca aggacaatta acagttaaca    2760
aatagtgacc cgggtcatgt ttgacagctt atcatcgata agctttaatg cggtagttta    2820
tcacagttaa attgctaacg cagtcaggca ccgtgtatga aatctaacaa tgcgctcatc    2880
gtcatcctcg gcaccgtcac cctggatgct gtaggcatag gcttggttat gccggtactg    2940
ccgggcctct tgcgggatat cgtccattcc gacagcatcg ccagtcacta tggcgtgctg    3000
ctagcgctat atgcgttgat gcaatttcta tgcgcacccg ttctcggagc actgtccgac    3060
cgctttggcc gccgcccagt cctgctcgct tcgctacttg gagccactat cgactacgcg    3120
atcatggcga ccacacccgt cctgtggatc ctctacgccg gacgcatcgt ggccggcatc    3180
accggcgcca caggtgcggt tgctggcgcc tatatcgccg acatcaccga tggggaagat    3240
cgggctcgcc acttcgggct catgagcgct tgtttcggcg tgggtatggt ggcaggcccc    3300
gtggccgggg gactgttggg cgccatctcc ttgcatgcac cattccttgc ggcggcggtg    3360
```

```
ctcaacggcc tcaacctact actgggctgc ttcctaatgc aggagtcgca taagggagag   3420
cgtcgaccga tgcccttgag agccttcaac ccagtcagct ccttccggtg ggcgcggggc   3480
atgactatcg tcgccgcact tatgactgtc ttctttatca tgcaactcgt aggacaggtg   3540
ccggcagcgc tctgggtcat tttcggcgag accgctttc gctggagcgc gacgatgatc    3600
ggcctgtcgc ttgcggtatt cggaatcttg cacgccctcg ctcaagcctt cgtcactggt   3660
cccgccacca aacgtttcgg cgagaagcag gccattatcg ccggcatggc ggccgacgcg   3720
ctgggctacg tcttgctggc gttcgcgacg cgaggctgga tggccttccc cattatgatt   3780
cttctcgctt ccggcggcat cgggatgccc gcgttgcagg ccatgctgtc caggcaggta   3840
gatgacgacc atcagggaca gcttcaagga tcgctcgcgg ctcttaccag cctaacttcg   3900
atcactggac cgctgatcgt cacggcgatt tatgccgcct cggcgagcac atggaacggg   3960
ttggcatgga ttgtaggcgc cgccctatac cttgtctgcc tccccgcgtt cgtcgcggt    4020 gcatggagcc gggccacctc gacctgatag ctagcgtcga cactagctga taacctaggg   4080
ccagcaaaag gccaggaacc gtaaaaaggc cgcgttgctg gcgttttttcc ataggctccg   4140 cccccctgac gagcatcaca aaaatcgacg ctcaagtcag aggtggcgaa acccgacagg   4200
actataaaga taccaggcgt ttccccctgg aagctccctc gtgcgctctc ctgttccgac   4260
cctgccgctt accggatacc tgtccgcctt tctcccttcg ggaagcgtgg cgctttctca   4320
tagctcacgc tgtaggtatc tcagttcggt gtaggtcgtt cgctccaagc tgggctgtgt   4380
gcacgaaccc cccgttcagc ccgaccgctg cgccttatcc ggtaactatc gtcttgagtc   4440
caacccggta agacacgact tatcgccact ggcagcagcc actggtaaca ggattagcag   4500
agcgaggtat gtaggcggtg ctacagagtt cttgaagtgg tggcctaact acggctacac   4560
tagaaggaca gtatttggta tctgcgctct gctgaagcca gttaccttcg gaaaaagagt   4620
tggtagctct tgatccggca aacaaaccac cgctggtagc ggtggttttt tgtttgcaa    4680 gcagcagatt acgcgcagaa aaaaaggatc tcaagaagat cctttgatct tttctacggg   4740
gtctgacgct cagtagatct aaaacactag gcccaagagt ttgtagaaac gcaaaaaggc   4800
catccgtcag gatggccttc tgcttaattt gatgcctggc agtttatggc gggcgtcctg   4860
cccgccaccc tccgggccgt tgcttcgcaa cgttcaaatc cgctcccggc ggatttgtcc   4920
tactcaggag agcgttcacc gacaaacaac agataaaacg aaaggcccag tctttcgact   4980
gagcctttcg ttttatttga tgcctggcag ttccctactc tcgcatgggg agaccccaca   5040
ctaccatcgg cgctacggcg tttcacttct gagttcggca tggggtcagg tgggaccacc   5100
gcgctactgc cgccaggcaa attctgtttt atcagaccgc ttctgcgttc tgatttaatc   5160
tgtatcaggc tgaaaatctt ctctcatccg ccaaaacagc caagctggat ctggcaaatc   5220
gctgaatatt cctttttgtct ccgaccatca ggcacctgag tcgctgtctt tttcgtgaca   5280
ttcagttcgc tgcgctcacg gctctggcag tgaatggggg taaatggcac tacaggcgcc   5340
ttttatggat tcatgcaagg aaactaccca taatacaaga aaagcccgtc acgggcttct   5400
cagggcgttt tatggcgggt ctgctatgtg gtgctatctg acttttttgct gttcagcagt   5460 tcctgccctc tgattttcca gtctgaccac ttcggattat cccgtgacag gtcattcaga   5520
ctggctaatg cacccagtaa ggcagcggta tcatcaacag gcttacccgt cttactgtca   5580
accggatcta aaacactagc ccaacctttc atagaaggcg cggtggaat cgaaatctcg    5640 tgatggcagg ttgggcgtcg cttggtcggt catttcgaac cccagagtcc cgctcagaag   5700
```

```
aactcgtcaa gaaggcgata gaaggcgatg cgctgcgaat cgggagcggc gataccgtaa    5760
agcacgagga agcggtcagc ccattcgccg ccaagctctt cagcaatatc acgggtagcc    5820
aacgctatgt cctgatagcg gtccgccaca cccagccggc cacagtcgat gaatccagaa    5880
aagcggccat tttccaccat gatattcggc aagcaggcat cgccatgggt cacgacgaga    5940
tcctcgccgt cgggcatgcg cgccttgagc ctggcgaaca gttcggctgg cgcgagcccc    6000
tgatgctctt cgtccagatc atcctgatcg acaagaccgg cttccatccg agtacgtgct    6060
cgctcgatgc gatgtttcgc ttggtggtcg aatgggcagg tagccggatc aagcgtatgc    6120
agccgccgca ttgcatcagc catgatggat actttctcgg caggagcaag gtgagatgac    6180
aggagatcct gccccggcac ttcgcccaat agcagccagt cccttcccgc ttcagtgaca    6240
acgtcgagca cagctgcgca aggaacgccc gtcgtggcca gccacgatag ccgcgctgcc    6300
tcgtcctgca gttcattcag ggcaccggac aggtcggtct tgacaaaaag aaccgggcgc    6360
ccctgcgctg acagccggaa cacgcggca tcagagcagc cgattgtctg ttgtgcccag    6420
tcatagccga atagcctctc cacccaagcg gccggagaac ctgcgtgcaa tccatcttgt    6480
tcaatcatgc gaaacgatcc tcatcctgtc tcttgatcag atcttgatcc cctgcgccat    6540
cagatccttg gcggcaagaa agccatccag tttactttgc agggcttccc aaccttacca    6600
gagggcgccc cagctggcaa ttccggttcg ctgctagaca acatcagcaa ggagaaaggg    6660
gctaccggcg aaccagcagc ccctttataa aggcgcttca gtagtcagac cagcatcagt    6720
cctgaaaagg cgggcctgcg cccgcctcca ggttgctact taccggattc gtaagccatg    6780
aaagccgcca cctcccctgtg tccgtctctg taacgaatct cgcacagcga ttttcgtgtc    6840
agataagtga atatcaacag tgtgagacac acgatcaaca cacaccagac aagggaactt    6900
cgtggtagtt tcatggcctt cttctccttg cgcaaagcgc ggtaagaggc tatcctgatg    6960
tggactagac atagggatgc ctcgtggtgg ttaatgaaaa ttaacttact acggggctat    7020
cttctttctg ccacacaaca cggcaacaaa ccaccttcac gtcatgaggc agaaagcctc    7080
aagcgccggg cacatcatag cccatatacc tgcacgctga ccacactcac tttccctgaa    7140
aataatccgc tcattcagac cgttcacggg aaatccgtgt gattgttgcc gcatcacgct    7200
gcctcccgga gtttgtctcg agcacttttg ttacccgcca aacaaaaccc aaaaacaacc    7260
catacccaac ccaataaaac accaaaacaa gacaaataat cattgattga tggttgaaat    7320
ggggtaaact tgacaaacaa acccacttaa aacccaaaac ataccccaaac acacaccaaa    7380
aaaacaccat aaggagtttt ataaatgttg gtattcattg atgacggttc aacaaacatc    7440
aaactacagt ggcaggaaag cgacggaaca attaaacagc acattagccc gaacagcttc    7500
aaacgcgagt gggcagtctc ttttggtgat aaaaaggtct ttaactacac actgaacggc    7560
gaacagtatt catttgatcc aatcagcccg gatgctgtag tcacaaccaa tatcgcatgg    7620
caatacagcg acgttaatgt cgttgcagtg catcacgcct tactgaccag tggtctgccg    7680
gtaagcgaag tggatattgt ttgcacactt cctctgacag agtattacga cagaaataac    7740
caacccaata cggaaaatat tgagcgtaag aaagcaaact tccggaaaaa aattacatta    7800
aatggcgggg atacattcac aataaaagat gtaaagtcat gcctgaatc tataccggca    7860
ggttatgaag ttctacaaga actggatgag ttagattctt tattaattat agatctcggg    7920
ggcaccacat tagatatttc tcaggtaatg gggaaattat cggggatcag taaaatatac    7980
ggagactcat ctcttggtgt ctctctggtt acatctgcag taaaagatgc cctttctctt    8040
gcgagaacaa aaggaagtag ctatcttgct gacgatataa tcattcacag aaaagataat    8100
```

-continued

```
aactatctga agcaacgaat taatgatgag aacaaaatat caatagtcac cgaagcaatg    8160
aatgaagcac ttcgtaaact tgagcaacgt gtattaaata cgctcaatga atttctggt    8220 tatactcatg ttatggttat aggcggtggc gcagaattaa tatgcgatgc agtaaaaaaa    8280
cacacacaga ttcgtgatga acgttttttc aaaaccaata actctcaata tgatttagtt    8340
aacggtatgt atctcatagg taattaatga tggacaagcg cagaaccatt gccttcaaac    8400
taaatccaga tgtaaatcaa acagataaaa ttgtttgtga tacactggac agtatcccgc    8460
aaggggaacg aagccgcctt aaccgggccg cactgacggc aggtctggcc ttatacagac    8520
aagatcgccg gacccctttc cttttatgtg agctgctgac gaaagaaacc acattttcag    8580
atatcgtgaa tatattgaga tcgctatttc caaagagat ggccgatttt aattcttcaa    8640
tagtcactca atcctcttca caacaagagc aaaaaagtga tgaagagacc aaaaaaaatg    8700
cgatgaagct aataaattaa ttcaattatt attgagttcc ctttatccac tatcaggctg    8760
gataaaggga actcaatcaa gttatttttct taccagtcat tacataatcg ttattatgaa    8820
ataatcgttt gcactgtctc tgttattcag gcaatttcaa taaaggcact tgctcacgct    8880
ctgtcatttt ctgaaactct tcatgctg                                       8908
```

<210> SEQ ID NO 19
<211> LENGTH: 2253
<212> TYPE: DNA
<213> ORGANISM: Artificial Sequence
<220> FEATURE:
<223> OTHER INFORMATION: ClyA::SacB fusion gene
<220> FEATURE:
<221> NAME/KEY: CDS
<222> LOCATION: (1)..(2253)

<400> SEQUENCE: 19

```
atg act agt att ttt gca gaa caa act gta gag gta gtt aaa agc gcg      48
Met Thr Ser Ile Phe Ala Glu Gln Thr Val Glu Val Val Lys Ser Ala
1               5                  10                  15 atc gaa acc gca gat ggg gca tta gat ctt tat aac aaa tac ctc gac      96
Ile Glu Thr Ala Asp Gly Ala Leu Asp Leu Tyr Asn Lys Tyr Leu Asp
            20                  25                  30 cag gtc atc ccc tgg aag acc ttt gat gaa acc ata aaa gag tta agc     144
Gln Val Ile Pro Trp Lys Thr Phe Asp Glu Thr Ile Lys Glu Leu Ser
        35                  40                  45 cgt ttt aaa cag gag tac tcg cag gaa gct tct gtt tta gtt ggt gat     192
Arg Phe Lys Gln Glu Tyr Ser Gln Glu Ala Ser Val Leu Val Gly Asp
    50                  55                  60 att aaa gtt ttg ctt atg gac agc cag gac aag tat ttt gaa gcg aca     240
Ile Lys Val Leu Leu Met Asp Ser Gln Asp Lys Tyr Phe Glu Ala Thr
65                  70                  75                  80 caa act gtt tat gaa tgg tgt ggt gtc gtg acg caa tta ctc tca gcg     288
Gln Thr Val Tyr Glu Trp Cys Gly Val Val Thr Gln Leu Leu Ser Ala
                85                  90                  95 tat att tta cta ttt gat gaa tat aat gag aaa aaa gca tca gcc cag     336
Tyr Ile Leu Leu Phe Asp Glu Tyr Asn Glu Lys Lys Ala Ser Ala Gln
            100                 105                 110 aaa gac att ctc att agg ata tta gat gat ggt gtc aag aaa ctg aat     384
Lys Asp Ile Leu Ile Arg Ile Leu Asp Asp Gly Val Lys Lys Leu Asn
        115                 120                 125 gaa gcg caa aaa tct ctc ctg aca agt tca caa agt ttc aac aac gct     432
Glu Ala Gln Lys Ser Leu Leu Thr Ser Ser Gln Ser Phe Asn Asn Ala
    130                 135                 140 tcc gga aaa ctg ctg gca tta gat agc cag tta act aat gat ttt tcg     480
Ser Gly Lys Leu Leu Ala Leu Asp Ser Gln Leu Thr Asn Asp Phe Ser
```

```
                Ser Gly Lys Leu Leu Ala Leu Asp Ser Gln Leu Thr Asn Asp Phe Ser
                145                 150                 155                 160 gaa aaa agt agt tat ttc cag tca cag gtg gat aga att cgt aag gaa           528
Glu Lys Ser Ser Tyr Phe Gln Ser Gln Val Asp Arg Ile Arg Lys Glu
                165                 170                 175 gct tat gcc ggt gct gca gcc ggc ata gtc gcc ggt ccg ttt gga tta           576
Ala Tyr Ala Gly Ala Ala Ala Gly Ile Val Ala Gly Pro Phe Gly Leu
                180                 185                 190 att att tcc tat tct att gct gcg ggc gtg att gaa ggg aaa ttg att           624
Ile Ile Ser Tyr Ser Ile Ala Ala Gly Val Ile Glu Gly Lys Leu Ile
                195                 200                 205 cca gaa ttg aat aac agg cta aaa aca gtg caa aat ttc ttt act agc           672
Pro Glu Leu Asn Asn Arg Leu Lys Thr Val Gln Asn Phe Phe Thr Ser
        210                 215                 220 tta tca gct aca gtg aaa caa gcg aat aaa gat atc gat gcg gca aaa           720
Leu Ser Ala Thr Val Lys Gln Ala Asn Lys Asp Ile Asp Ala Ala Lys
225                 230                 235                 240 ttg aaa tta gcc act gaa ata gca gca att ggg gag ata aaa acg gaa           768
Leu Lys Leu Ala Thr Glu Ile Ala Ala Ile Gly Glu Ile Lys Thr Glu
                245                 250                 255 acc gaa aca acc aga ttc tac gtt gat tat gat gat tta atg ctt tct           816
Thr Glu Thr Thr Arg Phe Tyr Val Asp Tyr Asp Asp Leu Met Leu Ser
                260                 265                 270 tta tta aaa gga gct gca aag aaa atg att aac acc tgt aat gaa tac           864
Leu Leu Lys Gly Ala Ala Lys Lys Met Ile Asn Thr Cys Asn Glu Tyr
        275                 280                 285 caa caa cgt cat ggt aag aag acg ctt ttc gag gtt cct gac gtc gct           912
Gln Gln Arg His Gly Lys Lys Thr Leu Phe Glu Val Pro Asp Val Ala
        290                 295                 300 agt aaa gaa acg aac caa aag cca tat aag gaa aca tac ggc att tcc           960
Ser Lys Glu Thr Asn Gln Lys Pro Tyr Lys Glu Thr Tyr Gly Ile Ser
305                 310                 315                 320 cat att aca cgc cat gat atg ctg caa atc cct gaa cag caa aaa aat          1008
His Ile Thr Arg His Asp Met Leu Gln Ile Pro Glu Gln Gln Lys Asn
                325                 330                 335 gaa aaa tat caa gtt cct gaa ttc gat tcg tcc aca att aaa aat atc          1056
Glu Lys Tyr Gln Val Pro Glu Phe Asp Ser Ser Thr Ile Lys Asn Ile
                340                 345                 350 tct tct gca aaa ggc ctg gac gtt tgg gac agc tgg cca tta caa aac          1104
Ser Ser Ala Lys Gly Leu Asp Val Trp Asp Ser Trp Pro Leu Gln Asn
        355                 360                 365 gct gac ggc act gtc gca aac tat cac ggc tac cac atc gtc ttt gca          1152
Ala Asp Gly Thr Val Ala Asn Tyr His Gly Tyr His Ile Val Phe Ala
        370                 375                 380 tta gcc gga gat cct aaa aat gcg gat gac aca tcg att tac atg ttc          1200
Leu Ala Gly Asp Pro Lys Asn Ala Asp Asp Thr Ser Ile Tyr Met Phe
385                 390                 395                 400 tat caa aaa gtc ggc gaa act tct att gac agc tgg aaa aac gct ggc          1248
Tyr Gln Lys Val Gly Glu Thr Ser Ile Asp Ser Trp Lys Asn Ala Gly
                405                 410                 415 cgc gtc ttt aaa gac agc gac aaa ttc gat gca aat gat tct atc cta          1296
Arg Val Phe Lys Asp Ser Asp Lys Phe Asp Ala Asn Asp Ser Ile Leu
                420                 425                 430 aaa gac caa aca caa gaa tgg tca ggt tca gcc aca ttt aca tct gac          1344
Lys Asp Gln Thr Gln Glu Trp Ser Gly Ser Ala Thr Phe Thr Ser Asp
                435                 440                 445 gga aaa atc cgt tta ttc tac act gat ttc tcc ggt aaa cat tac ggc          1392
Gly Lys Ile Arg Leu Phe Tyr Thr Asp Phe Ser Gly Lys His Tyr Gly
450                 455                 460
```

| | | | | | | | | | | | | | | | | |
|---|---|---|---|---|---|---|---|---|---|---|---|---|---|---|---|---|
| aaa | caa | aca | ctg | aca | act | gca | caa | gtt | aac | gta | tca | gca | tca | gac | agc | 1440 |
| Lys | Gln | Thr | Leu | Thr | Thr | Ala | Gln | Val | Asn | Val | Ser | Ala | Ser | Asp | Ser | |
| 465 | | | | 470 | | | | | 475 | | | | | 480 | | |

| | | | | | | | | | | | | | | | | |
|---|---|---|---|---|---|---|---|---|---|---|---|---|---|---|---|---|
| tct | ttg | aac | atc | aac | ggt | gta | gag | gat | tat | aaa | tca | atc | ttt | gac | ggt | 1488 |
| Ser | Leu | Asn | Ile | Asn | Gly | Val | Glu | Asp | Tyr | Lys | Ser | Ile | Phe | Asp | Gly | |
| | | | | 485 | | | | | 490 | | | | | 495 | | |

| | | | | | | | | | | | | | | | | |
|---|---|---|---|---|---|---|---|---|---|---|---|---|---|---|---|---|
| gac | gga | aaa | acg | tat | caa | aat | gta | cag | cag | ttc | atc | gat | gaa | ggc | aac | 1536 |
| Asp | Gly | Lys | Thr | Tyr | Gln | Asn | Val | Gln | Gln | Phe | Ile | Asp | Glu | Gly | Asn | |
| | | 500 | | | | | 505 | | | | | 510 | | | | |

| | | | | | | | | | | | | | | | | |
|---|---|---|---|---|---|---|---|---|---|---|---|---|---|---|---|---|
| tac | agc | tca | ggc | gac | aac | cat | acg | ctg | aga | gat | cct | cac | tac | gta | gaa | 1584 |
| Tyr | Ser | Ser | Gly | Asp | Asn | His | Thr | Leu | Arg | Asp | Pro | His | Tyr | Val | Glu | |
| | | 515 | | | | | 520 | | | | | 525 | | | | |

| | | | | | | | | | | | | | | | | |
|---|---|---|---|---|---|---|---|---|---|---|---|---|---|---|---|---|
| gat | aaa | ggc | cac | aaa | tac | tta | gta | ttt | gaa | gca | aac | act | gga | act | gaa | 1632 |
| Asp | Lys | Gly | His | Lys | Tyr | Leu | Val | Phe | Glu | Ala | Asn | Thr | Gly | Thr | Glu | |
| | | 530 | | | | | 535 | | | | | 540 | | | | |

| | | | | | | | | | | | | | | | | |
|---|---|---|---|---|---|---|---|---|---|---|---|---|---|---|---|---|
| gat | ggc | tac | caa | ggc | gaa | gaa | tct | tta | ttt | aac | aaa | gca | tac | tat | ggc | 1680 |
| Asp | Gly | Tyr | Gln | Gly | Glu | Glu | Ser | Leu | Phe | Asn | Lys | Ala | Tyr | Tyr | Gly | |
| 545 | | | | 550 | | | | | 555 | | | | | 560 | | |

| | | | | | | | | | | | | | | | | |
|---|---|---|---|---|---|---|---|---|---|---|---|---|---|---|---|---|
| aaa | agc | aca | tca | ttc | ttc | cgt | caa | gaa | agt | caa | aaa | ctt | ctg | caa | agc | 1728 |
| Lys | Ser | Thr | Ser | Phe | Phe | Arg | Gln | Glu | Ser | Gln | Lys | Leu | Leu | Gln | Ser | |
| | | | | 565 | | | | | 570 | | | | | 575 | | |

| | | | | | | | | | | | | | | | | |
|---|---|---|---|---|---|---|---|---|---|---|---|---|---|---|---|---|
| gat | aaa | aaa | cgc | acg | gct | gag | tta | gca | aac | ggc | gct | ctc | ggt | atg | att | 1776 |
| Asp | Lys | Lys | Arg | Thr | Ala | Glu | Leu | Ala | Asn | Gly | Ala | Leu | Gly | Met | Ile | |
| | | | | 580 | | | | | 585 | | | | | 590 | | |

| | | | | | | | | | | | | | | | | |
|---|---|---|---|---|---|---|---|---|---|---|---|---|---|---|---|---|
| gag | cta | aac | gat | gat | tac | aca | ctg | aaa | aaa | gtg | atg | aaa | ccg | ctg | att | 1824 |
| Glu | Leu | Asn | Asp | Asp | Tyr | Thr | Leu | Lys | Lys | Val | Met | Lys | Pro | Leu | Ile | |
| | | | | 595 | | | | | 600 | | | | | 605 | | |

| | | | | | | | | | | | | | | | | |
|---|---|---|---|---|---|---|---|---|---|---|---|---|---|---|---|---|
| gca | tct | aac | aca | gta | aca | gat | gaa | att | gaa | cgc | gcg | aac | gtc | ttt | aaa | 1872 |
| Ala | Ser | Asn | Thr | Val | Thr | Asp | Glu | Ile | Glu | Arg | Ala | Asn | Val | Phe | Lys | |
| | 610 | | | | | 615 | | | | | 620 | | | | | |

| | | | | | | | | | | | | | | | | |
|---|---|---|---|---|---|---|---|---|---|---|---|---|---|---|---|---|
| atg | aac | ggc | aaa | tgg | tac | ctg | ttc | act | gac | tcc | cgc | gga | tca | aaa | atg | 1920 |
| Met | Asn | Gly | Lys | Trp | Tyr | Leu | Phe | Thr | Asp | Ser | Arg | Gly | Ser | Lys | Met | |
| 625 | | | | 630 | | | | | 635 | | | | | 640 | | |

| | | | | | | | | | | | | | | | | |
|---|---|---|---|---|---|---|---|---|---|---|---|---|---|---|---|---|
| acg | att | gac | ggc | att | acg | tct | aac | gat | att | tac | atg | ctt | ggt | tat | gtt | 1968 |
| Thr | Ile | Asp | Gly | Ile | Thr | Ser | Asn | Asp | Ile | Tyr | Met | Leu | Gly | Tyr | Val | |
| | | | | 645 | | | | | 650 | | | | | 655 | | |

| | | | | | | | | | | | | | | | | |
|---|---|---|---|---|---|---|---|---|---|---|---|---|---|---|---|---|
| tct | aat | tct | tta | act | ggc | cca | tac | aag | ccg | ctg | aac | aaa | act | ggc | ctt | 2016 |
| Ser | Asn | Ser | Leu | Thr | Gly | Pro | Tyr | Lys | Pro | Leu | Asn | Lys | Thr | Gly | Leu | |
| | | | | 660 | | | | | 665 | | | | | 670 | | |

| | | | | | | | | | | | | | | | | |
|---|---|---|---|---|---|---|---|---|---|---|---|---|---|---|---|---|
| gtg | tta | aaa | atg | gat | ctt | gat | cct | aac | gat | gta | acc | ttt | act | tac | tca | 2064 |
| Val | Leu | Lys | Met | Asp | Leu | Asp | Pro | Asn | Asp | Val | Thr | Phe | Thr | Tyr | Ser | |
| | | 675 | | | | | 680 | | | | | 685 | | | | |

| | | | | | | | | | | | | | | | | |
|---|---|---|---|---|---|---|---|---|---|---|---|---|---|---|---|---|
| cac | ttc | gct | gta | cct | caa | gcg | aaa | gga | aac | aat | gtc | gtg | att | aca | agc | 2112 |
| His | Phe | Ala | Val | Pro | Gln | Ala | Lys | Gly | Asn | Asn | Val | Val | Ile | Thr | Ser | |
| | | 690 | | | | | 695 | | | | | 700 | | | | |

| | | | | | | | | | | | | | | | | |
|---|---|---|---|---|---|---|---|---|---|---|---|---|---|---|---|---|
| tat | atg | aca | aac | aga | gga | ttc | tac | gca | gac | aaa | caa | tca | acg | ttt | gcg | 2160 |
| Tyr | Met | Thr | Asn | Arg | Gly | Phe | Tyr | Ala | Asp | Lys | Gln | Ser | Thr | Phe | Ala | |
| 705 | | | | 710 | | | | | 715 | | | | | 720 | | |

| | | | | | | | | | | | | | | | | |
|---|---|---|---|---|---|---|---|---|---|---|---|---|---|---|---|---|
| cca | agc | ttc | ctg | ctg | aac | atc | aaa | ggc | aag | aaa | aca | tct | gtt | gtc | aaa | 2208 |
| Pro | Ser | Phe | Leu | Leu | Asn | Ile | Lys | Gly | Lys | Lys | Thr | Ser | Val | Val | Lys | |
| | | | | 725 | | | | | 730 | | | | | 735 | | |

| | | | | | | | | | | | | | |
|---|---|---|---|---|---|---|---|---|---|---|---|---|---|
| gac | agc | atc | ctt | gaa | caa | gga | caa | tta | aca | gtt | aac | aaa | tag tga | 2253 |
| Asp | Ser | Ile | Leu | Glu | Gln | Gly | Gln | Leu | Thr | Val | Asn | Lys | | |
| | | | | 740 | | | | | 745 | | | | | |

<210> SEQ ID NO 20
<211> LENGTH: 749
<212> TYPE: PRT
<213> ORGANISM: Artificial Sequence
<220> FEATURE:
<223> OTHER INFORMATION: Synthetic Construct -continued

<400> SEQUENCE: 20

```
Met Thr Ser Ile Phe Ala Glu Gln Thr Val Glu Val Lys Ser Ala
1               5                  10                  15

Ile Glu Thr Ala Asp Gly Ala Leu Asp Leu Tyr Asn Lys Tyr Leu Asp
                20                  25                  30

Gln Val Ile Pro Trp Lys Thr Phe Asp Glu Thr Ile Lys Glu Leu Ser
            35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Lys Ala Ser Ala Gln
                100                 105                 110

Lys Asp Ile Leu Ile Arg Ile Leu Asp Asp Gly Val Lys Lys Leu Asn
            115                 120                 125

Glu Ala Gln Lys Ser Leu Leu Thr Ser Ser Gln Ser Phe Asn Asn Ala
    130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
                180                 185                 190

Ile Ile Ser Tyr Ser Ile Ala Ala Gly Val Ile Glu Gly Lys Leu Ile
            195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
                260                 265                 270

Leu Leu Lys Gly Ala Ala Lys Lys Met Ile Asn Thr Cys Asn Glu Tyr
            275                 280                 285

Gln Gln Arg His Gly Lys Lys Thr Leu Phe Glu Val Pro Asp Val Ala
    290                 295                 300

Ser Lys Glu Thr Asn Gln Lys Pro Tyr Lys Glu Thr Tyr Gly Ile Ser
305                 310                 315                 320

His Ile Thr Arg His Asp Met Leu Gln Ile Pro Glu Gln Gln Lys Asn
                325                 330                 335

Glu Lys Tyr Gln Val Pro Glu Phe Asp Ser Ser Thr Ile Lys Asn Ile
                340                 345                 350

Ser Ser Ala Lys Gly Leu Asp Val Trp Asp Ser Trp Pro Leu Gln Asn
            355                 360                 365

Ala Asp Gly Thr Val Ala Asn Tyr His Gly Tyr His Ile Val Phe Ala
    370                 375                 380

Leu Ala Gly Asp Pro Lys Asn Ala Asp Asp Thr Ser Ile Tyr Met Phe
385                 390                 395                 400

Tyr Gln Lys Val Gly Glu Thr Ser Ile Asp Ser Trp Lys Asn Ala Gly
```

```
            405                 410                 415
Arg Val Phe Lys Asp Ser Asp Lys Phe Asp Ala Asn Asp Ser Ile Leu
            420                 425                 430

Lys Asp Gln Thr Gln Glu Trp Ser Gly Ser Ala Thr Phe Thr Ser Asp
            435                 440                 445

Gly Lys Ile Arg Leu Phe Tyr Thr Asp Phe Ser Gly Lys His Tyr Gly
            450                 455                 460

Lys Gln Thr Leu Thr Thr Ala Gln Val Asn Val Ser Ala Ser Asp Ser
465                 470                 475                 480

Ser Leu Asn Ile Asn Gly Val Glu Asp Tyr Lys Ser Ile Phe Asp Gly
            485                 490                 495

Asp Gly Lys Thr Tyr Gln Asn Val Gln Gln Phe Ile Asp Glu Gly Asn
            500                 505                 510

Tyr Ser Ser Gly Asp Asn His Thr Leu Arg Asp Pro His Tyr Val Glu
            515                 520                 525

Asp Lys Gly His Lys Tyr Leu Val Phe Glu Ala Asn Thr Gly Thr Glu
            530                 535                 540

Asp Gly Tyr Gln Gly Glu Glu Ser Leu Phe Asn Lys Ala Tyr Tyr Gly
545                 550                 555                 560

Lys Ser Thr Ser Phe Phe Arg Gln Glu Ser Gln Lys Leu Leu Gln Ser
            565                 570                 575

Asp Lys Lys Arg Thr Ala Glu Leu Ala Asn Gly Ala Leu Gly Met Ile
            580                 585                 590

Glu Leu Asn Asp Asp Tyr Thr Leu Lys Lys Val Met Lys Pro Leu Ile
            595                 600                 605

Ala Ser Asn Thr Val Thr Asp Glu Ile Glu Arg Ala Asn Val Phe Lys
            610                 615                 620

Met Asn Gly Lys Trp Tyr Leu Phe Thr Asp Ser Arg Gly Ser Lys Met
625                 630                 635                 640

Thr Ile Asp Gly Ile Thr Ser Asn Asp Ile Tyr Met Leu Gly Tyr Val
            645                 650                 655

Ser Asn Ser Leu Thr Gly Pro Tyr Lys Pro Leu Asn Lys Thr Gly Leu
            660                 665                 670

Val Leu Lys Met Asp Leu Asp Pro Asn Asp Val Thr Phe Thr Tyr Ser
            675                 680                 685

His Phe Ala Val Pro Gln Ala Lys Gly Asn Asn Val Val Ile Thr Ser
            690                 695                 700

Tyr Met Thr Asn Arg Gly Phe Tyr Ala Asp Lys Gln Ser Thr Phe Ala
705                 710                 715                 720

Pro Ser Phe Leu Leu Asn Ile Lys Gly Lys Lys Thr Ser Val Val Lys
            725                 730                 735

Asp Ser Ile Leu Glu Gln Gly Gln Leu Thr Val Asn Lys
            740                 745
```

<210> SEQ ID NO 21
<211> LENGTH: 921
<212> TYPE: DNA
<213> ORGANISM: Salmonella typhi

<400> SEQUENCE: 21
atgactagta tttttgcaga acaaactgta gaggtagtta aaagcgcgat cgaaaccgca   60 gatgggcat tagatcttta taacaaatac ctcgaccagg tcatcccctg gaagaccttt   120
gatgaaacca taaagagtt aagccgtttt aaacaggagt actcgcagga agcttctgtt   180

```
ttagttggtg atattaaagt tttgcttatg gacagccagg acaagtattt tgaagcgaca      240
caaactgttt atgaatggtg tggtgtcgtg acgcaattac tctcagcgta tattttacta      300
tttgatgaat ataatgagaa aaaagcatca gcccagaaag acattctcat taggatatta      360
gatgatggtg tcaagaaact gaatgaagcg caaaaatctc tcctgacaag ttcacaaagt      420
ttcaacaacg cttccggaaa actgctggca ttagatagcc agttaactaa tgattttcg       480 gaaaaagta gttatttcca gtcacaggtg gatagaattc gtaaggaagc ttatgccggt       540
gctgcagccg gcatagtcgc cggtccgttt ggattaatta tttcctattc tattgctgcg      600
ggcgtgattg aagggaaatt gattccgaaa ttgaataaca ggctaaaaac agtgcaaaat      660
ttctttacta gcttatcagc tacagtgaaa caagcgaata agatatcga tgcggcaaaa      720 ttgaaattag ccactgaaat agcagcaatt ggggagataa aacggaaac cgaaacaacc       780 agattctacg ttgattatga tgatttaatg ctttctttat taaaggagc tgcaagaaa        840 atgattaaca cctgtaatga ataccaacaa cgtcatggta agaagacgct tttcgaggtt      900
cctgacgtcg ctagctgata a                                                921

<210> SEQ ID NO 22
<211> LENGTH: 1102
<212> TYPE: DNA
<213> ORGANISM: Salmonella typhi

<400> SEQUENCE: 22
ggaggtaata ggtaagaata ctttataaaa caggtactta attgcaattt atatatttaa      60
agaggcaaat gattatgacc ggaatatttg cagaacaaac tgtagaggta gttaaaagcg      120
cgatcgaaac cgcagatggg gcattagatc tttataacaa ataccctgac caggtcatcc      180
cctggaagac ctttgatgaa accataaaag agttaagccg ttttaaacag gagtactcgc      240
aggaagcttc tgttttagtt ggtgatatta agttttgct tatggacagc caggacaagt       300
attttgaagc gacacaaact gtttatgaat ggtgtggtgt cgtgacgcaa ttactctcag      360
cgtatatttt actatttgat gaatataatg agaaaaaagc atcagcccag aaagacattc      420
tcattaggat attagatgat ggtgtcaaga aactgaatga agcgcaaaaa tctctcctga      480
caagttcaca aagtttcaac aacgcttccg gaaaactgct ggcattagat agccagttaa      540
ctaatgattt ttcggaaaaa gtagttatt ccagtcacag gtggataga attcgtaagg        600 aagcttatgc cggtgctgca gccggcatag tcgccggtcc gtttggatta attatttcct      660
attctattgc tgcgggcgtg attgaaggga aattgattcc agaattgaat aacaggctaa      720
aaacagtgca aaatttcttt actagcttat cagctacagt gaaacaagcg aataaagata      780
tcgatgcggc aaaattgaaa ttagccactg aaatagcagc aattggggag ataaaaacgg      840
aaaccgaaac aaccagattc tacgttgatt atgatgattt aatgctttct ttattaaaag      900
gagctgcaaa gaaatgatt aacacctgta atgaatacca acaaagacac ggtaagaaga      960
cgcttttcga ggttcctgac gtctgataca ttttcattcg atctgtgtac ttttaacgcc      1020
cgatagcgta agaaaatga gagacggaga aaaagcgata ttcaacagcc cgataaacaa      1080
gagtcgttac cgggctgacg ag                                               1102

<210> SEQ ID NO 23
<211> LENGTH: 1102
<212> TYPE: DNA
<213> ORGANISM: Salmonella paratyphi

<400> SEQUENCE: 23
```

```
ggaggcaata ggtaggaata agttataaaa caatagctta attgcaattt atatatttaa      60
agaggcaaat gattatgact ggaatatttg cagaacaaac tgtagaggta gttaaaagcg     120
cgatcgaaac cgcagatggg gcattagatt tttataacaa atacctcgac caggttatcc     180
cctggaagac ctttgatgaa accataaaag agttaagccg ttttaaacag gagtactcgc     240
aggaagcttc tgttttagtt ggtgatatta agttttgct tatggacagc caggataagt      300
attttgaagc gacacaaact gtttatgaat ggtgtggtgt cgtgacgcaa ttactctcag     360
cgtatatttt actatttgat gaatataatg agaaaaaagc atcagcgcag aaagacattc     420
tcatcaggat attagatgat ggcgtcaata aactgaatga agcgcaaaaa tctctcctgg     480
gaagttcaca agtttcaac aacgcttcag gaaaactgct ggcattagat agccagttaa      540
ctaatgattt ctcggaaaaa agtagttatt ccagtcaca ggtggataga attcgtaagg      600
aagcttatgc cggtgctgca gcaggcatag tcgccggtcc gtttggatta attatttcct     660
attctattgc tgcgggcgtg attgaaggga aattgattcc agaattgaat gacaggctaa     720
aagcagtgca aaatttcttt actagcttat cagtcacagt gaaacaagcg aataaagata     780
tcgatgcggc aaaattgaaa ttagccactg aaatagcagc aattggggag ataaaaacgg     840
aaaccgaaac aaccagattc tacgttgatt atgatgattt aatgctttct ttactaaaag     900
gagctgcaaa gaaaatgatt aacacctgta atgaatacca acaaaggcac ggtaagaaga     960
cgcttctcga ggttcctgac atctgataca ttttcattcg ctctgtttac ttttaacgcc    1020
cgatagcgtg aagaaaatga gagacggaga aaaagcgata ttcaacagcc cgataaacaa    1080
gagtcgttac cgggctggcg ag                                             1102

<210> SEQ ID NO 24
<211> LENGTH: 904
<212> TYPE: DNA
<213> ORGANISM: Shigella flexneri

<400> SEQUENCE: 24
atgactgaaa tcgttgcaga taaaacggta gaagtagtta aaaacgcaat cgaaaccgca      60
gatggagcat tagatcttta taataaatat ctcgatcagg tcatcccctg gcagaccttt     120
gatgaaacca taaaagagtt aagtcgcttt aaacaggagt attcacaggc agcctccgtt     180
ttagtcggcg atattaaaac cttacttatg gatagccagg ataagtattt tgaagcaacc     240
caaacagtgt atgaatggtg tggtgttgcg acgcaattgc tcgcagcgta tatttgcta    300 tttgatgagt acaatgagaa gaaagcatcc gcccctcatt aaggtactgg atgacggcat     360
cacgaagctg aatgaagcgc aaaattccct gctggtaagc tcacaaagtt caacaacgc      420 ttccgggaaa ctgctggcgt tagatagcca gttaaccaat gattttcag aaaaaagcag     480 ctatttccag tcacaggtag ataaaatcag gaaggaagcg tatgccggtg ccgcagccgg     540
tgtcgtcgcc ggtccatttg gtttaatcat ttcctattct attgctgcgg gcgtagttga     600
agggaaactg attccagaat gaagaacaa gttaaaatct gtgcagagtt tctttaccac     660
cctgtctaac acggttaaac aagcgaataa agatatcgat gccgccaaat tgaaattaac     720
caccgaaata gccgccatcg gggagataaa acggaaact gaaaccacca gattctatgt      780
tgattatgat gatttaatgc tttctttgct aaaagcagcg gccaaaaaaa tgattaacac     840
ctgtaatgag tatcagaaaa gacacggtaa aagacactc tttgaggtac ctgaagtctg     900
ataa                                                                 904
```

<210> SEQ ID NO 25
<211> LENGTH: 1080
<212> TYPE: DNA
<213> ORGANISM: Escherichia coli

<400> SEQUENCE: 25

```
agaaataaag acattgacgc atcccgcccg gctaactatg aattagatga agtaaaattt      60
attaatagtt gtaaaacagg agtttcatta caatttatat atttaaagag gcgaatgatt     120
atgactgaaa tcgttgcaga taaaacggta gaagtagtta aaaacgcaat cgaaaccgca     180
gatggagcat tagatcttta taataaatat ctcgatcagg tcatcccctg gcagaccttt     240
gatgaaacca taaagagtt aagtcgcttt aaacaggagt attcacaggc agcctccgtt     300
ttagtcggcg atattaaaac cttacttatg gatagccagg ataagtattt tgaagcaacc     360
caaacagtgt atgaatggtg tggtgttgcg acgcaattgc tcgcagcgta tattttgcta     420
tttgatgagt acaatgagaa gaaagcatcc gcccagaaag acattctcat taaggtactg     480
gatgacggca tcacgaagct gaatgaagcg caaaaatccc tgctggtaag ctcacaaagt     540
ttcaacaacg cttccgggaa actgctggcg ttagatagcc agttaaccaa tgattttttca    600
gaaaaaagca gctatttcca gtcacaggta gataaaatca ggaaggaagc atatgccggt     660
gccgcagccg gtgtcgtcgc cggtccattt ggattaatca tttcctattc tattgctgcg     720
ggcgtagttg aaggaaaact gattccagaa ttgaagaaca agttaaaatc tgtgcagaat     780
ttctttacca ccctgtctaa cacggttaaa caagcgaata agatatcga tgccgccaaa     840
ttgaaattaa ccaccgaaat agccgccatc ggtgagataa aacggaaac tgaaacaacc     900
agattctacg ttgattatga tgatttaatg ctttctttgc taaaagaagc ggccaaaaaa    960
atgattaaca cctgtaatga gtatcagaaa agacacggta aaaagacact ctttgaggta   1020
cctgaagtct gataagcgat tattctctcc atgtactcaa ggtataaggt ttatcacatt   1080
```

<210> SEQ ID NO 26
<211> LENGTH: 26
<212> TYPE: DNA
<213> ORGANISM: Artificial Sequence
<220> FEATURE:
<223> OTHER INFORMATION: chemically-synthesized PCR primer

<400> SEQUENCE: 26

```
cttctccttt actcatgcta gccaca                                           26
```

<210> SEQ ID NO 27
<211> LENGTH: 36
<212> TYPE: DNA
<213> ORGANISM: Artificial Sequence
<220> FEATURE:
<223> OTHER INFORMATION: chemically-synthesized PCR primer

<400> SEQUENCE: 27

```
aaatggtacc tccaaaataa ggaggaaaaa aaaatg                                36
```

<210> SEQ ID NO 28
<211> LENGTH: 40
<212> TYPE: DNA
<213> ORGANISM: Artificial Sequence
<220> FEATURE:
<223> OTHER INFORMATION: chemically-synthesized PCR primer

<400> SEQUENCE: 28

```
agctatagca atgacgcggg cgttattaaa ggcaaactga                            40
```

<210> SEQ ID NO 29
<211> LENGTH: 40
<212> TYPE: DNA
<213> ORGANISM: Artificial Sequence
<220> FEATURE:
<223> OTHER INFORMATION: chemically-synthesized PCR primer

<400> SEQUENCE: 29

```
tcagtttgcc tttaataacg cccgcgtcat tgctatagct                40
```

<210> SEQ ID NO 30
<211> LENGTH: 881
<212> TYPE: DNA
<213> ORGANISM: Artificial Sequence
<220> FEATURE:
<223> OTHER INFORMATION: chemically-synthesized clyA I198N mutant

<400> SEQUENCE: 30

```
atgactagta ttttgcgga acagaccgtg gaagtggtta aaagcgcgat cgaaaccgcg    60
gatggcgcgt tagatcttta taacaaatat ctggatcagg tgattccgtg gaaaaccttt   120
gatgaaacca ttaaagaact gagccgtttt aaacaggaat atagccagga agcgagcgtg   180
ctggtgggcg atattaaagt gctgctgatg gatagccagg ataaatattt tgaagcgacc   240
cagaccgtgt atgaatggtg cggcgtggtt acccagctgc tgagcgcgta tatcctgctg   300
tttgatgaat ataacgaaaa gaaagcgagc gctcagaaag atattctgat tcgtattctg   360
gatgacggcg tgaaaaaact gaacgaagcg cagaaaagcc tgctgaccag cagccagagc   420
tttaacaatg cgtccggaaa actgctggcg ctggatagcc agctgaccaa cgattttagc   480
gaaaaaagca gctattttca gagccaggtg gatagaattc gtaaagaagc ctatgccggc   540
gctgcagccg gcattgtggc tggtccgttt ggcctgatta tcagctatag caatgccgcg   600
ggcgttattg aaggcaaaac tgattccgga actgaataacc gtctgaaaac cgttcagaat   660
ttcttacaa gcttaagcgc gaccgtgaaa caggcgaaca aagatatcga tgcggcaaaa   720
ctgaaactgg cgaccgaaat tgcggctatt ggcgaaatta aaccgaaaac cgaaaccacc   780
cgttttatg tggattatga tgacctgatg ctgagcctgc tgaaaggcgc ggcaaagaaa   840
atgattaaca cctgcaacga atatcagcag cgtcatggca a                       881
```

<210> SEQ ID NO 31
<211> LENGTH: 919
<212> TYPE: DNA
<213> ORGANISM: Artificial Sequence
<220> FEATURE:
<223> OTHER INFORMATION: chemically-synthesized clyA I198N, A199D, E204K
       mutant

<400> SEQUENCE: 31

```
atgactagta ttttgcgga acagaccgtg gaagtggtta aaagcgcgat cgaaaccgcg    60
gatggcgcgt tagatcttta taacaaatat ctggatcagg tgattccgtg gaaaaccttt   120
gatgaaacca ttaaagaact gagccgtttt aaacaggaat atagccagga agcgagcgtg   180
ctggtgggcg atattaaagt gctgctgatg gatagccagg ataaatattt tgaagcgacc   240
cagaccgtgt atgaatggtg cggcgtggtt acccagctgc tgagcgcgta tatcctgctg   300
tttgatgaat ataacgaaaa gaaagcgagc gctcagaaag atattctgat tcgtattctg   360
gatgacggcg tgaaaaaact gaacgaagcg cagaaaagcc tgctgaccag cagccagagc   420
tttaacaatg cgtccggaaa actgctggcg ctggatagcc agctgaccaa cgattttagc   480
```

```
gaaaaaagca gctatttca gagccaggtg gatagaattc gtaaagaagc ctatgccggc    540
gctgcagccg gcattgtggc tggtccgttt ggcctgatta tcagctatag caatgacgcg    600
ggcgttatta aaggcaaact gattccggaa ctgaataacc gtctgaaaac cgttcagaat    660
ttctttacaa gcttaagcgc gaccgtgaaa caggcgaaca agatatcga tgcggcaaaa    720 ctgaaactgg cgaccgaaat tgcggctatt ggcgaaatta aaccgaaac cgaaaccacc    780 cgttttatg tggattatga tgacctgatg ctgagcctgc tgaaaggcgc ggcaaagaaa    840
atgattaaca cctgcaacga atatcagcag cgtcatggca gaaaaccct gtttgaagtg    900 ccggatgtgg ctagcatga                                                919
```

<210> SEQ ID NO 32
<211> LENGTH: 6273
<212> TYPE: DNA
<213> ORGANISM: Artificial Sequence
<220> FEATURE:
<223> OTHER INFORMATION: chemically-synthesized plasmid encoding codon-optimized ClyA fused to GFPuv

<400> SEQUENCE: 32

```
gaattaattc tgtggtagca cagaataatg aaaagtgtgt aaagaagggt aaaaaaaacc     60
gaatgcgagg catccggttg aaatagggggt aaacagacat tcagaaatga atgacggtaa    120
taaataaagt taatgatgat agcgggagtt attctagttg cgagtgaagg ttttgttttg    180
acattcagtg ctgtcaaata cttaagaata agttattgat tttaaccttg aattattatt    240
gcttgatgtt aggtgcttat ttcgccattc cgcaataatc ttaaaaagtt ccctttgcat    300
tacattttga acatctata gcgataaatg aaacatctta aaagttttag tatcatattc     360
gtgttggatt attctgcatt tttggggaga atggacttgc cgactgatta atgagggtta    420
atcagtatgc agtggcataa aaaagcaaat aaaggcatat aacagatcga tcttaaacat    480
ccacaggagg atgggatcca aaataaggag gaaaaaaaaa tgactagtat ttttgcggaa    540
cagaccgtgg aagtggttaa aagcgcgatc gaaaccgcgg atggcgcgtt agatctttat    600
aacaaatatc tggatcaggt gattccgtgg aaaacctttg atgaaaccat taagaactg     660 agccgttta acaggaata tagccaggaa gcgagcgtgc tggtgggcga tattaaagtg     720
ctgctgatgg atagccagga taaatatttt gaagcgaccc agaccgtgta tgaatggtgc    780
ggcgtggtta cccagctgct gagcgcgtat atcctgctgt ttgatgaata taacgaaaag    840
aaagcgagcg ctcagaaaga tattctgatt cgtattctgg atgacggcgt gaaaaaactg    900
aacgaagcgc agaaaagcct gctgaccagc agccagagct taacaatgc gtccggaaaa    960 ctgctggcgc tggatagcca gctgaccaac gattttagcg aaaaaagcag ctatttcag    1020 agccaggtgg atagaattcg taaagaagcc tatgccggcg ctgcagccgg cattgtggct    1080
ggtccgtttg gcctgattat cagctatagc attgccgcgg cgttattga aggcaaactg    1140 attccggaac tgaataaccg tctgaaaacc gttcagaatt ctttacaag cttaagcgcg    1200 accgtgaaac aggcgaacaa agatatcgat gcggcaaaac tgaaactggc gaccgaaatt    1260
gcggctattg gcgaaattaa accgaaaccc gaaaccaccc gttttatgt ggattatgat    1320 gacctgatgc tgagcctgct gaaaggcgcg gcaaagaaaa tgattaacac ctgcaacgaa    1380
tatcagcagc gtcatggcaa gaaaaccctg tttgaagtgc cggatgtggc tagctgataa    1440
cctagcgtcg acactagccc gcctaatgag cgggcttttt tttctcggcc taggagatac    1500
ttaacaggga agtgagaggg ccgcggcaaa gccgtttttc cataggctcc gcccccctga    1560
```

```
caagcatcac gaaatctgac gctcaaatca gtggtggcga aacccgacag gactataaag    1620
ataccaggcg tttccccctg gcggctccct cgtgcgctct cctgttcctg cctttcggtt    1680
taccggtgtc attccgctgt tatggccgcg tttgtctcat tccacgcctg acactcagtt    1740
ccgggtaggc agttcgctcc aagctggact gtatgcacga accccccgtt cagtccgacc    1800
gctgcgcctt atccggtaac tatcgtcttg agtccaaccc ggaaagacat gcaaaagcac    1860
cactggcagc agccactggt aattgattta gaggagttag tcttgaagtc atgcgccggt    1920
taaggctaaa ctgaaaggac aagttttggt gactgcgctc ctccaagcca gttacctcgg    1980
ttcaaagagt tggtagctca gagaaccttc gaaaaaccgc cctgcaaggc ggttttttcg    2040
ttttcagagc aagagattac gcgcagacca aaacgatctc aagaagatca tcttattaat    2100
cagataaaat atttctagga tctaaaacac taggcccaag agtttgtaga aacgcaaaaa    2160
ggccatccgt caggatggcc ttctgcttaa tttgatgcct ggcagtttat ggcgggcgtc    2220
ctgcccgcca ccctccgggc cgttgcttcg caacgttcaa atccgctccc ggcggatttg    2280
tcctactcag gagagcgttc accgacaaac aacagataaa acgaaaggcc cagtctttcg    2340
actgagcctt tcgttttatt tgatgcctgg cagttcccta ctctcgcatg gggagacccc    2400
acactaccat cggcgctacg gcgtttcact tctgagttcg gcatggggtc aggtgggacc    2460
accgcgctac tgccgccagg caaattctgt tttatcagac cgcttctgcg ttctgattta    2520
atctgtatca ggctgaaaat cttctctcat ccgccaaaac agccaagctg gatctggcaa    2580
atcgctgaat attccttttg tctccgacca tcaggcacct gagtcgctgt ctttttcgtg    2640
acattcagtt cgctgcgctc acggctctgg cagtgaatgg gggtaaatgg cactacaggc    2700
gccttttatg gattcatgca aggaaactac ccataataca agaaaagccc gtcacgggct    2760
tctcagggcg ttttatggcg ggtctgctat gtggtgctat ctgactttt gctgttcagc    2820 agttcctgcc ctctgatttt ccagtctgac cacttcggat tatcccgtga caggtcattc    2880
agactggcta atgcacccag taaggcagcg gtatcatcaa caggcttacc cgtcttactg    2940
tcaaccggat ctaaaacact agcccaacct ttcatagaag gcggcggtgg aatcgaaatc    3000
tcgtgatggc aggttgggcg tcgcttggtc ggtcatttcg aacccagag tcccgctcag    3060 aagaactcgt caagaaggcg atagaaggcg atgcgctgcg aatcgggagc ggcgataccg    3120
taaagcacga ggaagcggtc agcccattcg ccgccaagct cttcagcaat atcacgggta    3180
gccaacgcta tgtcctgata gcggtccgcc acacccagcc ggccacagtc gatgaatcca    3240
gaaaagcggc cattttccac catgatattc ggcaagcagg catcgccatg ggtcacgacg    3300
agatcctcgc cgtcgggcat gcgcgccttg agcctggcga acagttcggc tggcgcgagc    3360
ccctgatgct cttcgtccag atcatcctga tcgacaagac cggcttccat ccgagtacgt    3420
gctcgctcga tgcgatgttt cgcttggtgg tcgaatgggc aggtagccgg atcaagcgta    3480
tgcagccgcc gcattgcatc agccatgatg gatactttct cggcaggagc aaggtgagat    3540
gacaggagat cctgccccgg cacttcgccc aatagcagcc agtcccttcc cgcttcagtg    3600
acaacgtcga gcacagctgc gcaaggaacg cccgtcgtgg ccagccacga tagccgcgct    3660
gcctcgtcct gcagttcatt cagggcaccg gacaggtcgg tcttgacaaa aagaaccggg    3720
cgcccctgcg ctgacagccg gaacacggcg gcatcagagc agccgattgt ctgttgtgcc    3780
cagtcatagc cgaatagcct ctccacccaa gcggccggag aacctgcgtg caatccatct    3840
tgttcaatca tgcgaaacga tcctcatcct gtctcttgat cagatcttga tccctgcgc    3900
```

-continued

```
catcagatcc ttggcggcaa gaaagccatc cagtttactt tgcagggctt cccaaccta    3960
ccagagggcg ccccagccgt ggcaattccg gttcgctgct agacaacatc agcaaggaga   4020
aaggggctac cggcgaacca gcagcccctt tataaaggcg cttcagtagt cagaccagca   4080
tcagtcctga aaaggcgggc ctgcgcccgc ctccaggttg ctacttaccg gattcgtaag   4140
ccatgaaagc cgccacctcc ctgtgtccgt ctctgtaacg aatctcgcac agcgattttc   4200
gtgtcagata agtgaatatc aacagtgtga gacacacgat caacacacac cagacaaggg   4260
aacttcgtgg tagtttcatg gccttcttct ccttgcgcaa agcgcggtaa gaggctatcc   4320
tgatgtggac tagacatagg gatgcctcgt ggtggttaat gaaaattaac ttactacggg   4380
gctatcttct ttctgccaca caacacggca acaaaccacc ttcacgtcat gaggcagaaa   4440
gcctcaagcg ccgggcacat catagcccat atacctgcac gctgaccaca ctcactttcc   4500
ctgaaaataa tccgctcatt cagaccgttc acgggaaatc cgtgtgattg ttgccgcatc   4560
acgctgcctc ccggagtttg tctcgagcac ttttgttacc cgccaaacaa acccaaaaa   4620
caacccatac ccaacccaat aaaacaccaa acaagacaa ataatcattg attgatggtt    4680
gaaatggggt aaacttgaca aacaaaccca cttaaaaccc aaaacatacc caaacacaca   4740
ccaaaaaaac accataagga gttttataaa tgttggtatt cattgatgac ggttcaacaa   4800
acatcaaact acagtggcag gaaagcgacg gaacaattaa acagcacatt agcccgaaca   4860
gcttcaaacg cgagtgggca gtctcttttg gtgataaaaa ggtctttaac tacacactga   4920
acggcgaaca gtattcattt gatccaatca gcccggatgc tgtagtcaca accaatatcg   4980
catggcaata cagcgacgtt aatgtcgttg cagtgcatca cgccttactg accagtggtc   5040
tgccggtaag cgaagtggat attgtttgca cacttcctct gacagagtat tacgacagaa   5100
ataaccaacc caatacggaa aatattgagc gtaagaaagc aaacttccgg aaaaaaatta   5160
cattaaatgg cggggataca ttcacaataa aagatgtaaa agtcatgcct gaatctatac   5220
cggcaggtta tgaagttcta caagaactgg atgagttaga ttctttatta attatagatc   5280
tcgggggcac cacattagat atttctcagg taatggggaa attatcgggg atcagtaaaa   5340
tatacggaga ctcatctctt ggtgtctctc tggttacatc tgcagtaaaa gatgccctt    5400
ctcttgcgag aacaaaagga agtagctatc ttgctgacga tataatcatt cacagaaaag   5460
ataataacta tctgaagcaa cgaattaatg atgagaacaa aatatcaata gtcaccgaag   5520
caatgaatga agcacttcgt aaacttgagc aacgtgtatt aaatacgctc aatgaatttt   5580
ctggttatac tcatgttatg gttataggcg gtggcgcaga attaatatgc gatgcagtaa   5640
aaaaacacac acagattcgt gatgaacgtt ttttcaaaac caataactct caatatgatt   5700
tagttaacgg tatgtatctc ataggtaatt aatgatggac aagcgcagaa ccattgcctt   5760
caaactaaat ccagatgtaa atcaaacaga taaaattgtt tgtgatacac tggacagtat   5820
cccgcaaggg gaacgaagcc gccttaaccg ggccgcactg acggcaggtc tggccttata   5880
cagacaagat ccccggaccc cttttccttt atgtgagctg ctgacgaaag aaaccacatt   5940
ttcagatatc gtgaatatat tgagatcgct atttccaaaa gagatggccg attttaattc   6000
ttcaatagtc actcaatcct cttcacaaca agagcaaaaa agtgatgaag agaccaaaaa   6060
aaatgcgatg aagctaataa attaattcaa ttattattga gttcccttta tccactatca   6120
ggctggataa agggaactca atcaagttat tttcttacca gtcattacat aatcgttatt   6180
atgaaataat cgtttgcact gtctctgtta ttcaggcaat ttcaataaag gcacttgctc   6240
acgctctgtc attttctgaa actcttcatg ctg                                6273
```

<210> SEQ ID NO 33
<211> LENGTH: 909
<212> TYPE: DNA
<213> ORGANISM: Artificial Sequence
<220> FEATURE:
<223> OTHER INFORMATION: chemically-synthesized codon-optimized S. Typhi clyA polynucleotide sequence

<400> SEQUENCE: 33
atgactagta tttttgcgga acagaccgtg gaagtggtta aaagcgcgat cgaaaccgcg 60
gatggcgcgt tagatcttta taacaaatat ctggatcagg tgattccgtg gaaaaccttt 120
gatgaaacca ttaaagaact gagccgtttt aaacaggaat atagccagga agcgagcgtg 180
ctggtgggcg atattaaagt gctgctgatg gatagccagg ataaatattt tgaagcgacc 240
cagaccgtgt atgaatggtg cggcgtggtt acccagctgc tgagcgcgta tatcctgctg 300
tttgatgaat ataacgaaaa gaaagcgagc gctcagaaag atattctgat tcgtattctg 360
gatgacggcg tgaaaaaact gaacgaagcg cagaaaagcc tgctgaccag cagccagagc 420
tttaacaatg cgtccggaaa actgctggcg ctggatagcc agctgaccaa cgattttagc 480
gaaaaaagca gctattttca gagccaggtg gatagaattc gtaaagaagc ctatgccggc 540
gctgcagccg gcattgtggc tggtccgttt ggcctgatta tcagctatag cattgccgcg 600
ggcgttattg aaggcaaact gattccggaa ctgaataacc gtctgaaaac cgttcagaat 660
ttctttacaa gcttaagcgc gaccgtgaaa caggcgaaca aagatatcga tgcggcaaaa 720
ctgaaactgg cgaccgaaat tgcggctatt ggcgaaatta aaccgaaac cgaaaccacc 780
cgtttttatg tggattatga tgacctgatg ctgagcctgc tgaaaggcgc ggcaaagaaa 840
atgattaaca cctgcaacga atatcagcag cgtcatggca agaaaaccct gtttgaagtg 900
ccggatgtg 909

<210> SEQ ID NO 34
<211> LENGTH: 36
<212> TYPE: DNA
<213> ORGANISM: Artificial Sequence
<220> FEATURE:
<223> OTHER INFORMATION: chemically-synthesized PCR primer
<400> SEQUENCE: 34
tatttcctat tctaatgctg cgggcgtgat tgaagg 36

<210> SEQ ID NO 35
<211> LENGTH: 36
<212> TYPE: DNA
<213> ORGANISM: Artificial Sequence
<220> FEATURE:
<223> OTHER INFORMATION: chemically-synthesized PCR primer
<400> SEQUENCE: 35
ccttcaatca cgcccgcagc attagaatag gaaata 36

<210> SEQ ID NO 36
<211> LENGTH: 37
<212> TYPE: DNA
<213> ORGANISM: Artificial Sequence
<220> FEATURE:
<223> OTHER INFORMATION: chemically-synthesized PCR primer
<400> SEQUENCE: 36
tgattaacac ctggaatgaa taccaacaac gtcatgg 37

<210> SEQ ID NO 37
<211> LENGTH: 37
<212> TYPE: DNA
<213> ORGANISM: Artificial Sequence
<220> FEATURE:
<223> OTHER INFORMATION: chemically-synthesized PCR primer

<400> SEQUENCE: 37
ccatgacgtt gttggtattc attccaggtg ttaatca                                37

<210> SEQ ID NO 38
<211> LENGTH: 96
<212> TYPE: DNA
<213> ORGANISM: Artificial Sequence
<220> FEATURE:
<223> OTHER INFORMATION: chemically-synthesized PCR primer

<400> SEQUENCE: 38
tctagagaag ttcctattct atatatagta taggaacttc gctagctcat gtttgacagc        60
ttatcatcga taagctttaa tgcggtagtt tatcac                                  96

<210> SEQ ID NO 39
<211> LENGTH: 97
<212> TYPE: DNA
<213> ORGANISM: Artificial Sequence
<220> FEATURE:
<223> OTHER INFORMATION: chemically-synthesized PCR primer

<400> SEQUENCE: 39
tctagagaag ttcctatact atatatagaa taggaacttc gctagcctat caggtcgagg        60
tggcccggct ccatgcaccg cgacgcaacg cggggag                                 97

<210> SEQ ID NO 40
<211> LENGTH: 1368
<212> TYPE: DNA
<213> ORGANISM: Artificial Sequence
<220> FEATURE:
<223> OTHER INFORMATION: chemically-synthesized FRT-tetA-FRT Xba I-Not I
      cassette

<400> SEQUENCE: 40
tctagagaag ttcctattct atatatagta taggaacttc gctagctcat gtttgacagc        60
ttatcatcga taagctttaa tgcggtagtt tatcacagtt aaattgctaa cgcagtcagg       120
caccgtgtat gaaatctaac aatgcgctca tcgtcatcct cggcaccgtc acctggatg        180 ctgtaggcat aggcttggtt atgccggtac tgccgggcct cttgcgggat atcgtccatt       240
ccgacagcat cgccagtcac tatggcgtgc tgctagcgct atatgcgttg atgcaatttc       300
tatgcgcacc cgttctcgga gcactgtccg accgctttgg ccgccgccca gtcctgctcg       360
cttcgctact tggagccact atcgactacg cgatcatggc gaccacaccc gtcctgtgga       420
tcctctacgc cggacgcatc gtggccggca tcaccggcgc cacaggtgcg gttgctggcg       480
cctatatcgc cgacatcacc gatggggaag atcgggctcg ccacttcggg ctcatgagcg       540
cttgtttcgg cgtgggtatg gtggcaggcc ccgtggccgg gggactgttg gcgccatct        600 ccttgcatgc accattcctt gcggcggcgg tgctcaacgg cctcaaccta ctactgggct       660
gcttcctaat gcaggagtcg cataagggag agcgtcgacc gatgcccttg agagccttca       720
acccagtcag ctccttccgg tgggcgcggg gcatgactat cgtcgccgca cttatgactg       780
tcttctttat catgcaactc gtaggacagg tgccggcagc gctctgggtc attttcggcg       840

```
aggaccgctt tcgctggagc gcgacgatga tcggcctgtc gcttgcggta ttcggaatct    900
tgcacgccct cgctcaagcc ttcgtcactg gtcccgccac caaacgtttc ggcgagaagc    960
aggccattat cgccggcatg gcggccgacg cgctgggcta cgtcttgctg gcgttcgcga   1020
cgcgaggctg gatggccttc cccattatga ttcttctcgc ttccggcggc atcgggatgc   1080
ccgcgttgca ggccatgctg tccaggcagg tagatgacga ccatcaggga cagcttcaag   1140
gatcgctcgc ggctcttacc agcctaactt cgatcactgg accgctgatc gtcacggcga   1200
tttatgccgc ctcggcgagc acatggaacg ggttggcatg gattgtaggc gccgccctat   1260
accttgtctg cctccccgcg ttgcgtcgcg gtgcatggag ccgggccacc tcgacctgat   1320
aggctagcga agttcctatt ctatatatag tataggaact tctctaga              1368
```

<210> SEQ ID NO 41
<211> LENGTH: 6979
<212> TYPE: DNA
<213> ORGANISM: Artificial Sequence
<220> FEATURE:
<223> OTHER INFORMATION: pGEN222SXbaI Expression Plasmid

<400> SEQUENCE: 41

```
gaattctgtg gtagcacaga ataatgaaaa gtgtgtaaag aagggtaaaa aaaaccgaat     60
gcgaggcatc cggttgaaat aggggtaaac agacattcag aaatgaatga cgtaataaa    120 taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcatttttg gggagaatgg acttgccgac tgattaatga gggttaatca    420
gtatgcagtg gcataaaaaa gcaaataaag gcatataaca gatcgatctt aaacatccac    480
aggaggatat ctgatgagta aggagaagaa cttttcact ggagttgtcc caattcttgt    540
tgaattagat ggtgatgtta atgggcacaa attttctgtc agtggagagg gtgaaggtga    600
tgcaacatac ggaaaactta cccttaaatt tatttgcact actggaaaac tacctgttcc    660
atggccaaca cttgtcacta cttttctctta tggtgttcaa tgcttttccc gttatccgga    720
tcatatgaaa cggcatgact ttttcaagag tgccatgccc gaaggttatg tacaggaacg    780
cactatatct ttcaaagatg acgggaacta caagacgcgt gctgaagtca agtttgaagg    840
tgataccctt gttaatcgta tcgagttaaa aggtattgat tttaaagaag atggaaacat    900
tctcggacac aaactcgagt acaactataa ctcacacaat gtatacatca cggcagacaa    960
acaaaagaat ggaatcaaag ctaacttcaa aattcgccac aacattgaag atggatccgt   1020
tcaactagca gaccattatc aacaaaatac tccaattggc gatggccctg tccttttacc   1080
agacaaccat tacctgtcga cacaatctgc cctttcgaaa gatcccaacg aaaagcgtga   1140
ccacatggtc cttcttgagt ttgtaactgc tgctgggatt acacatggca tggatgagct   1200
ctacaaataa tgagctagcc cgcctaatga gcgggctttt ttttctcggc ctaggagata   1260
cttaacaggg aagtgagagg gccgcggcaa agccgttttt ccataggctc cgccccctg    1320 acaagcatca cgaaatctga cgctcaaatc agtggtggcg aaacccgaca ggactataaa   1380
gataccaggc gtttccccct ggcggctccc tcgtgcgctc tcctgttcct gcctttcggt   1440
ttaccggtgt cattccgctg ttatggccgc gtttgtctca ttccacgcct gacactcagt   1500
```

-continued

```
tccgggtagg cagttcgctc caagctggac tgtatgcacg aacccccgt tcagtccgac      1560 cgctgcgcct tatccggtaa ctatcgtctt gagtccaacc cggaaagaca tgcaaaagca      1620
ccactggcag cagccactgg taattgattt agaggagtta gtcttgaagt catgcgccgg      1680
ttaaggctaa actgaaagga caagttttgg tgactgcgct cctccaagcc agttacctcg      1740
gttcaaagag ttggtagctc agagaaccct cgaaaaaccg ccctgcaagg cggttttttc      1800
gttttcagag caagagatta cgcgcagacc aaaacgatct caagaagatc atcttattaa      1860
tcagataaaa tatttctagg atctaaaaca ctaggcccaa gagtttgtag aaacgcaaaa      1920
aggccatccg tcaggatggc cttctgctta atttgatgcc tggcagttta tggcgggcgt      1980
cctgcccgcc accctccggg ccgttgcttc gcaacgttca aatccgctcc cggcggattt      2040
gtcctactca ggagagcgtt caccgacaaa caacagataa aacgaaaggc ccagtctttc      2100
gactgagcct ttcgttttat ttgatgcctg gcagttccct actctcgcat ggggagaccc      2160
cacactacca tcggcgctac ggcgtttcac ttctgagttc ggcatggggt caggtgggac      2220
caccgcgcta ctgccgccag gcaaattctg ttttatcaga ccgcttctgc gttctgattt      2280
aatctgtatc aggctgaaaa tcttctctca tccgccaaaa cagccaagct ggatctggca      2340
aatcgctgaa tattccttt t gtctccgacc atcaggcacc tgagtcgctg tcttttcgt       2400 gacattcagt tcgctgcgct cacggctctg gcagtgaatg ggggtaaatg cactacagg       2460 cgccttttat ggattcatgc aaggaaacta cccataatac aagaaaagcc cgtcacgggc      2520
ttctcagggc gttttatggc gggtctgcta tgtggtgcta tctgactttt tgctgttcag      2580
cagttcctgc cctctgattt tccagtctga ccacttcgga ttatcccgtg acaggtcatt      2640
cagactggct aatgcaccca gtaaggcagc ggtatcatca acaggcttac ccgtcttact      2700
gtcaaccgga tctaaaacac tagctctagc tattgtttta atgacaaatc agaacggaat      2760
gtcatcatca aagtccatcg gcggctcgtt agacggcgct gccggagcgg actgctgcgg      2820
gcgagactgc gcgccgccgc tgaactgatt gccaccctgc ggctgctgag gctgaccca       2880 accgccctgc ggctgaccac caccgatatt gccacctgcc ggagcgccac caccctgacg      2940
accacccagc atctgcatgg tgccgccaac gttcaccacg acttctgtgg tgtagcgatc      3000
ctgaccggat tgatcggtcc atttacgggt acgcagctga ccttcgatat aaacctgaga      3060
acctttacgc agatattcgc tcgccacttc tgccagtttg ccaacagca caacgcggtg       3120 ccattcagtc tgttctttca tctcgccggt cgctttatca cgccaggatt cggaagtagc      3180
cagcgtaatg ttggcaactg cgccaccatt tggcatgtag cgtacttccg ggtcctgacc      3240
cagattacca acgagaataa ccttgtttac gcctctgctg gccatgttcg tgtctcctga      3300
aaaaaatcgt tctgaataag tgtaaacgcg cgattgtacc attaccaata gcgcttttac      3360
tatgttgtga cctcggttcc gggaaacaaa cctggccaga cattgttaca caacactccg      3420
gataatgcat tccaatactg tatattcatt caggtcaatc atatgaaggg cgaattctgc      3480
agatatccat cacactggcg gccgctcgag catgcatcta gactcgagta agggattttg      3540
gtcatgagat tatcaaaaag gatcttcacc tagatccttt taaattaaaa atgaagtttt      3600
aaatcaatct aaagtatata tgagtaaact tggtctgaca gttaccaatg cttaatcagt      3660
gaggcaccta tctcagcgat ctgtctattt cgttcatcca tagttgcctg actccccgtc      3720
gtgtagataa ctacgatacg ggagggctta ccatctggcc ccagtgctgc aatgataccg      3780
cgagacccac gctcaccggc tccagattta tcagcaataa accagccagc cggaagggcc      3840
gagcgcagaa gtggtcctgc aactttatcc gcctccatcc agtctattaa ttgttgccgg      3900
```

```
gaagctagag taagtagttc gccagttaat agtttgcgca acgttgttgc cattgctaca    3960
ggcatcgtgg tgtcacgctc gtcgtttggt atggcttcat tcagctccgg ttcccaacga    4020
tcaaggcgag ttacatgatc ccccatgttg tgcaaaaaag cggttagctc cttcggtcct    4080
ccgatcgttg tcagaagtaa gttggccgca gtgttatcac tcatggttat ggcagcactg    4140
cataattctc ttactgtcat gccatccgta agatgctttt ctgtgactgg tgagtactca    4200
accaagtcat tctgagaata gtgtatgcgg cgaccgagtt gctcttgccc ggcgtcaaca    4260
cgggataata ccgcgccaca tagcagaact ttaaaagtgc tcatcattgg aaaacgttct    4320
tcggggcgaa aactctcaag gatcttaccg ctgttgagat ccagttcgat gtaacccact    4380
cgtgcaccca actgatcttc agcatctttt actttcacca gcgtttctgg gtgagcaaaa    4440
acaggaaggc aaaatgccgc aaaaaaggga ataagggcga cacggaaatg ttgaatactc    4500
atactcttcc ttttcaata ttattgaagc atttatcagg gttattgtct catgagcgga    4560
tacatatttg aatgtattta gaaaaataaa caaataggg ttccgcgcac atttccccga    4620
aaagtgccac ctgacgtcta agaaaccatt attatcatga cattaaccta aaaaatagg    4680 cgtatcacga ggccctttcg tctgctagac aacatcagca aggagaaagg ggctaccggc    4740
gaaccagcag ccccttata aaggcgcttc agtagtcaga ccagcatcag tcctgaaaag    4800
gcgggcctgc gcccgcctcc aggttgctac ttaccggatt cgtaagccat gaaagccgcc    4860
acctccctgt gtccgtctct gtaacgaatc tcgcacagcg atttttcgtgt cagataagtg    4920 aatatcaaca gtgtgagaca cacgatcaac acacaccaga caaggaact tcgtggtagt    4980 ttcatggcct tcttctcctt gcgcaaagcg cggtaagagg ctatcctgat gtggactaga    5040
catagggatg cctcgtggtg gttaatgaaa attaacttac tacggggcta tcttctttct    5100
gccacacaac acggcaacaa accaccttca cgtcatgagg cagaaagcct caagcgccgg    5160
gcacatcata gcccatatac ctgcacgctg accacactca cttccctga aaataatccg    5220 ctcattcaga ccgttcacgg gaaatccgtg tgattgttgc cgcatcacgc tgcctcccgg    5280
agtttgtctc tagaactttt gttacccgcc aaacaaaacc caaaacaac ccataccaa    5340 cccaataaaa caccaaaaca agacaaataa tcattgattg atggttgaaa tggggtaaac    5400
ttgacaaaca aacccactta aaacccaaaa cataccaaa cacacaccaa aaaacacca    5460 taaggagttt tataaatgtt ggtattcatt gatgacggtt caacaaacat caaactacag    5520
tggcaggaaa gcgacggaac aattaaacag cacattagcc cgaacagctt caaacgcgag    5580
tgggcagtct cttttggtga taaaaggtc tttaactaca cactgaacgg cgaacagtat    5640
tcatttgatc caatcagccc ggatgctgta gtcacaacca atatcgcatg gcaatacagc    5700
gacgttaatg tcgttgcagt gcatcacgcc ttactgacca gtggtctgcc ggtaagcgaa    5760
gtggatattg tttgcacact tcctctgaca gagtattacg acagaaataa ccaacccaat    5820
acggaaaata ttgagcgtaa gaaagcaaac ttccggaaaa aaattacatt aaatggcggg    5880
gatacattca caataaaaga tgtaaaagtc atgcctgaat ctataccggc aggttatgaa    5940
gttctacaag aactggatga gttagattct ttattaatta tagatctcgg ggcaccaca    6000 ttagatattt ctcaggtaat ggggaaatta tcggggatca gtaaaatata cggagactca    6060
tctcttggtg tctctctggt tacatctgca gtaaagatg cccttctct tgcgagaaca    6120 aaaggaagta gctatcttgc tgacgatata atcattcaca gaaagataa taactatctg    6180 aagcaacgaa ttaatgatga gaacaaaata tcaatagtca ccgaagcaat gaatgaagca    6240
```

-continued

| | | | | | | |
|---|---|---|---|---|---|---|
| cttcgtaaac | ttgagcaacg | tgtattaaat | acgctcaatg | aattttctgg | ttatactcat | 6300 |
| gttatggtta | taggcggtgg | cgcagaatta | atatgcgatg | cagtaaaaaa | acacacacag | 6360 |
| attcgtgatg | aacgttttt | caaaaccaat | aactctcaat | atgatttagt | taacggtatg | 6420 |
| tatctcatag | gtaattaatg | atggacaagc | gcagaaccat | tgccttcaaa | ctaaatccag | 6480 |
| atgtaaatca | aacagataaa | attgtttgtg | atacactgga | cagtatcccg | caagggggaac | 6540 |
| gaagccgcct | taaccgggcc | gcactgacgg | caggtctggc | cttatacaga | caagatcccc | 6600 |
| ggacccctt | ccttttatgt | gagctgctga | cgaaagaaac | cacattttca | gatatcgtga | 6660 |
| atatattgag | atcgctattt | ccaaaagaga | tggccgattt | taattcttca | atagtcactc | 6720 |
| aatcctcttc | acaacaagag | caaaaaagtg | atgaagagac | caaaaaaaat | gcgatgaagc | 6780 |
| taataaatta | attcaattat | tattgagttc | cctttatcca | ctatcaggct | ggataaaggg | 6840 |
| aactcaatca | agttattttc | ttaccagtca | ttacataatc | gttattatga | aataatcgtt | 6900 |
| tgcactgtct | ctgttattca | ggcaatttca | ataaaggcac | ttgctcacgc | tctgtcattt | 6960 |
| tctgaaactc | ttcatgctg | | | | | 6979 |